US010533997B2

(12) United States Patent
Shi et al.

(10) Patent No.: US 10,533,997 B2
(45) Date of Patent: Jan. 14, 2020

(54) REVERSE GENETICS SYSTEM OF ZIKA VIRUS

(71) Applicants: Pei-Yong Shi, Galveston, TX (US); Chao Shan, Galveston, TX (US); Xuping Xie, Galveston, TX (US)

(72) Inventors: Pei-Yong Shi, Galveston, TX (US); Chao Shan, Galveston, TX (US); Xuping Xie, Galveston, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 16/098,401

(22) PCT Filed: May 3, 2017

(86) PCT No.: PCT/US2017/030810
§ 371 (c)(1),
(2) Date: Nov. 1, 2018

(87) PCT Pub. No.: WO2017/192701
PCT Pub. Date: Nov. 9, 2017

(65) Prior Publication Data
US 2019/0120841 A1 Apr. 25, 2019

Related U.S. Application Data

(60) Provisional application No. 62/330,958, filed on May 3, 2015, provisional application No. 62/455,846, filed on Feb. 7, 2017.

(51) Int. Cl.
A61K 39/00 (2006.01)
A61K 39/12 (2006.01)
C12N 7/00 (2006.01)
A61K 45/06 (2006.01)
C07H 19/20 (2006.01)
G01N 33/569 (2006.01)
C12Q 1/70 (2006.01)
C12Q 1/6897 (2018.01)

(52) U.S. Cl.
CPC ..... G01N 33/56983 (2013.01); C12Q 1/6897 (2013.01); C12Q 1/70 (2013.01); G01N 2333/185 (2013.01)

(58) Field of Classification Search
CPC ................ A61K 2300/00; A61K 39/12; A61K 31/7072; A61K 31/7068; C12N 7/00
See application file for complete search history.

(56) References Cited

U.S. PATENT DOCUMENTS 8,691,961 B1 * 4/2014 Puffer ...................... C12N 7/00
424/218.1
2005/0058987 A1 3/2005 Shi et al.
2006/0115896 A1 6/2006 Wong et al.
2011/0212986 A1 9/2011 Shi et al.

FOREIGN PATENT DOCUMENTS

EP 2980099 2/2016

OTHER PUBLICATIONS

Alkan et al., "Ecuador Paraiso Escondido Virus, a New Flavivirus Isolated from New World Sand Flies in Ecuador, Is the First Representative of a Novel Clade in the Genus *Flavivirus*" *J. Virol.*, 2015, 89:11773-11785.
Calvet et al., "Detection and sequencing of Zika virus from amniotic fluid of fetuses with microcephaly in Brazil: a case study" *The Lancet Infectious Diseases*, 2016, 16:653-660.
Chouin-Carneiro et al., "Differential Susceptibilities of *Aedes aegypti* and *Aedes albopictus* from the Americas to Zika Virus" *PLoS Negl Trop Dis*, 2016, 10(3):e0004543.
Dowd et al., "Rapid Development of a DNA Vaccine for Zika Virus" *Science*, 2016, 354:237-240.
Dudley et al., "Natural history of Asian lineage Zika virus infection in macaques" *bioRxiv*, 2016, 29 Pages.
Faria et al., "Zika virus in the Americas: Early epidemiological and genetic findings" *Science*, 2016, 352(6283):345-349.
Fitzpatrick et al., "Population variation of West Nile virus confers a host-specific fitness benefit in mosquitos" *Virology*, 2010, 404:89-95.
Garcia et al., "Recognition of Synthetic Oligopeptides from Nonstructural Proteins NS1 and NS3 of Dengue-4 Virus by Sera from Dengue Virus—Infected Children" *American Journal of Tropical Medicine & Hygiene*, 1997, 56:466-470.
GenBank No. JN860885.1, 2012, Accessed from the Internet on May 28, 2019; URL: < https://www.ncbi.nlm.nih.gov/nuccore/JN860885 >.
Haddow et al., "Genetic characterization of Zika virus strains: geographic expansion of the Asian lineage" *PLoS Negl. Trop. Dis.*, 2012, 6:e1477.
Hanna et al., "N-Linked Glycosylation of West Nile Virus Envelope Proteins Influences Particle Assembly and Infectivity" *J. Virol*, 2005, 79:13262-13274.
Harvey et al., "Tetracycline-Inducible Packaging Cell Line for Production of Flavivirus Replicon Particles" *J. Virol.*, 2004, 78:531-538.
International Search Report and Written Opinion issued in International Patent Application No. PCT/US2017/030810, dated Aug. 9, 2017.
Khromykh & Westaway, "Completion of Kunjin virus RNA sequence and recovery of an infectious RNA transcribed from stably cloned full-length cDNA." *Journal of Virology*, 1994, 68:4580-4588.
Khromykh et al., "Encapsidation of the Flavivirus Kunjin Replicon RNA by Using a Complementation System Providing Kunjin Virus Structural Proteins in trans" *J. Virol.*, 1998, 72:5967-5977.

(Continued)

Primary Examiner — Barry A Chestnut
(74) Attorney, Agent, or Firm — Norton Rose Fulbright US LLP

(57) ABSTRACT

Embodiments of the invention are directed to stable full-length cDNA clones of a clinical, Asian lineage ZIKV strain. Certain embodiments of the invention are directed to high-throughput assays for ZIKV and dengue virus (DENV) diagnosis.

19 Claims, 11 Drawing Sheets
Specification includes a Sequence Listing.

(56) References Cited

OTHER PUBLICATIONS

Lai et al., "Infectious RNA transcribed from stably cloned full-length cDNA of dengue type 4 virus." *PNAS USA.*, 1991, 88:5139-5143.
Lanciotti et al., "Genetic and Serologic Properties of Zika Virus Associated with an Epidemic, Yap State, Micronesia, 2007" *Emerg. Infect. Dis.*, 2008, 14:1232-1239.
Lazear et al., "A mouse model of Zika virus pathogenesis" *Cell Host & Microbe*, 2016, 19(5):720-730.
Li et al., "Rational Design of a Flavivirus Vaccine by Abolishing Viral RNA 2'-O Methylation" *J. Virol.*, 2013, 87:5812-5819.
Li et al., "Recovery of a chemically synthesized Japanese encephalitis virus reveals two critical adaptive mutations in NS2B and NS4A" *J. Gen. Virol.*, 2014, 95:806-815.
Mandl et al., "Infectious cDNA clones of tick-borne encephalitis virus European subtype prototypic strain Neudoerfl and high virulence strain Hypr" *Journal of General Virology*, 1997, 78:1049-1057.
Mlakar et al., "Zika Virus Associated with Microcephaly" *N. Engl. J. Med.*, 2016, 374:951-958.
Musso and Gubler, "Zika Virus" *Clin Microbiol Rev*, 2016, 29:487-524.
Puig-Basagoiti et al., "High-Throughput Assays Using a Luciferase-Expressing Replicon, Virus-Like Particles, and Full-Length Virus for West Nile Virus Drug Discovery" *Antimicrob Agent Chemother*, 2005, 49:4980-4988.
Rice et al., "Transcription of infectious yellow fever RNA from full-length cDNA templates produced by in vitro ligation." *New Biologist*, 1989, 1:285-296.
Rossi et al., "Characterization of a Novel Murine model to Study Zika Virus," *Am J. Trop Med Hyg.*, 2016, 94(6):1362-1369.
Schoggins et al., "Dengue reporter viruses reveal viral dynamics in interferon receptor-deficient mice and sensitivity to interferon effectors in vitro" *Proc Natl Acad Sci U.S.A.*, 2012, 109:14610-14615.
Shan et al., "A rapid Zika diagnostic assay to measure neutralizing antibodies in patients" *EBio Medicine*, 2017, 17:157-162.
Shan et al., "An Infectious cDNA Clone of Zika Virus to Study Viral Virulence, Mosquito Transmission, and Antiviral Inhibitors." *Cell Host Microbe*, 2016, 19:891-900.
Shan et al., "Zika Virus: Diagnosis, Therapeutics, and Vaccine" *ACS Infectious Diseases*, 2016, 2:170-172.
Shi et al., "Infectious cDNA Clone of the Epidemic West Nile Virus from New York City" *J. Virol.*, 2002, 76:5847-5856.
Shu et al., "Dengue NS1-specific antibody responses: Isotype distribution and serotyping in patients with dengue fever and dengue hemorrhagic fever" *Journal of Medical Virology*, 2000, 62:224-232.
Stables et al., "Interim Guidelines for the Evaluation and Testing of Infants with Possible Congenital Zika Virus Infection—United States" *MMWR MOrb Mortal Wkly Rep*, 2016, 65:63-67.
Stettler et al., "Specificity, cross-reactivity, and function of antibodies elicited by Zika virus infection." *Science*, 2016, 353:823-826.
Sumiyoshi et al., "Infectious Japanese encephalitis virus RNA can be synthesized from in vitro-ligated cDNA templates." *Journal of Virology*, 1992, 66:5425-5431.
Tsetsarkin & Weaver, "Sequential Adaptive Mutations Enhance Efficient Vector Switching by Chikungunya Virus and Its Epidemic Emergence" *PLoS Pathog.*, 2011, 7:e1002412.
Tsetsarkin et al., "Multi-peaked adaptive landscape for chikungunya virus evolution predicts continued fitness optimization in *Aedes albopictus* mosquitoes" *Nature Communications*, 2014, 5:4048.
Weaver et al., "Zika Virus: History, Emergence, Biology, and Prospects for Control" *Antiviral Res*, 2016, 130:69-80.
Whitehead et al., "Prospects for a dengue virus vaccine" *Nat. Rev. Microbiol.*, 2007, 5:518-528.
Wong et al., "A Multiplex Microsphere Immunoassay for Zika Virus Diagnosis" *EBIoMedicine*, 2017, 16:136-140.
Wong et al., "Immunoassay Targeting Nonstructural Protein 5 to Differentiate West Nile Virus Infection from Dengue and St. Louis Encephalitis Virus Infections and from Flavivirus Vaccination" *J. Clin. Microbiol*, 2003, 41:4217-4223.
Zhang et al., "Generation of a recombinant West Nile virus stably expressing the Gaussia luciferase for neutralization assay." *Virus Res.*, 2016, 211:17-24.
Zmurko et al., "The viral polymerase inhibitor 7-deaza-2'-C-methyladenosine is a potent inhibitor of an in vitro Zika virus replication and delays progression in a robust mouse infection model" *PLoS Negl. Trop. Dis.*, 2016, 10(5):e0004695.
Zou et al., "Development and characterization of a stable luciferase dengue virus for high-throughput screening" *Antiviral Res.*, 2011, 91:11-19.
Zust et al., "Rational Design of a Live Attenuated Dengue Vaccine: 2'-O-Methyltransferase Mutants Are Highly Attenuated and Immunogenic in Mice and Macaques" *PLoS Pathog.*, 2013, 9:e1003521.

* cited by examiner

MKNPKKKSGGFRIVNMLKRGVARVSPFGGLKRLPAGLLLGHGPIRMVLAILAFLRFTAIKPSLGLINRW
GSVGKKEAMEIIKKFKKDLAAMLRIINARKEKKRRGTDTSVGIVGLLLTTAMAVEVTRRGNAYYMYL
DRSDAGEAISFPTTMGMNKCYIQIMDLGHMCDATMSYECPMLDEGVEPDDVDCWCNTTSTWVVYGT
CHHKKGEARRSRRAVTLPSHSTRKLQTRSQTWLESREYTKHLIRVENWIFRNPGFALAAAAIAWLLGS
STSQKVIYLVMILLIAPAYSIRCIGVSNRDFVEGMSGGTWVDVVLEHGGCVTVMAQDKPTVDIELVTTT
VSNMAEVRSYCYEASISDMASDSRCPTQGEAYLDKQSDTQYVCKRTLVDRGWGNGCGLFGKGSLVT
CAKFACSKKMTGKSIQPENLEYRIMLSVHGSQHSGMIVNDTGHETDENRAKVEITPNSPRAEATLGGFG
SLGLDCEPRTGLDFSDLYYLTMNNKHWLVHKEWFHDIPLPWHAGADTGTPHWNNKEALVEFKDAHA
KRQTVVVLGSQEGAVHTALAGALEAEMDGAKGRLSSGHLKCRLKMDKLRLKGVSYSLCTAAFTFTKI
PAETLHGTVTVEVQYAGTDGPCKVPAQMAVDMQTLTPVGRLITANPVITESTENSKMMLELDPPFGDS
YIVIGVGEKKITHHWHRSGSTIGKAFEATVRGAKRMAVLGDTAWDFGSVGGALNSLGKGIHQIFGAAF
KSLFGGMSWFSQILIGTLLVWLGLNTKNGSISLMCLALGGVLIFLSTAVSADVGCSVDFSKKETRCGTG
VFVYNDVEAWRDRYKYHPDSPRRLAAAVKQAWEDGICGISSVSRMENIMWRSVEGELNAILEENGVQ
LTVVVGSVKNPMWRGPQRLPVPVNELPHGWKAWGKSYFVRAAKTNNSFVVDGDTLKECPLKHRAW
NSFLVEDHGFGVFHTSVWLKVREDYSLECDPAVIGTAAKGKEAVHSDLGYWIESEKNDTWRLKRAHL
IEMKTCEWPKSHTLWTDGIEESDLIIPKSLAGPLSHHNTREGYRTQMEGPWHSEELEIRFEECPGTKVHV
EETCGTRGPSLRSTTASGRVIEEWCCRECTMPPLSFRAKDGCWYGMEIRPRKEPESNLVRSMVTAGST
DHMDHFSLGVLVILLMVQEGLKKRMTTKIIISTSMAVLVAMILGGFSMSDLAKLAILMGATFAEMNTG
GDVAHLALIAAFKVRPALLVSFIFRANWTPRESMLLALASCLLQTAISALEGDLMVPINGFALAWLAIR
AMVVPRTDNITLAILAALTPLARGTLLVAWRAGLATCGGFMLLSLKGKGSVKKNLPFVMALGLTAVR
LVDPINVVGLLLLTRSGKRSWPPSEVLTAVGLICALAGGFAKADIEMAGPMAAVGLLIVSYVVSGKSV
DMYIERAGDITWEKDAEVTGNSPRLDVALDESGDFSLVEDDGPPMREIILKVVLMAICGMNPIAIPFAA
GAWYVYVKTGKRSGALWDVPAPKEVKKGETTDGVYRVMTRRLLGSTQVGVGVMQEGVFHTMWHV
TKGSALRSGEGRLDPYWGDVKQDLVSYCGPWKLDAAWDGHSEVQLLAVPPGERARNIQTLPGIFKTK
DGDIGAVALDYPAGTSGSPILDKCGRVIGLYGNGVVIKNGSYVSAITQGRREEETPVECFEPSMLKKKQ
LTVLDLHPGAGKTRRVLPEIVREAIKTRLRTVILAPTRVVAAEMEEALRGLPVRYMTTAVNVTHSGTEI
VDLMCHATFTSRLLQPIRVPNYNLYIMDEAHFTDPSSIAARGYISTRVEMGEAAAIFMTATPPGTRDAFP
DSNSPIMDTEVEVPERAWSSGFDWVTDHSGKTVWFVPSVRNGNEIAACLTKAGKRVIQLSRKTFETEF
QKTKHQEWDFVVTTDISEMGANFKADRVIDSRRCLKPVILDGERVILAGPMPVTHASAAQRRGRIGRN
PNKPGDEYLYGGGCAETDEDHAHWLEARMLLDNIYLQDGLIASLYRPEADKVAAIEGEFKLRTEQRKT
FVELMKRGDLPVWLAYQVASAGITYTDRRWCFDGTTNNTIMEDSVPAEVWTRYGEKRVLKPRWMD
ARVCSDHAALKSFKEFAAGKRGAAFGVMEALGTLPGHMTERFQEAIDNLAVLMRAETGSRPYKAAA
AQLPETLETIMLLGLLGTVSLGIFFVLMRNKGIGKMGFGMVTLGASAWLMWLSEIEPARIACVLIVVFL
LLVVLIPEPEKQRSPQDNQMAIIIMVAVGLLGLITANELGWLERTKSDLSHLMGRREEGATIGFSMDIDL
RPASAWAIYAALTTFITPAVQHAVTTSYNNYSLMAMATQAGVLFGMGKGMPFYAWDFGVPLLMIGC
YSQLTPLTLIVAIILLVAHYMYLIPGLQAAAARAAQKRTAAGIMKNPVVDGIVVTDIDTMTIDPQVEKK
MGQVLLIAVAVSSAILSRTAWGWGEAGALITAATSTLWEGSPNKYWNSSTATSLCNIFRGSYLAGASLI
YTVTRNAGLVKRRGGGTGETLGEKWKARLNQMSALEFYSYKKSGITEVCREEARRALKDGVATGGH
AVSRGSAKLRWLVERGYLQPYGKVIDLGCGRGGWSYYAATIRKVQEVKGYTKGGPGHEEPMLVQSY
GWNIVRLKSGVDVFHMAAEPCDTLLCDIGESSSSPEVEEARTLRVLSMVGDWLEKRPGAFCIKVLCPY
TSTMMETLERLQRRYGGGLVRVPLSRNSTHEMYWVSGAKSNTIKSVSTTSQLLLGRMDGPRRPVKYE
EDVNLGSGTRAVVSCAEAPNMKIIGNRIERIRSEHAETWFFDENHPYRTWAYHGSYEAPTQGSASSLIN
GVVRLLSKPWDVVTGVTGIAMTDTTPYGQQRVFKEKVDTRVPDPQEGTRQVMSMVSSWLWKELGK
HKRPRVCTKEEFINKVRSNAALGAIFEEEKEWKTAVEAVNDPRFWALVDKEREHHLRGECQSCVYNM
MGKREKKQGEFGKAKGSRAIWYMWLGARFLEFEALGFLNEDHWMGRENSGGGVEGLGLQRLGYVL
EEMSRIPGGRMYADDTAGWDTRISRFDLENEALITNQMEKGHRALALAIIKYTYQNKVVKVLRPAEKG
KTVMDIISRQDQRGSGQVVTYALNTFTNLVVQLIRNMEAEEVLEMQDLWLLRRSEKVTNWLQSNGW
DRLKRMAVSGDDCVVKPIDDRFAHALRFLNDMGKVRKDTQEWKPSTGWDNWEEVPFCSHHFNKLHL
KDGRSIVVPCRHQDELIGRARVSPGAGWSIRETACLAKSYAQMWQLLYFHRRDLRLMANAICSSVPVD
WVPTGRTTWSIHGKGEWMTTEDMLVVWNRVWIEENDHMEDKTPVTKWTDIPYLGKREDLWCGSLIG
HRPRTTWAENIKNTVNMMRRIIGDEEKYVDYLSTQVRYLGEEGSTPGVL (SEQ ID NO:2

FIG. 8

SEQUENCE LISTING

<160> NUMBER OF SEQ ID NOS: 22

<210> SEQ ID NO 1
<211> LENGTH: 10804
<212> TYPE: DNA
<213> ORGANISM: Flavivirus

```
<220> FEATURE:
<221> NAME/KEY: CDS
<222> LOCATION: (108)..(10376)

<400> SEQUENCE: 1
```

| | | |
|---|---|---|
| agttgttgat ctgtgtgaat cagactgcga cagttcgagt ttgaagcgaa agctagcaac | | 60 |
| agtatcaaca ggttttattt tggatttgga aacgagagtt tctggtc atg aaa aac<br>                                                                                                                                                    Met Lys Asn<br>                                                                                                                                                     1 | | 116 |

| | |
|---|---|
| cca aag aag aaa tcc gga gga ttc cgg att gtc aat atg cta aaa cgc<br>Pro Lys Lys Lys Ser Gly Gly Phe Arg Ile Val Asn Met Leu Lys Arg<br>    5                    10                    15 | 164 |
| gga gta gcc cgt gtg agc ccc ttt ggg ggc ttg aag agg ctg cca gcc<br>Gly Val Ala Arg Val Ser Pro Phe Gly Gly Leu Lys Arg Leu Pro Ala<br>20                      25                    30                    35 | 212 |
| gga ctt ctg ctg ggt cat ggg ccc atc agg atg gtc ttg gcg att cta<br>Gly Leu Leu Leu Gly His Gly Pro Ile Arg Met Val Leu Ala Ile Leu<br>                  40                    45                    50 | 260 |
| gcc ttt ttg aga ttc acg gca atc aag cca tca ctg ggt ctc atc aat<br>Ala Phe Leu Arg Phe Thr Ala Ile Lys Pro Ser Leu Gly Leu Ile Asn<br>        55                    60                    65 | 308 |
| aga tgg ggt tca gtg ggg aaa aaa gag gct atg gaa ata ata aag aag<br>Arg Trp Gly Ser Val Gly Lys Lys Glu Ala Met Glu Ile Ile Lys Lys<br>    70                    75                    80 | 356 |
| ttt aag aaa gat ctg gct gcc atg ctg aga ata atc aat gct agg aag<br>Phe Lys Lys Asp Leu Ala Ala Met Leu Arg Ile Ile Asn Ala Arg Lys<br>85                      90                    95 | 404 |
| gag aag aag aga cga ggc aca gat act agt gtc gga att gtt ggc ctc<br>Glu Lys Lys Arg Arg Gly Thr Asp Thr Ser Val Gly Ile Val Gly Leu<br>100                   105                 110               115 | 452 |
| ctg ctg acc aca gcc atg gca gtg gag gtc act aga cgt ggg aat gca<br>Leu Leu Thr Thr Ala Met Ala Val Glu Val Thr Arg Arg Gly Asn Ala<br>                 120                 125               130 | 500 |
| tac tat atg tac ttg gac aga agc gat gct ggg gag gcc ata tct ttt<br>Tyr Tyr Met Tyr Leu Asp Arg Ser Asp Ala Gly Glu Ala Ile Ser Phe<br>               135                 140               145 | 548 |
| cca acc aca atg ggg atg aat aag tgt tat ata cag atc atg gat ctt<br>Pro Thr Thr Met Gly Met Asn Lys Cys Tyr Ile Gln Ile Met Asp Leu<br>       150                 155                 160 | 596 |
| gga cac atg tgt gat gcc acc atg agc tat gaa tgc cct atg ctg gat<br>Gly His Met Cys Asp Ala Thr Met Ser Tyr Glu Cys Pro Met Leu Asp<br>165                   170                 175 | 644 |
| gag ggg gta gaa cca gat gac gtc gat tgt tgg tgc aac acg acg tca<br>Glu Gly Val Glu Pro Asp Asp Val Asp Cys Trp Cys Asn Thr Thr Ser<br>180                   185                 190               195 | 692 |
| act tgg gtt gtg tac gga acc tgc cac cac aaa aaa ggt gaa gca cgg<br>Thr Trp Val Val Tyr Gly Thr Cys His His Lys Lys Gly Glu Ala Arg<br>               200                 205               210 | 740 |
| aga tct aga aga gct gtg acg ctc ccc tcc cat tcc act agg aag ctg<br>Arg Ser Arg Arg Ala Val Thr Leu Pro Ser His Ser Thr Arg Lys Leu<br>       215                 220                 225 | 788 |
| caa acg cgg tcg cag acc tgg ttg gaa tca aga gaa tac aca aag cac<br>Gln Thr Arg Ser Gln Thr Trp Leu Glu Ser Arg Glu Tyr Thr Lys His<br>230                   235                 240 | 836 |
| ctg att aga gtc gaa aat tgg ata ttc agg aac cct ggc ttc gcg tta<br>Leu Ile Arg Val Glu Asn Trp Ile Phe Arg Asn Pro Gly Phe Ala Leu<br>               245                 250               255 | 884 |
| gca gca gct gcc atc gct tgg ctt ttg gga agc tca acg agc caa aaa<br>Ala Ala Ala Ala Ile Ala Trp Leu Leu Gly Ser Ser Thr Ser Gln Lys<br>260                   265                 270               275 | 932 |

-continued

| | |
|---|---|
| gtc ata tac ttg gtc atg ata ctg ctg att gcc ccg gca tac agc atc<br>Val Ile Tyr Leu Val Met Ile Leu Leu Ile Ala Pro Ala Tyr Ser Ile<br>                      280                      285                  290 | 980 |
| agg tgc ata gga gtc agc aat agg gac ttt gtg gaa ggt atg tca ggt<br>Arg Cys Ile Gly Val Ser Asn Arg Asp Phe Val Glu Gly Met Ser Gly<br>             295                      300                      305 | 1028 |
| ggg act tgg gtt gat gtt gtc ttg gaa cat gga ggt tgt gtt acc gta<br>Gly Thr Trp Val Asp Val Val Leu Glu His Gly Gly Cys Val Thr Val<br>        310                      315                  320 | 1076 |
| atg gca cag gac aaa ccg act gtc gac ata gag ctg gtt aca aca aca<br>Met Ala Gln Asp Lys Pro Thr Val Asp Ile Glu Leu Val Thr Thr Thr<br>325                      330                      335 | 1124 |
| gtc agc aac atg gcg gag gta aga tcc tac tgc tat gag gca tca ata<br>Val Ser Asn Met Ala Glu Val Arg Ser Tyr Cys Tyr Glu Ala Ser Ile<br>340                      345                      350                  355 | 1172 |
| tcg gac atg gct tcg gac agc cgc tgc cca aca caa ggt gaa gcc tac<br>Ser Asp Met Ala Ser Asp Ser Arg Cys Pro Thr Gln Gly Glu Ala Tyr<br>                      360                      365                      370 | 1220 |
| ctt gac aag caa tca gac act caa tat gtc tgc aaa aga acg tta gtg<br>Leu Asp Lys Gln Ser Asp Thr Gln Tyr Val Cys Lys Arg Thr Leu Val<br>        375                      380                  385 | 1268 |
| gac aga ggc tgg gga aat gga tgt gga ctt ttt ggc aaa ggg agc ctg<br>Asp Arg Gly Trp Gly Asn Gly Cys Gly Leu Phe Gly Lys Gly Ser Leu<br>                      390                      395                      400 | 1316 |
| gtg aca tgc gct aag ttt gct tgc tct aag aaa atg acc ggg aag agc<br>Val Thr Cys Ala Lys Phe Ala Cys Ser Lys Lys Met Thr Gly Lys Ser<br>405                      410                      415 | 1364 |
| atc cag cca gag aat ctg gag tac cgg ata atg ctg tca gtt cat ggc<br>Ile Gln Pro Glu Asn Leu Glu Tyr Arg Ile Met Leu Ser Val His Gly<br>420                      425                      430                  435 | 1412 |
| tcc cag cac agt ggg atg atc gtt aat gat aca gga cat gaa act gat<br>Ser Gln His Ser Gly Met Ile Val Asn Asp Thr Gly His Glu Thr Asp<br>                      440                      445                  450 | 1460 |
| gag aat aga gcg aag gtt gag ata acg ccc aat tca cca aga gcc gaa<br>Glu Asn Arg Ala Lys Val Glu Ile Thr Pro Asn Ser Pro Arg Ala Glu<br>455                      460                      465 | 1508 |
| gcc acc ctg ggg ggt ttt gga agc cta gga ctt gat tgt gaa ccg agg<br>Ala Thr Leu Gly Gly Phe Gly Ser Leu Gly Leu Asp Cys Glu Pro Arg<br>        470                      475                  480 | 1556 |
| aca ggc ctt gac ttt tca gat ttg tat tac ttg act atg aat aac aag<br>Thr Gly Leu Asp Phe Ser Asp Leu Tyr Tyr Leu Thr Met Asn Asn Lys<br>485                      490                      495 | 1604 |
| cac tgg ttg gtt cac aag gag tgg ttc cac gac att cca tta cct tgg<br>His Trp Leu Val His Lys Glu Trp Phe His Asp Ile Pro Leu Pro Trp<br>500                      505                      510                  515 | 1652 |
| cac gct ggg gca gac acc gga act cca cac tgg aac aac aaa gaa gca<br>His Ala Gly Ala Asp Thr Gly Thr Pro His Trp Asn Asn Lys Glu Ala<br>                      520                      525                  530 | 1700 |
| ctg gta gag ttc aag gac gca cat gcc aaa agg cag act gtc gtg gtt<br>Leu Val Glu Phe Lys Asp Ala His Ala Lys Arg Gln Thr Val Val Val<br>        535                      540                  545 | 1748 |
| cta ggg agt caa gaa gga gca gtt cac acg gcc ctt gct gga gct ctg<br>Leu Gly Ser Gln Glu Gly Ala Val His Thr Ala Leu Ala Gly Ala Leu<br>                      550                      555                  560 | 1796 |
| gag gct gag atg gat ggt gca aag gga agg ctg tcc tct ggc cac ttg<br>Glu Ala Glu Met Asp Gly Ala Lys Gly Arg Leu Ser Ser Gly His Leu<br>565                      570                      575 | 1844 |
| aaa tgt cgc ctg aaa atg gac aaa ctt aga ttg aag ggc gtg tca tac<br>Lys Cys Arg Leu Lys Met Asp Lys Leu Arg Leu Lys Gly Val Ser Tyr<br>580                      585                      590                  595 | 1892 |

-continued

| | | |
|---|---|---|
| tcc ttg tgt acc gca gcg ttc aca ttc act aag atc ccg gct gaa aca<br>Ser Leu Cys Thr Ala Ala Phe Thr Phe Thr Lys Ile Pro Ala Glu Thr<br>600                            605                       610 | 1940 |
| ctg cac ggg aca gtc aca gtg gag gta cag tac gca ggg aca gat gga<br>Leu His Gly Thr Val Thr Val Glu Val Gln Tyr Ala Gly Thr Asp Gly<br>           615                       620                       625 | 1988 |
| cct tgc aag gtt cca gct cag atg gcg gtc gac atg caa act ctg acc<br>Pro Cys Lys Val Pro Ala Gln Met Ala Val Asp Met Gln Thr Leu Thr<br>630                         635                       640 | 2036 |
| cca gtt ggg agg ttg ata acc gct aac cct gta atc act gaa agc act<br>Pro Val Gly Arg Leu Ile Thr Ala Asn Pro Val Ile Thr Glu Ser Thr<br>645                         650                      655 | 2084 |
| gag aac tcc aag atg atg ctg gaa ctg gat cca cca ttt ggg gac tct<br>Glu Asn Ser Lys Met Met Leu Glu Leu Asp Pro Pro Phe Gly Asp Ser<br>660                   665                    670              675 | 2132 |
| tac att gtc ata gga gtc ggg gaa aag aag atc acc cac cac tgg cac<br>Tyr Ile Val Ile Gly Val Gly Glu Lys Lys Ile Thr His His Trp His<br>                  680                      685                 690 | 2180 |
| agg agt ggc agc acc att gga aaa gca ttt gaa gcc act gtg aga ggt<br>Arg Ser Gly Ser Thr Ile Gly Lys Ala Phe Glu Ala Thr Val Arg Gly<br>           695                       700                       705 | 2228 |
| gcc aag aga atg gca gtc ttg gga gac aca gcc tgg gac ttt gga tca<br>Ala Lys Arg Met Ala Val Leu Gly Asp Thr Ala Trp Asp Phe Gly Ser<br>710                         715                       720 | 2276 |
| gtt ggg ggt gct ctc aac tca ctg ggc aag ggc atc cat caa att ttt<br>Val Gly Gly Ala Leu Asn Ser Leu Gly Lys Gly Ile His Gln Ile Phe<br>725                         730                       735 | 2324 |
| gga gca gct ttc aaa tca ttg ttt gga gga atg tcc tgg ttc tca caa<br>Gly Ala Ala Phe Lys Ser Leu Phe Gly Gly Met Ser Trp Phe Ser Gln<br>740                         745                       750              755 | 2372 |
| att ctc att gga acg ttg ctg gtg tgg ttg ggt ctg aat aca aag aat<br>Ile Leu Ile Gly Thr Leu Leu Val Trp Leu Gly Leu Asn Thr Lys Asn<br>                  760                      765                 770 | 2420 |
| gga tct att tcc ctt atg tgc ttg gcc tta ggg gga gtg ttg atc ttc<br>Gly Ser Ile Ser Leu Met Cys Leu Ala Leu Gly Gly Val Leu Ile Phe<br>           775                       780                       785 | 2468 |
| tta tcc aca gcc gtc tct gct gat gtg ggg tgc tcg gtg gac ttc tca<br>Leu Ser Thr Ala Val Ser Ala Asp Val Gly Cys Ser Val Asp Phe Ser<br>790                         795                       800 | 2516 |
| aag aag gaa acg aga tgc ggt aca ggg gtg ttc gtc tat aac gac gtt<br>Lys Lys Glu Thr Arg Cys Gly Thr Gly Val Phe Val Tyr Asn Asp Val<br>805                         810                       815 | 2564 |
| gaa gct tgg agg gac agg tac aag tac cat cct gac tcc cct cgt aga<br>Glu Ala Trp Arg Asp Arg Tyr Lys Tyr His Pro Asp Ser Pro Arg Arg<br>820                         825                       830              835 | 2612 |
| ttg gca gca gca gtc aag caa gcc tgg gaa gat ggg atc tgt ggg atc<br>Leu Ala Ala Ala Val Lys Gln Ala Trp Glu Asp Gly Ile Cys Gly Ile<br>                  840                      845                 850 | 2660 |
| tcc tct gtt tca aga atg gaa aac atc atg tgg aga tca gta gaa ggg<br>Ser Ser Val Ser Arg Met Glu Asn Ile Met Trp Arg Ser Val Glu Gly<br>           855                       860                       865 | 2708 |
| gag ctc aac gca atc ctg gaa gag aat gga gtt caa ctg acg gtc gtt<br>Glu Leu Asn Ala Ile Leu Glu Glu Asn Gly Val Gln Leu Thr Val Val<br>870                         875                       880 | 2756 |
| gtg gga tct gta aaa aac ccc atg tgg aga ggt cca cag aga ttg ccc<br>Val Gly Ser Val Lys Asn Pro Met Trp Arg Gly Pro Gln Arg Leu Pro<br>885                         890                       895 | 2804 |
| gtg cct gtg aac gag ctg ccc cat ggc tgg aag gct tgg ggg aaa tcg<br>Val Pro Val Asn Glu Leu Pro His Gly Trp Lys Ala Trp Gly Lys Ser<br>900                         905                       910              915 | 2852 |

-continued

| | | |
|---|---|---|
| tac ttc gtc agg gca gca aag aca aat aac agc ttt gtc gtg gat ggt<br>Tyr Phe Val Arg Ala Ala Lys Thr Asn Asn Ser Phe Val Val Asp Gly<br>              920              925              930 | 2900 |
| gac aca ctg aag gaa tgc cca ctc aaa cat aga gca tgg aac agc ttt<br>Asp Thr Leu Lys Glu Cys Pro Leu Lys His Arg Ala Trp Asn Ser Phe<br>              935              940              945 | 2948 |
| ctt gtg gag gat cat ggg ttc ggg gta ttt cac act agt gtc tgg ctc<br>Leu Val Glu Asp His Gly Phe Gly Val Phe His Thr Ser Val Trp Leu<br>              950              955              960 | 2996 |
| aag gtt aga gaa gat tat tca tta gag tgt gat cca gcc gtc att gga<br>Lys Val Arg Glu Asp Tyr Ser Leu Glu Cys Asp Pro Ala Val Ile Gly<br>              965              970              975 | 3044 |
| aca gcc gct aag gga aag gag gct gtg cac agt gat cta ggc tac tgg<br>Thr Ala Ala Lys Gly Lys Glu Ala Val His Ser Asp Leu Gly Tyr Trp<br>980                  985              990              995 | 3092 |
| att gag agt gag aag aac gac aca tgg agg ctg aag agg gcc cac<br>Ile Glu Ser Glu Lys Asn Asp Thr Trp Arg Leu Lys Arg Ala His<br>            1000             1005             1010 | 3137 |
| ctg atc gag atg aaa aca tgt gaa tgg cca aag tcc cac aca ttg<br>Leu Ile Glu Met Lys Thr Cys Glu Trp Pro Lys Ser His Thr Leu<br>            1015             1020             1025 | 3182 |
| tgg aca gat gga ata gaa gaa agt gat ctg atc ata ccc aag tct<br>Trp Thr Asp Gly Ile Glu Glu Ser Asp Leu Ile Ile Pro Lys Ser<br>            1030             1035             1040 | 3227 |
| tta gct ggg cca ctc agc cat cac aac acc aga gag ggc tac agg<br>Leu Ala Gly Pro Leu Ser His His Asn Thr Arg Glu Gly Tyr Arg<br>            1045             1050             1055 | 3272 |
| acc caa atg gaa ggg cca tgg cat agt gaa gag ctt gaa att cgg<br>Thr Gln Met Glu Gly Pro Trp His Ser Glu Glu Leu Glu Ile Arg<br>            1060             1065             1070 | 3317 |
| ttt gag gaa tgc cca ggc act aag gtc cac gtg gag gaa aca tgt<br>Phe Glu Glu Cys Pro Gly Thr Lys Val His Val Glu Glu Thr Cys<br>            1075             1080             1085 | 3362 |
| gga aca aga gga cca tct ctg aga tca acc act gca agc gga agg<br>Gly Thr Arg Gly Pro Ser Leu Arg Ser Thr Thr Ala Ser Gly Arg<br>            1090             1095             1100 | 3407 |
| gtg atc gag gaa tgg tgc tgc agg gag tgc aca atg ccc cca ctg<br>Val Ile Glu Glu Trp Cys Cys Arg Glu Cys Thr Met Pro Pro Leu<br>            1105             1110             1115 | 3452 |
| tcg ttc cgg gct aaa gat ggt tgt tgg tat gga atg gag ata agg<br>Ser Phe Arg Ala Lys Asp Gly Cys Trp Tyr Gly Met Glu Ile Arg<br>            1120             1125             1130 | 3497 |
| ccc agg aaa gaa cca gaa agt aac tta gta agg tca atg gtg act<br>Pro Arg Lys Glu Pro Glu Ser Asn Leu Val Arg Ser Met Val Thr<br>            1135             1140             1145 | 3542 |
| gca gga tca act gat cac atg gat cac ttc tcc ctt gga gtg ctt<br>Ala Gly Ser Thr Asp His Met Asp His Phe Ser Leu Gly Val Leu<br>            1150             1155             1160 | 3587 |
| gtg att ctg ctc atg gta cag gaa ggg cta aag aag aga atg acc<br>Val Ile Leu Leu Met Val Gln Glu Gly Leu Lys Lys Arg Met Thr<br>            1165             1170             1175 | 3632 |
| aca aag atc atc ata agc aca tca atg gca gtg ctg gta gct atg<br>Thr Lys Ile Ile Ile Ser Thr Ser Met Ala Val Leu Val Ala Met<br>            1180             1185             1190 | 3677 |
| atc ctg gga gga ttt tca atg agt gac ctg gct aag ctt gca att<br>Ile Leu Gly Gly Phe Ser Met Ser Asp Leu Ala Lys Leu Ala Ile<br>            1195             1200             1205 | 3722 |
| ttg atg ggt gcc acc ttc gcg gaa atg aac act gga gga gat gtt<br>Leu Met Gly Ala Thr Phe Ala Glu Met Asn Thr Gly Gly Asp Val<br>            1210             1215             1220 | 3767 |

```
gct cat ctg gcg ctg ata gcg gca ttc aaa gtc aga cct gcg ttg        3812
Ala His Leu Ala Leu Ile Ala Ala Phe Lys Val Arg Pro Ala Leu
        1225                1230                1235 ctg gta tct ttc att ttc aga gct aat tgg aca ccc gtg gag agc        3857
Leu Val Ser Phe Ile Phe Arg Ala Asn Trp Thr Pro Arg Glu Ser
            1240                1245                1250 atg ctg ctg gcc ttg gcc tcg tgt ctt ctg caa act gcg atc tcc        3902
Met Leu Leu Ala Leu Ala Ser Cys Leu Leu Gln Thr Ala Ile Ser
                1255                1260                1265 gcc ttg gaa ggc gac ctg atg gtt ccc atc aat ggt ttt gct ttg        3947
Ala Leu Glu Gly Asp Leu Met Val Pro Ile Asn Gly Phe Ala Leu
                    1270                1275                1280 gcc tgg ttg gca ata cga gcg atg gtt gtt cca cgc act gac aac        3992
Ala Trp Leu Ala Ile Arg Ala Met Val Val Pro Arg Thr Asp Asn
                        1285                1290                1295 atc acc ttg gca atc ctg gct gct ctg aca cca ctg gcc cgg ggc        4037
Ile Thr Leu Ala Ile Leu Ala Ala Leu Thr Pro Leu Ala Arg Gly
            1300                1305                1310 aca ctg ctt gtg gcg tgg aga gca ggc ctt gct act tgc ggg ggg        4082
Thr Leu Leu Val Ala Trp Arg Ala Gly Leu Ala Thr Cys Gly Gly
                1315                1320                1325 ttc atg ctc ctt tct ctg aag ggg aaa ggc agt gtg aag aag aac        4127
Phe Met Leu Leu Ser Leu Lys Gly Lys Gly Ser Val Lys Lys Asn
                    1330                1335                1340 tta cca ttt gtc atg gcc ctg gga cta acc gct gtg agg ctg gtc        4172
Leu Pro Phe Val Met Ala Leu Gly Leu Thr Ala Val Arg Leu Val
                        1345                1350                1355 gac ccc atc aac gtg gtg gga ctg ctg ttg ctc aca agg agt ggg        4217
Asp Pro Ile Asn Val Val Gly Leu Leu Leu Leu Thr Arg Ser Gly
            1360                1365                1370 aag cgg agc tgg ccc cct agt gaa gta ctc aca gct gtt ggc ctg        4262
Lys Arg Ser Trp Pro Pro Ser Glu Val Leu Thr Ala Val Gly Leu
                1375                1380                1385 ata tgc gca ttg gct gga ggg ttc gcc aag gcg gat ata gag atg        4307
Ile Cys Ala Leu Ala Gly Gly Phe Ala Lys Ala Asp Ile Glu Met
                    1390                1395                1400 gct ggg ccc atg gcc gcg gtc ggt ctg cta att gtc agt tac gtg        4352
Ala Gly Pro Met Ala Ala Val Gly Leu Leu Ile Val Ser Tyr Val
                        1405                1410                1415 gtc tca gga aag agt gtg gac atg tac att gaa aga gca ggt gac        4397
Val Ser Gly Lys Ser Val Asp Met Tyr Ile Glu Arg Ala Gly Asp
            1420                1425                1430 atc aca tgg gaa aaa gat gcg gaa gtc act gga aac agt ccc cgg        4442
Ile Thr Trp Glu Lys Asp Ala Glu Val Thr Gly Asn Ser Pro Arg
                1435                1440                1445 ctc gat gtg gca cta gat gag agt ggt gat ttc tcc cta gtg gag        4487
Leu Asp Val Ala Leu Asp Glu Ser Gly Asp Phe Ser Leu Val Glu
                    1450                1455                1460 gat gat ggt ccc ccc atg aga gag atc ata ctc aaa gtg gtc ctg        4532
Asp Asp Gly Pro Pro Met Arg Glu Ile Ile Leu Lys Val Val Leu
                        1465                1470                1475 atg gcc atc tgt ggc atg aac cca ata gcc ata ccc ttt gca gct        4577
Met Ala Ile Cys Gly Met Asn Pro Ile Ala Ile Pro Phe Ala Ala
            1480                1485                1490 gga gcg tgg tac gtg tat gtg aag act gga aaa agg agt ggt gct        4622
Gly Ala Trp Tyr Val Tyr Val Lys Thr Gly Lys Arg Ser Gly Ala
                1495                1500                1505 cta tgg gat gtg cct gct ccc aag gaa gta aaa aag ggg gag acc        4667
Leu Trp Asp Val Pro Ala Pro Lys Glu Val Lys Lys Gly Glu Thr
                    1510                1515                1520
```

| | | |
|---|---|---|
| aca gat gga gtg tac aga gta atg act cgt aga ctg cta ggt tca<br>Thr Asp Gly Val Tyr Arg Val Met Thr Arg Arg Leu Leu Gly Ser<br>1525 1530 1535 | | 4712 |
| aca caa gtt gga gtg gga gtc atg caa gag ggg gtc ttc cac act<br>Thr Gln Val Gly Val Gly Val Met Gln Glu Gly Val Phe His Thr<br>1540 1545 1550 | | 4757 |
| atg tgg cac gtc aca aaa gga tcc gcg ctg aga agc ggt gaa ggg<br>Met Trp His Val Thr Lys Gly Ser Ala Leu Arg Ser Gly Glu Gly<br>1555 1560 1565 | | 4802 |
| aga ctt gat cca tac tgg gga gat gtc aag cag gat ctg gtg tca<br>Arg Leu Asp Pro Tyr Trp Gly Asp Val Lys Gln Asp Leu Val Ser<br>1570 1575 1580 | | 4847 |
| tac tgt ggt cca tgg aag cta gat gcc gcc tgg gac ggg cac agc<br>Tyr Cys Gly Pro Trp Lys Leu Asp Ala Ala Trp Asp Gly His Ser<br>1585 1590 1595 | | 4892 |
| gag gtg cag ctc ttg gcc gtg ccc ccc gga gag aga gcg agg aac<br>Glu Val Gln Leu Leu Ala Val Pro Pro Gly Glu Arg Ala Arg Asn<br>1600 1605 1610 | | 4937 |
| atc cag act ctg ccc gga ata ttt aag aca aag gat ggg gac att<br>Ile Gln Thr Leu Pro Gly Ile Phe Lys Thr Lys Asp Gly Asp Ile<br>1615 1620 1625 | | 4982 |
| gga gca gtt gcg ctg gac tac cca gca gga act tca gga tct cca<br>Gly Ala Val Ala Leu Asp Tyr Pro Ala Gly Thr Ser Gly Ser Pro<br>1630 1635 1640 | | 5027 |
| atc cta gat aag tgt ggg aga gtg ata gga ctc tat ggt aat ggg<br>Ile Leu Asp Lys Cys Gly Arg Val Ile Gly Leu Tyr Gly Asn Gly<br>1645 1650 1655 | | 5072 |
| gtc gtg atc aaa aat ggg agt tac gtt agt gcc atc acc caa ggg<br>Val Val Ile Lys Asn Gly Ser Tyr Val Ser Ala Ile Thr Gln Gly<br>1660 1665 1670 | | 5117 |
| agg agg gag gaa gag act cct gtt gag tgc ttc gag cct tcg atg<br>Arg Arg Glu Glu Glu Thr Pro Val Glu Cys Phe Glu Pro Ser Met<br>1675 1680 1685 | | 5162 |
| ctg aag aag aag cag cta act gtc tta gac ttg cat cct gga gct<br>Leu Lys Lys Lys Gln Leu Thr Val Leu Asp Leu His Pro Gly Ala<br>1690 1695 1700 | | 5207 |
| ggg aaa acc agg aga gtt ctt cct gaa ata gtc cgt gaa gcc ata<br>Gly Lys Thr Arg Arg Val Leu Pro Glu Ile Val Arg Glu Ala Ile<br>1705 1710 1715 | | 5252 |
| aaa aca aga ctc cgc act gtg atc tta gct cca acc agg gtt gtc<br>Lys Thr Arg Leu Arg Thr Val Ile Leu Ala Pro Thr Arg Val Val<br>1720 1725 1730 | | 5297 |
| gct gct gaa atg gag gaa gcc ctt aga ggg ctt cca gtg cgt tat<br>Ala Ala Glu Met Glu Glu Ala Leu Arg Gly Leu Pro Val Arg Tyr<br>1735 1740 1745 | | 5342 |
| atg aca aca gca gtc aat gtc acc cat tct ggg aca gaa atc gtt<br>Met Thr Thr Ala Val Asn Val Thr His Ser Gly Thr Glu Ile Val<br>1750 1755 1760 | | 5387 |
| gac tta atg tgc cat gcc acc ttc act tca cgt cta cta cag cca<br>Asp Leu Met Cys His Ala Thr Phe Thr Ser Arg Leu Leu Gln Pro<br>1765 1770 1775 | | 5432 |
| atc aga gtc ccc aac tat aat ctg tat att atg gat gag gcc cac<br>Ile Arg Val Pro Asn Tyr Asn Leu Tyr Ile Met Asp Glu Ala His<br>1780 1785 1790 | | 5477 |
| ttc aca gat ccc tca agt ata gca gca aga gga tac att tca aca<br>Phe Thr Asp Pro Ser Ser Ile Ala Ala Arg Gly Tyr Ile Ser Thr<br>1795 1800 1805 | | 5522 |
| agg gtt gag atg ggc gag gcg gct gcc atc ttc atg act gcc acg<br>Arg Val Glu Met Gly Glu Ala Ala Ala Ile Phe Met Thr Ala Thr<br>1810 1815 1820 | | 5567 |

```
cca cca gga acc cgt gac gca ttc ccg gac tcc aac tca cca att        5612
Pro Pro Gly Thr Arg Asp Ala Phe Pro Asp Ser Asn Ser Pro Ile
                1825                1830                1835 atg gac acc gaa gtg gaa gtc cca gag aga gcc tgg agc tca ggc        5657
Met Asp Thr Glu Val Glu Val Pro Glu Arg Ala Trp Ser Ser Gly
                1840                1845                1850 ttt gat tgg gtg acg gat cat tct gga aaa aca gtt tgg ttt gtt        5702
Phe Asp Trp Val Thr Asp His Ser Gly Lys Thr Val Trp Phe Val
                1855                1860                1865 cca agc gtg agg aat ggc aat gag atc gca gct tgt ctg aca aag        5747
Pro Ser Val Arg Asn Gly Asn Glu Ile Ala Ala Cys Leu Thr Lys
                1870                1875                1880 gct gga aaa cgg gtc ata cag ctc agc aga aag act ttt gag aca        5792
Ala Gly Lys Arg Val Ile Gln Leu Ser Arg Lys Thr Phe Glu Thr
                1885                1890                1895 gag ttc cag aaa aca aaa cat caa gag tgg gac ttc gtc gtg aca        5837
Glu Phe Gln Lys Thr Lys His Gln Glu Trp Asp Phe Val Val Thr
                1900                1905                1910 act gac att tca gag atg ggc gcc aac ttt aaa gct gac cgt gtc        5882
Thr Asp Ile Ser Glu Met Gly Ala Asn Phe Lys Ala Asp Arg Val
                1915                1920                1925 ata gat tcc agg aga tgc cta aag ccg gtc ata ctt gat ggc gag        5927
Ile Asp Ser Arg Arg Cys Leu Lys Pro Val Ile Leu Asp Gly Glu
                1930                1935                1940 aga gtc att ctg gct gga ccc atg cct gtc aca cat gcc agc gct        5972
Arg Val Ile Leu Ala Gly Pro Met Pro Val Thr His Ala Ser Ala
                1945                1950                1955 gcc cag agg agg ggg cgc ata ggc agg aac ccc aac aaa cct gga        6017
Ala Gln Arg Arg Gly Arg Ile Gly Arg Asn Pro Asn Lys Pro Gly
                1960                1965                1970 gat gag tat ctg tat gga ggt ggg tgc gca gag act gat gaa gac        6062
Asp Glu Tyr Leu Tyr Gly Gly Gly Cys Ala Glu Thr Asp Glu Asp
                1975                1980                1985 cat gca cac tgg ctt gaa gca aga atg ctt ctt gac aac att tac        6107
His Ala His Trp Leu Glu Ala Arg Met Leu Leu Asp Asn Ile Tyr
                1990                1995                2000 ctc caa gat ggc ctc ata gcc tcg ctc tat cga cct gag gcc gac        6152
Leu Gln Asp Gly Leu Ile Ala Ser Leu Tyr Arg Pro Glu Ala Asp
                2005                2010                2015 aaa gta gca gct att gag gga gag ttc aag ctt agg acg gag caa        6197
Lys Val Ala Ala Ile Glu Gly Glu Phe Lys Leu Arg Thr Glu Gln
                2020                2025                2030 agg aag acc ttt gtg gaa ctc atg aaa aga gga gat ctt cct gtt        6242
Arg Lys Thr Phe Val Glu Leu Met Lys Arg Gly Asp Leu Pro Val
                2035                2040                2045 tgg ctg gcc tat cag gtt gca tct gcc gga ata acc tac aca gat        6287
Trp Leu Ala Tyr Gln Val Ala Ser Ala Gly Ile Thr Tyr Thr Asp
                2050                2055                2060 aga aga tgg tgc ttt gat ggc acg acc aac aac acc ata atg gaa        6332
Arg Arg Trp Cys Phe Asp Gly Thr Thr Asn Asn Thr Ile Met Glu
                2065                2070                2075 gac agt gtg ccg gca gag gtg tgg acc aga tac gga gag aaa aga        6377
Asp Ser Val Pro Ala Glu Val Trp Thr Arg Tyr Gly Glu Lys Arg
                2080                2085                2090 gtg ctc aaa ccg agg tgg atg gac gcc aga gtt tgt tca gat cat        6422
Val Leu Lys Pro Arg Trp Met Asp Ala Arg Val Cys Ser Asp His
                2095                2100                2105 gcg gcc ctg aag tca ttc aaa gag ttt gcc gct ggg aaa aga gga        6467
Ala Ala Leu Lys Ser Phe Lys Glu Phe Ala Ala Gly Lys Arg Gly
                2110                2115                2120
```

| | | | | | | | | | | | | |
|---|---|---|---|---|---|---|---|---|---|---|---|---|
| gcg | gcc | ttt | gga | gtg | atg | gaa | gcc | ctg | gga | aca | ctg | cca | gga | cat | 6512 |
| Ala | Ala | Phe | Gly | Val | Met | Glu | Ala | Leu | Gly | Thr | Leu | Pro | Gly | His | |
| | | | 2125 | | | | 2130 | | | | 2135 | | | | | atg aca gag aga ttc cag gag gcc att gac aac ctc gct gtg ctc    6557
Met Thr Glu Arg Phe Gln Glu Ala Ile Asp Asn Leu Ala Val Leu
            2140            2145            2150 atg cgg gca gag act gga agc agg ccc tac aaa gcc gcg gcg gcc    6602
Met Arg Ala Glu Thr Gly Ser Arg Pro Tyr Lys Ala Ala Ala Ala
            2155            2160            2165 caa tta ccg gag acc cta gag act atc atg ctt ttg ggg ttg ctg    6647
Gln Leu Pro Glu Thr Leu Glu Thr Ile Met Leu Leu Gly Leu Leu
            2170            2175            2180 gga aca gtc tcg ctg gga atc ttt ttc gtc ttg atg cgg aac aag    6692
Gly Thr Val Ser Leu Gly Ile Phe Phe Val Leu Met Arg Asn Lys
            2185            2190            2195 ggc ata ggg aag atg ggc ttt gga atg gtg act ctt ggg gcc agc    6737
Gly Ile Gly Lys Met Gly Phe Gly Met Val Thr Leu Gly Ala Ser
            2200            2205            2210 gca tgg ctt atg tgg ctc tcg gaa att gag cca gcc aga att gca    6782
Ala Trp Leu Met Trp Leu Ser Glu Ile Glu Pro Ala Arg Ile Ala
            2215            2220            2225 tgt gtc ctc att gtt gtg ttc cta ttg ctg gtg gtg ctc ata cct    6827
Cys Val Leu Ile Val Val Phe Leu Leu Leu Val Val Leu Ile Pro
            2230            2235            2240 gag cca gaa aag caa aga tct ccc cag gac aac caa atg gca atc    6872
Glu Pro Glu Lys Gln Arg Ser Pro Gln Asp Asn Gln Met Ala Ile
            2245            2250            2255 atc atc atg gta gca gtg ggt ctt ctg ggc ttg att acc gcc aat    6917
Ile Ile Met Val Ala Val Gly Leu Leu Gly Leu Ile Thr Ala Asn
            2260            2265            2270 gaa ctc gga tgg ttg gag aga aca aag agt gac cta agc cat cta    6962
Glu Leu Gly Trp Leu Glu Arg Thr Lys Ser Asp Leu Ser His Leu
            2275            2280            2285 atg gga agg aga gag gag ggg gca act ata gga ttc tca atg gac    7007
Met Gly Arg Arg Glu Glu Gly Ala Thr Ile Gly Phe Ser Met Asp
            2290            2295            2300 att gac ctg cgg cca gcc tca gct tgg gct atc tat gct gct ctg    7052
Ile Asp Leu Arg Pro Ala Ser Ala Trp Ala Ile Tyr Ala Ala Leu
            2305            2310            2315 aca act ttc att acc cca gcc gtc caa cat gca gtg acc act tca    7097
Thr Thr Phe Ile Thr Pro Ala Val Gln His Ala Val Thr Thr Ser
            2320            2325            2330 tac aac aac tac tcc tta atg gcg atg gcc acg caa gct gga gtg    7142
Tyr Asn Asn Tyr Ser Leu Met Ala Met Ala Thr Gln Ala Gly Val
            2335            2340            2345 ttg ttc ggt atg ggt aaa ggg atg cca ttc tat gca tgg gac ttt    7187
Leu Phe Gly Met Gly Lys Gly Met Pro Phe Tyr Ala Trp Asp Phe
            2350            2355            2360 gga gtc ccg ctg cta atg ata ggt tgc tac tca caa tta aca ccc    7232
Gly Val Pro Leu Leu Met Ile Gly Cys Tyr Ser Gln Leu Thr Pro
            2365            2370            2375 ctg acc cta ata gtg gcc atc att ttg ctc gtg gcg cac tac atg    7277
Leu Thr Leu Ile Val Ala Ile Ile Leu Leu Val Ala His Tyr Met
            2380            2385            2390 tac ttg atc cca ggg ctg cag gca gca gct gcg cgt gct gcc cag    7322
Tyr Leu Ile Pro Gly Leu Gln Ala Ala Ala Ala Arg Ala Ala Gln
            2395            2400            2405 aag aga acg gca gct ggc atc atg aag aac cct gtt gtg gat gga    7367
Lys Arg Thr Ala Ala Gly Ile Met Lys Asn Pro Val Val Asp Gly
            2410            2415            2420

| | |
|---|---|
| ata gtg gtg act gac att gac aca atg aca att gac ccc caa gtg<br>Ile Val Val Thr Asp Ile Asp Thr Met Thr Ile Asp Pro Gln Val<br>                       2425                        2430                       2435 | 7412 |
| gag aaa aag atg gga cag gtg cta ctc ata gca gta gct gtc tcc<br>Glu Lys Lys Met Gly Gln Val Leu Leu Ile Ala Val Ala Val Ser<br>                       2440                        2445                      2450 | 7457 |
| agc gcc ata ctg tcg cgg acc gcc tgg ggg tgg ggt gag gct ggg<br>Ser Ala Ile Leu Ser Arg Thr Ala Trp Gly Trp Gly Glu Ala Gly<br>                       2455                        2460                      2465 | 7502 |
| gcc ctg atc aca gct gca act tcc act ttg tgg gag ggc tct ccg<br>Ala Leu Ile Thr Ala Ala Thr Ser Thr Leu Trp Glu Gly Ser Pro<br>                       2470                        2475                      2480 | 7547 |
| aac aag tac tgg aac tcc tcc aca gcc acc tca ctg tgt aac att<br>Asn Lys Tyr Trp Asn Ser Ser Thr Ala Thr Ser Leu Cys Asn Ile<br>                       2485                        2490                      2495 | 7592 |
| ttt agg gga agc tac ttg gct gga gct tct cta atc tac aca gta<br>Phe Arg Gly Ser Tyr Leu Ala Gly Ala Ser Leu Ile Tyr Thr Val<br>                       2500                        2505                      2510 | 7637 |
| aca aga aac gct ggc ttg gtc aag aga cgt ggg ggt gga acg gga<br>Thr Arg Asn Ala Gly Leu Val Lys Arg Arg Gly Gly Gly Thr Gly<br>                       2515                        2520                      2525 | 7682 |
| gag acc ctg gga gag aaa tgg aag gcc cgc ctg aac cag atg tcg<br>Glu Thr Leu Gly Glu Lys Trp Lys Ala Arg Leu Asn Gln Met Ser<br>                       2530                        2535                      2540 | 7727 |
| gcc ctg gag ttc tac tcc tac aaa aag tca ggc atc acc gag gtg<br>Ala Leu Glu Phe Tyr Ser Tyr Lys Lys Ser Gly Ile Thr Glu Val<br>                       2545                        2550                      2555 | 7772 |
| tgc aga gaa gag gcc cgc cgc gcc ctc aag gac ggt gtg gca acg<br>Cys Arg Glu Glu Ala Arg Arg Ala Leu Lys Asp Gly Val Ala Thr<br>                       2560                        2565                      2570 | 7817 |
| gga ggc cac gct gtg tcc cga gga agt gca aag ctg aga tgg ttg<br>Gly Gly His Ala Val Ser Arg Gly Ser Ala Lys Leu Arg Trp Leu<br>                       2575                        2580                      2585 | 7862 |
| gtg gag agg gga tac ctg cag ccc tat gga aag gtc att gat ctt<br>Val Glu Arg Gly Tyr Leu Gln Pro Tyr Gly Lys Val Ile Asp Leu<br>                       2590                        2595                      2600 | 7907 |
| gga tgt ggc aga ggg ggc tgg agt tac tat gcc gcc acc atc cgc<br>Gly Cys Gly Arg Gly Gly Trp Ser Tyr Tyr Ala Ala Thr Ile Arg<br>                       2605                        2610                      2615 | 7952 |
| aaa gtt caa gaa gtg aaa gga tac aca aaa gga ggc cct ggt cat<br>Lys Val Gln Glu Val Lys Gly Tyr Thr Lys Gly Gly Pro Gly His<br>                       2620                        2625                      2630 | 7997 |
| gaa gaa ccc atg ttg gtg caa agc tat ggg tgg aac ata gtc cgt<br>Glu Glu Pro Met Leu Val Gln Ser Tyr Gly Trp Asn Ile Val Arg<br>                       2635                        2640                      2645 | 8042 |
| ctt aag agt ggg gtg gac gtc ttt cat atg gcg gct gag ccg tgt<br>Leu Lys Ser Gly Val Asp Val Phe His Met Ala Ala Glu Pro Cys<br>                       2650                        2655                      2660 | 8087 |
| gac acg ttg ctg tgt gat ata ggt gag tca tca tct agt cct gaa<br>Asp Thr Leu Leu Cys Asp Ile Gly Glu Ser Ser Ser Ser Pro Glu<br>                       2665                        2670                      2675 | 8132 |
| gtg gaa gaa gca cgg acg ctc aga gtc ctc tcc atg gtg ggg gat<br>Val Glu Glu Ala Arg Thr Leu Arg Val Leu Ser Met Val Gly Asp<br>                       2680                        2685                      2690 | 8177 |
| tgg ctt gaa aaa aga cca gga gcc ttt tgt ata aaa gtg ttg tgc<br>Trp Leu Glu Lys Arg Pro Gly Ala Phe Cys Ile Lys Val Leu Cys<br>                       2695                        2700                      2705 | 8222 |
| cca tac acc agc act atg atg gaa acc ctg gag cga ctg cag cgt<br>Pro Tyr Thr Ser Thr Met Met Glu Thr Leu Glu Arg Leu Gln Arg<br>                       2710                        2715                      2720 | 8267 |

| | | | | | | | | | | | | |
|---|---|---|---|---|---|---|---|---|---|---|---|---|
| agg | tat | ggg | gga | gga | ctg | gtc | aga | gtg | cca | ctc | tcc | cgc | aac | tct | 8312 |
| Arg | Tyr | Gly | Gly | Gly | Leu | Val | Arg | Val | Pro | Leu | Ser | Arg | Asn | Ser |
| | | | 2725 | | | | 2730 | | | | | 2735 |

| aca | cat | gag | atg | tac | tgg | gtc | tct | gga | gcg | aaa | agc | aac | acc | ata | 8357 |
| Thr | His | Glu | Met | Tyr | Trp | Val | Ser | Gly | Ala | Lys | Ser | Asn | Thr | Ile |
| | | | 2740 | | | | 2745 | | | | | 2750 |

| aaa | agt | gtg | tcc | acc | acg | agc | cag | ctc | ctt | ttg | ggg | cgc | atg | gac | 8402 |
| Lys | Ser | Val | Ser | Thr | Thr | Ser | Gln | Leu | Leu | Leu | Gly | Arg | Met | Asp |
| | | | 2755 | | | | 2760 | | | | | 2765 |

| ggg | ccc | agg | agg | cca | gtg | aaa | tat | gaa | gag | gat | gtg | aat | ctc | ggc | 8447 |
| Gly | Pro | Arg | Arg | Pro | Val | Lys | Tyr | Glu | Glu | Asp | Val | Asn | Leu | Gly |
| | | | 2770 | | | | 2775 | | | | | 2780 |

| tct | ggc | acg | cgg | gct | gtg | gta | agc | tgc | gct | gaa | gct | ccc | aac | atg | 8492 |
| Ser | Gly | Thr | Arg | Ala | Val | Val | Ser | Cys | Ala | Glu | Ala | Pro | Asn | Met |
| | | | 2785 | | | | 2790 | | | | | 2795 |

| aag | atc | att | ggt | aac | cgc | att | gag | agg | atc | cgc | agt | gag | cac | gcg | 8537 |
| Lys | Ile | Ile | Gly | Asn | Arg | Ile | Glu | Arg | Ile | Arg | Ser | Glu | His | Ala |
| | | | 2800 | | | | 2805 | | | | | 2810 |

| gaa | acg | tgg | ttc | ttt | gac | gag | aac | cac | cca | tat | agg | aca | tgg | gct | 8582 |
| Glu | Thr | Trp | Phe | Phe | Asp | Glu | Asn | His | Pro | Tyr | Arg | Thr | Trp | Ala |
| | | | 2815 | | | | 2820 | | | | | 2825 |

| tac | cat | gga | agc | tac | gag | gcc | ccc | aca | caa | ggg | tca | gcg | tcc | tct | 8627 |
| Tyr | His | Gly | Ser | Tyr | Glu | Ala | Pro | Thr | Gln | Gly | Ser | Ala | Ser | Ser |
| | | | 2830 | | | | 2835 | | | | | 2840 |

| cta | ata | aac | ggg | gtt | gtc | agg | ctc | ctg | tca | aaa | ccc | tgg | gat | gtg | 8672 |
| Leu | Ile | Asn | Gly | Val | Val | Arg | Leu | Leu | Ser | Lys | Pro | Trp | Asp | Val |
| | | | 2845 | | | | 2850 | | | | | 2855 |

| gtg | act | gga | gtc | aca | gga | ata | gcc | atg | acc | gac | acc | aca | ccg | tat | 8717 |
| Val | Thr | Gly | Val | Thr | Gly | Ile | Ala | Met | Thr | Asp | Thr | Thr | Pro | Tyr |
| | | | 2860 | | | | 2865 | | | | | 2870 |

| ggt | cag | caa | aga | gtt | ttc | aag | gaa | aaa | gtg | gac | act | agg | gtg | cca | 8762 |
| Gly | Gln | Gln | Arg | Val | Phe | Lys | Glu | Lys | Val | Asp | Thr | Arg | Val | Pro |
| | | | 2875 | | | | 2880 | | | | | 2885 |

| gac | ccc | caa | gaa | ggc | act | cgt | cag | gtt | atg | agc | atg | gtc | tct | tcc | 8807 |
| Asp | Pro | Gln | Glu | Gly | Thr | Arg | Gln | Val | Met | Ser | Met | Val | Ser | Ser |
| | | | 2890 | | | | 2895 | | | | | 2900 |

| tgg | ttg | tgg | aaa | gag | tta | ggc | aaa | cac | aaa | cgg | cca | cga | gtc | tgt | 8852 |
| Trp | Leu | Trp | Lys | Glu | Leu | Gly | Lys | His | Lys | Arg | Pro | Arg | Val | Cys |
| | | | 2905 | | | | 2910 | | | | | 2915 |

| acc | aaa | gaa | gag | ttc | atc | aac | aag | gtt | cgt | agc | aac | gca | gca | tta | 8897 |
| Thr | Lys | Glu | Glu | Phe | Ile | Asn | Lys | Val | Arg | Ser | Asn | Ala | Ala | Leu |
| | | | 2920 | | | | 2925 | | | | | 2930 |

| ggg | gca | ata | ttt | gaa | gag | gaa | aaa | gag | tgg | aag | act | gca | gtg | gaa | 8942 |
| Gly | Ala | Ile | Phe | Glu | Glu | Glu | Lys | Glu | Trp | Lys | Thr | Ala | Val | Glu |
| | | | 2935 | | | | 2940 | | | | | 2945 |

| gct | gtg | aac | gat | cca | agg | ttc | tgg | gct | cta | gtg | gac | aag | gaa | aga | 8987 |
| Ala | Val | Asn | Asp | Pro | Arg | Phe | Trp | Ala | Leu | Val | Asp | Lys | Glu | Arg |
| | | | 2950 | | | | 2955 | | | | | 2960 |

| gag | cac | cac | ctg | aga | gga | gag | tgc | cag | agc | tgt | gtg | tac | aac | atg | 9032 |
| Glu | His | His | Leu | Arg | Gly | Glu | Cys | Gln | Ser | Cys | Val | Tyr | Asn | Met |
| | | | 2965 | | | | 2970 | | | | | 2975 |

| atg | gga | aaa | aga | gaa | aag | aaa | caa | ggg | gaa | ttt | gga | aag | gcc | aag | 9077 |
| Met | Gly | Lys | Arg | Glu | Lys | Lys | Gln | Gly | Glu | Phe | Gly | Lys | Ala | Lys |
| | | | 2980 | | | | 2985 | | | | | 2990 |

| ggc | agc | cgc | gcc | atc | tgg | tac | atg | tgg | cta | ggg | gct | aga | ttt | cta | 9122 |
| Gly | Ser | Arg | Ala | Ile | Trp | Tyr | Met | Trp | Leu | Gly | Ala | Arg | Phe | Leu |
| | | | 2995 | | | | 3000 | | | | | 3005 |

| gag | ttc | gaa | gcc | ctt | gga | ttc | ttg | aac | gag | gat | cac | tgg | atg | ggg | 9167 |
| Glu | Phe | Glu | Ala | Leu | Gly | Phe | Leu | Asn | Glu | Asp | His | Trp | Met | Gly |
| | | | 3010 | | | | 3015 | | | | | 3020 |

-continued

| | | |
|---|---|---|
| aga gag aat tca gga ggt ggt gtt gaa ggg cta gga tta caa aga<br>Arg Glu Asn Ser Gly Gly Gly Val Glu Gly Leu Gly Leu Gln Arg<br>                   3025                           3030                     3035 | 9212 |
| ctc gga tat gtc tta gaa gag atg agt cgc ata cca gga gga agg<br>Leu Gly Tyr Val Leu Glu Glu Met Ser Arg Ile Pro Gly Gly Arg<br>                   3040                           3045                     3050 | 9257 |
| atg tat gca gat gat act gct ggc tgg gac acc cgc atc agc agg<br>Met Tyr Ala Asp Asp Thr Ala Gly Trp Asp Thr Arg Ile Ser Arg<br>                   3055                           3060                     3065 | 9302 |
| ttt gat ctg gag aat gaa gct cta atc acc aac caa atg gag aaa<br>Phe Asp Leu Glu Asn Glu Ala Leu Ile Thr Asn Gln Met Glu Lys<br>                   3070                           3075                     3080 | 9347 |
| ggg cac agg gcc ttg gca ttg gcc ata atc aag tac aca tac caa<br>Gly His Arg Ala Leu Ala Leu Ala Ile Ile Lys Tyr Thr Tyr Gln<br>                   3085                           3090                     3095 | 9392 |
| aac aaa gtg gta aag gtc ctt aga cca gct gaa aaa ggg aag aca<br>Asn Lys Val Val Lys Val Leu Arg Pro Ala Glu Lys Gly Lys Thr<br>                   3100                           3105                     3110 | 9437 |
| gtt atg gac att att tca aga caa gac caa agg ggg agc gga caa<br>Val Met Asp Ile Ile Ser Arg Gln Asp Gln Arg Gly Ser Gly Gln<br>                   3115                           3120                     3125 | 9482 |
| gtt gtc act tac gct ctt aat aca ttt acc aac cta gtg gtg cag<br>Val Val Thr Tyr Ala Leu Asn Thr Phe Thr Asn Leu Val Val Gln<br>                   3130                           3135                     3140 | 9527 |
| ctc att cgg aat atg gag gct gag gaa gtt cta gag atg caa gac<br>Leu Ile Arg Asn Met Glu Ala Glu Glu Val Leu Glu Met Gln Asp<br>                   3145                           3150                     3155 | 9572 |
| ttg tgg ctg ctg cgg agg tca gag aaa gtg acc aac tgg ttg cag<br>Leu Trp Leu Leu Arg Arg Ser Glu Lys Val Thr Asn Trp Leu Gln<br>                   3160                           3165                     3170 | 9617 |
| agc aat gga tgg gat agg ctc aaa cga atg gca gtc agt gga gat<br>Ser Asn Gly Trp Asp Arg Leu Lys Arg Met Ala Val Ser Gly Asp<br>                   3175                           3180                     3185 | 9662 |
| gat tgc gtt gtg aaa cca att gat gat agg ttt gca cat gct ctc<br>Asp Cys Val Val Lys Pro Ile Asp Asp Arg Phe Ala His Ala Leu<br>                   3190                           3195                     3200 | 9707 |
| agg ttc ttg aat gat atg gga aaa gtt agg aag gac aca caa gag<br>Arg Phe Leu Asn Asp Met Gly Lys Val Arg Lys Asp Thr Gln Glu<br>                   3205                           3210                     3215 | 9752 |
| tgg aag ccc tca act gga tgg gac aac tgg gaa gaa gtt ccg ttt<br>Trp Lys Pro Ser Thr Gly Trp Asp Asn Trp Glu Glu Val Pro Phe<br>                   3220                           3225                     3230 | 9797 |
| tgc tcc cac cac ttc aac aag ctc cat ctc aag gac ggg agg tcc<br>Cys Ser His His Phe Asn Lys Leu His Leu Lys Asp Gly Arg Ser<br>                   3235                           3240                     3245 | 9842 |
| att gtg gtt ccc tgc cgc cac caa gat gaa ctg att ggc cga gct<br>Ile Val Val Pro Cys Arg His Gln Asp Glu Leu Ile Gly Arg Ala<br>                   3250                           3255                     3260 | 9887 |
| cgc gtc tca ccg ggg gcg gga tgg agc atc cgg gag act gct tgc<br>Arg Val Ser Pro Gly Ala Gly Trp Ser Ile Arg Glu Thr Ala Cys<br>                   3265                           3270                     3275 | 9932 |
| cta gca aaa tca tat gcg caa atg tgg cag ctc ctt tat ttc cac<br>Leu Ala Lys Ser Tyr Ala Gln Met Trp Gln Leu Leu Tyr Phe His<br>                   3280                           3285                     3290 | 9977 |
| aga agg gac ctc cga ctg atg gcc aat gcc att tgt tca tct gtg<br>Arg Arg Asp Leu Arg Leu Met Ala Asn Ala Ile Cys Ser Ser Val<br>                   3295                           3300                     3305 | 10022 |
| cca gtt gac tgg gtt cca act ggg aga act acc tgg tca atc cat<br>Pro Val Asp Trp Val Pro Thr Gly Arg Thr Thr Trp Ser Ile His<br>                   3310                           3315                     3320 | 10067 |

```
gga aag gga gaa tgg  atg acc act gaa gac  atg ctt gtg gtg tgg      10112
Gly Lys Gly Glu Trp  Met Thr Thr Glu Asp  Met Leu Val Val Trp
                3325                 3330                 3335 aac aga gtg tgg att  gag gag aac gac cac  atg gaa gac aag acc      10157
Asn Arg Val Trp Ile  Glu Glu Asn Asp His  Met Glu Asp Lys Thr
                3340                 3345                 3350 cca gtt acg aaa tgg  aca gac att ccc tat  ttg gga aaa agg gaa      10202
Pro Val Thr Lys Trp  Thr Asp Ile Pro Tyr  Leu Gly Lys Arg Glu
                3355                 3360                 3365 gac ttg tgg tgt ggg  tct ctc ata ggg cac  aga ccg cgc acc acc      10247
Asp Leu Trp Cys Gly  Ser Leu Ile Gly His  Arg Pro Arg Thr Thr
                3370                 3375                 3380 tgg gct gag aac att  aaa aac aca gtc aac  atg atg cgt agg atc      10292
Trp Ala Glu Asn Ile  Lys Asn Thr Val Asn  Met Met Arg Arg Ile
                3385                 3390                 3395 ata ggt gat gaa gaa  aag tac gtg gac tac  cta tcc acc caa gtt      10337
Ile Gly Asp Glu Glu  Lys Tyr Val Asp Tyr  Leu Ser Thr Gln Val
                3400                 3405                 3410 cgc tac ttg ggc gaa  gaa ggg tcc aca cct  gga gtg cta gcaccaatct  10386
Arg Tyr Leu Gly Glu  Glu Gly Ser Thr Pro  Gly Val Leu
                3415                 3420 tagtgttgtc aggcctgcta gtcagccaca gcttggggaa agctgtgcag cctgtgaccc  10446
ccccaggaga agctgggaaa ccaagcccat agtcaggccg agaacgccat ggcacggaag  10506
aagccatgct gcctgtgagc ccctcagagg acactgagtc aaaaaacccc acgcgcttgg  10566
aggcgcagga tgggaaaaga aggtggcgac cttccccacc ctttaatctg gggcctgaac  10626
tggagatcag ctgtggatct ccagaagagg gactagtggt tagaggagac cccccggaaa  10686
acgcaaaaca gcatattgac gctgggaaag accagagact ccatgagttt ccaccacgct  10746
ggccgccagg cacagatcgc cgaatagcgg cggccggtgt ggggaaatcc atgggtct    10804

<210> SEQ ID NO 2
<211> LENGTH: 3423
<212> TYPE: PRT
<213> ORGANISM: Flavivirus

<400> SEQUENCE: 2

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Thr Asp Thr Ser Val Gly Ile
            100                 105                 110

Val Gly Leu Leu Leu Thr Thr Ala Met Ala Val Glu Val Thr Arg Arg
        115                 120                 125

Gly Asn Ala Tyr Tyr Met Tyr Leu Asp Arg Ser Asp Ala Gly Glu Ala
    130                 135                 140

Ile Ser Phe Pro Thr Thr Met Gly Met Asn Lys Cys Tyr Ile Gln Ile
145                 150                 155                 160
```

```
Met Asp Leu Gly His Met Cys Asp Ala Thr Met Ser Tyr Glu Cys Pro
            165                 170                 175
Met Leu Asp Glu Gly Val Glu Pro Asp Val Asp Cys Trp Cys Asn
        180                 185                 190
Thr Thr Ser Thr Trp Val Val Tyr Gly Thr Cys His His Lys Lys Gly
            195                 200                 205
Glu Ala Arg Arg Ser Arg Arg Ala Val Thr Leu Pro Ser His Ser Thr
        210                 215                 220
Arg Lys Leu Gln Thr Arg Ser Gln Thr Trp Leu Glu Ser Arg Glu Tyr
225                 230                 235                 240
Thr Lys His Leu Ile Arg Val Glu Asn Trp Ile Phe Arg Asn Pro Gly
                245                 250                 255
Phe Ala Leu Ala Ala Ala Ile Ala Trp Leu Leu Gly Ser Ser Thr
                260                 265                 270
Ser Gln Lys Val Ile Tyr Leu Val Met Ile Leu Leu Ile Ala Pro Ala
        275                 280                 285
Tyr Ser Ile Arg Cys Ile Gly Val Ser Asn Arg Asp Phe Val Glu Gly
        290                 295                 300
Met Ser Gly Gly Thr Trp Val Asp Val Val Leu Glu His Gly Gly Cys
305                 310                 315                 320
Val Thr Val Met Ala Gln Asp Lys Pro Thr Val Asp Ile Glu Leu Val
                325                 330                 335
Thr Thr Thr Val Ser Asn Met Ala Glu Val Arg Ser Tyr Cys Tyr Glu
            340                 345                 350
Ala Ser Ile Ser Asp Met Ala Ser Asp Ser Arg Cys Pro Thr Gln Gly
        355                 360                 365
Glu Ala Tyr Leu Asp Lys Gln Ser Asp Thr Gln Tyr Val Cys Lys Arg
        370                 375                 380
Thr Leu Val Asp Arg Gly Trp Gly Asn Gly Cys Gly Leu Phe Gly Lys
385                 390                 395                 400
Gly Ser Leu Val Thr Cys Ala Lys Phe Ala Cys Ser Lys Lys Met Thr
                405                 410                 415
Gly Lys Ser Ile Gln Pro Glu Asn Leu Glu Tyr Arg Ile Met Leu Ser
            420                 425                 430
Val His Gly Ser Gln His Ser Gly Met Ile Val Asn Asp Thr Gly His
        435                 440                 445
Glu Thr Asp Glu Asn Arg Ala Lys Val Glu Ile Thr Pro Asn Ser Pro
        450                 455                 460
Arg Ala Glu Ala Thr Leu Gly Gly Phe Gly Ser Leu Gly Leu Asp Cys
465                 470                 475                 480
Glu Pro Arg Thr Gly Leu Asp Phe Ser Asp Leu Tyr Tyr Leu Thr Met
                485                 490                 495
Asn Asn Lys His Trp Leu Val His Lys Glu Trp Phe His Asp Ile Pro
            500                 505                 510
Leu Pro Trp His Ala Gly Ala Asp Thr Gly Thr Pro His Trp Asn Asn
        515                 520                 525
Lys Glu Ala Leu Val Glu Phe Lys Asp Ala His Ala Lys Arg Gln Thr
        530                 535                 540
Val Val Val Leu Gly Ser Gln Glu Gly Ala Val His Thr Ala Leu Ala
545                 550                 555                 560
Gly Ala Leu Glu Ala Glu Met Asp Gly Ala Lys Gly Arg Leu Ser Ser
                565                 570                 575
```

```
Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
                675                 680                 685

His Trp His Arg Ser Gly Ser Thr Ile Gly Lys Ala Phe Glu Ala Thr
            690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Val Trp Leu Gly Leu Asn
            755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
                820                 825                 830

Pro Arg Arg Leu Ala Ala Ala Val Lys Gln Ala Trp Glu Asp Gly Ile
            835                 840                 845

Cys Gly Ile Ser Ser Val Ser Arg Met Glu Asn Ile Met Trp Arg Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
                900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
    930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Ala Lys Gly Lys Glu Ala Val His Ser Asp Leu
            980                 985                 990
```

```
Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
    1010                1015                1020

Thr Leu Trp Thr Asp Gly Ile Glu Glu Ser Asp Leu Ile Ile Pro
    1025                1030                1035

Lys Ser Leu Ala Gly Pro Leu Ser His His Asn Thr Arg Glu Gly
    1040                1045                1050

Tyr Arg Thr Gln Met Glu Gly Pro Trp His Ser Glu Glu Leu Glu
    1055                1060                1065

Ile Arg Phe Glu Glu Cys Pro Gly Thr Lys Val His Val Glu Glu
    1070                1075                1080

Thr Cys Gly Thr Arg Gly Pro Ser Leu Arg Ser Thr Thr Ala Ser
    1085                1090                1095

Gly Arg Val Ile Glu Glu Trp Cys Cys Arg Glu Cys Thr Met Pro
    1100                1105                1110

Pro Leu Ser Phe Arg Ala Lys Asp Gly Cys Trp Tyr Gly Met Glu
    1115                1120                1125

Ile Arg Pro Arg Lys Glu Pro Glu Ser Asn Leu Val Arg Ser Met
    1130                1135                1140

Val Thr Ala Gly Ser Thr Asp His Met Asp His Phe Ser Leu Gly
    1145                1150                1155

Val Leu Val Ile Leu Leu Met Val Gln Glu Gly Leu Lys Lys Arg
    1160                1165                1170

Met Thr Thr Lys Ile Ile Ile Ser Thr Ser Met Ala Val Leu Val
    1175                1180                1185

Ala Met Ile Leu Gly Gly Phe Ser Met Ser Asp Leu Ala Lys Leu
    1190                1195                1200

Ala Ile Leu Met Gly Ala Thr Phe Ala Glu Met Asn Thr Gly Gly
    1205                1210                1215

Asp Val Ala His Leu Ala Leu Ile Ala Ala Phe Lys Val Arg Pro
    1220                1225                1230

Ala Leu Leu Val Ser Phe Ile Phe Arg Ala Asn Trp Thr Pro Arg
    1235                1240                1245

Glu Ser Met Leu Leu Ala Leu Ala Ser Cys Leu Leu Gln Thr Ala
    1250                1255                1260

Ile Ser Ala Leu Glu Gly Asp Leu Met Val Pro Ile Asn Gly Phe
    1265                1270                1275

Ala Leu Ala Trp Leu Ala Ile Arg Ala Met Val Val Pro Arg Thr
    1280                1285                1290

Asp Asn Ile Thr Leu Ala Ile Leu Ala Ala Leu Thr Pro Leu Ala
    1295                1300                1305

Arg Gly Thr Leu Leu Val Ala Trp Arg Ala Gly Leu Ala Thr Cys
    1310                1315                1320

Gly Gly Phe Met Leu Leu Ser Leu Lys Gly Lys Gly Ser Val Lys
    1325                1330                1335

Lys Asn Leu Pro Phe Val Met Ala Leu Gly Leu Thr Ala Val Arg
    1340                1345                1350

Leu Val Asp Pro Ile Asn Val Val Gly Leu Leu Leu Leu Thr Arg
    1355                1360                1365

Ser Gly Lys Arg Ser Trp Pro Pro Ser Glu Val Leu Thr Ala Val
    1370                1375                1380
```

-continued

Gly Leu Ile Cys Ala Leu Ala Gly Gly Phe Ala Lys Ala Asp Ile
1385            1390            1395

Glu Met Ala Gly Pro Met Ala Ala Val Gly Leu Leu Ile Val Ser
1400            1405            1410

Tyr Val Val Ser Gly Lys Ser Val Asp Met Tyr Ile Glu Arg Ala
1415            1420            1425

Gly Asp Ile Thr Trp Glu Lys Asp Ala Glu Val Thr Gly Asn Ser
1430            1435            1440

Pro Arg Leu Asp Val Ala Leu Asp Glu Ser Gly Asp Phe Ser Leu
1445            1450            1455

Val Glu Asp Asp Gly Pro Pro Met Arg Glu Ile Ile Leu Lys Val
1460            1465            1470

Val Leu Met Ala Ile Cys Gly Met Asn Pro Ile Ala Ile Pro Phe
1475            1480            1485

Ala Ala Gly Ala Trp Tyr Val Tyr Val Lys Thr Gly Lys Arg Ser
1490            1495            1500

Gly Ala Leu Trp Asp Val Pro Ala Pro Lys Glu Val Lys Lys Gly
1505            1510            1515

Glu Thr Thr Asp Gly Val Tyr Arg Val Met Thr Arg Arg Leu Leu
1520            1525            1530

Gly Ser Thr Gln Val Gly Val Gly Val Met Gln Glu Gly Val Phe
1535            1540            1545

His Thr Met Trp His Val Thr Lys Gly Ser Ala Leu Arg Ser Gly
1550            1555            1560

Glu Gly Arg Leu Asp Pro Tyr Trp Gly Asp Val Lys Gln Asp Leu
1565            1570            1575

Val Ser Tyr Cys Gly Pro Trp Lys Leu Asp Ala Ala Trp Asp Gly
1580            1585            1590

His Ser Glu Val Gln Leu Leu Ala Val Pro Pro Gly Glu Arg Ala
1595            1600            1605

Arg Asn Ile Gln Thr Leu Pro Gly Ile Phe Lys Thr Lys Asp Gly
1610            1615            1620

Asp Ile Gly Ala Val Ala Leu Asp Tyr Pro Ala Gly Thr Ser Gly
1625            1630            1635

Ser Pro Ile Leu Asp Lys Cys Gly Arg Val Ile Gly Leu Tyr Gly
1640            1645            1650

Asn Gly Val Val Ile Lys Asn Gly Ser Tyr Val Ser Ala Ile Thr
1655            1660            1665

Gln Gly Arg Arg Glu Glu Glu Thr Pro Val Glu Cys Phe Glu Pro
1670            1675            1680

Ser Met Leu Lys Lys Lys Gln Leu Thr Val Leu Asp Leu His Pro
1685            1690            1695

Gly Ala Gly Lys Thr Arg Arg Val Leu Pro Glu Ile Val Arg Glu
1700            1705            1710

Ala Ile Lys Thr Arg Leu Arg Thr Val Ile Leu Ala Pro Thr Arg
1715            1720            1725

Val Val Ala Ala Glu Met Glu Glu Ala Leu Arg Gly Leu Pro Val
1730            1735            1740

Arg Tyr Met Thr Thr Ala Val Asn Val Thr His Ser Gly Thr Glu
1745            1750            1755

Ile Val Asp Leu Met Cys His Ala Thr Phe Thr Ser Arg Leu Leu
1760            1765            1770

-continued

Gln Pro Ile Arg Val Pro Asn Tyr Asn Leu Tyr Ile Met Asp Glu
1775                    1780                1785

Ala His Phe Thr Asp Pro Ser Ser Ile Ala Ala Arg Gly Tyr Ile
1790                    1795                1800

Ser Thr Arg Val Glu Met Gly Glu Ala Ala Ile Phe Met Thr
1805                    1810                1815

Ala Thr Pro Pro Gly Thr Arg Asp Ala Phe Pro Asp Ser Asn Ser
1820                    1825                1830

Pro Ile Met Asp Thr Glu Val Glu Val Pro Glu Arg Ala Trp Ser
1835                    1840                1845

Ser Gly Phe Asp Trp Val Thr Asp His Ser Gly Lys Thr Val Trp
1850                    1855                1860

Phe Val Pro Ser Val Arg Asn Gly Asn Glu Ile Ala Ala Cys Leu
1865                    1870                1875

Thr Lys Ala Gly Lys Arg Val Ile Gln Leu Ser Arg Lys Thr Phe
1880                    1885                1890

Glu Thr Glu Phe Gln Lys Thr Lys His Gln Glu Trp Asp Phe Val
1895                    1900                1905

Val Thr Thr Asp Ile Ser Glu Met Gly Ala Asn Phe Lys Ala Asp
1910                    1915                1920

Arg Val Ile Asp Ser Arg Arg Cys Leu Lys Pro Val Ile Leu Asp
1925                    1930                1935

Gly Glu Arg Val Ile Leu Ala Gly Pro Met Pro Val Thr His Ala
1940                    1945                1950

Ser Ala Ala Gln Arg Arg Gly Arg Ile Gly Arg Asn Pro Asn Lys
1955                    1960                1965

Pro Gly Asp Glu Tyr Leu Tyr Gly Gly Gly Cys Ala Glu Thr Asp
1970                    1975                1980

Glu Asp His Ala His Trp Leu Glu Ala Arg Met Leu Leu Asp Asn
1985                    1990                1995

Ile Tyr Leu Gln Asp Gly Leu Ile Ala Ser Leu Tyr Arg Pro Glu
2000                    2005                2010

Ala Asp Lys Val Ala Ala Ile Glu Gly Glu Phe Lys Leu Arg Thr
2015                    2020                2025

Glu Gln Arg Lys Thr Phe Val Glu Leu Met Lys Arg Gly Asp Leu
2030                    2035                2040

Pro Val Trp Leu Ala Tyr Gln Val Ala Ser Ala Gly Ile Thr Tyr
2045                    2050                2055

Thr Asp Arg Arg Trp Cys Phe Asp Gly Thr Thr Asn Asn Thr Ile
2060                    2065                2070

Met Glu Asp Ser Val Pro Ala Glu Val Trp Thr Arg Tyr Gly Glu
2075                    2080                2085

Lys Arg Val Leu Lys Pro Arg Trp Met Asp Ala Arg Val Cys Ser
2090                    2095                2100

Asp His Ala Ala Leu Lys Ser Phe Lys Glu Phe Ala Ala Gly Lys
2105                    2110                2115

Arg Gly Ala Ala Phe Gly Val Met Glu Ala Leu Gly Thr Leu Pro
2120                    2125                2130

Gly His Met Thr Glu Arg Phe Gln Glu Ala Ile Asp Asn Leu Ala
2135                    2140                2145

Val Leu Met Arg Ala Glu Thr Gly Ser Arg Pro Tyr Lys Ala Ala
2150                    2155                2160

```
Ala Ala Gln Leu Pro Glu Thr Leu Glu Thr Ile Met Leu Leu Gly
2165                2170                2175

Leu Leu Gly Thr Val Ser Leu Gly Ile Phe Phe Val Leu Met Arg
2180                2185                2190

Asn Lys Gly Ile Gly Lys Met Gly Phe Gly Met Val Thr Leu Gly
2195                2200                2205

Ala Ser Ala Trp Leu Met Trp Leu Ser Glu Ile Glu Pro Ala Arg
2210                2215                2220

Ile Ala Cys Val Leu Ile Val Val Phe Leu Leu Leu Val Val Leu
2225                2230                2235

Ile Pro Glu Pro Glu Lys Gln Arg Ser Pro Gln Asp Asn Gln Met
2240                2245                2250

Ala Ile Ile Ile Met Val Ala Val Gly Leu Leu Gly Leu Ile Thr
2255                2260                2265

Ala Asn Glu Leu Gly Trp Leu Glu Arg Thr Lys Ser Asp Leu Ser
2270                2275                2280

His Leu Met Gly Arg Arg Glu Glu Gly Ala Thr Ile Gly Phe Ser
2285                2290                2295

Met Asp Ile Asp Leu Arg Pro Ala Ser Ala Trp Ala Ile Tyr Ala
2300                2305                2310

Ala Leu Thr Thr Phe Ile Thr Pro Ala Val Gln His Ala Val Thr
2315                2320                2325

Thr Ser Tyr Asn Asn Tyr Ser Leu Met Ala Met Ala Thr Gln Ala
2330                2335                2340

Gly Val Leu Phe Gly Met Gly Lys Gly Met Pro Phe Tyr Ala Trp
2345                2350                2355

Asp Phe Gly Val Pro Leu Leu Met Ile Gly Cys Tyr Ser Gln Leu
2360                2365                2370

Thr Pro Leu Thr Leu Ile Val Ala Ile Ile Leu Leu Val Ala His
2375                2380                2385

Tyr Met Tyr Leu Ile Pro Gly Leu Gln Ala Ala Ala Ala Arg Ala
2390                2395                2400

Ala Gln Lys Arg Thr Ala Ala Gly Ile Met Lys Asn Pro Val Val
2405                2410                2415

Asp Gly Ile Val Val Thr Asp Ile Asp Thr Met Thr Ile Asp Pro
2420                2425                2430

Gln Val Glu Lys Lys Met Gly Gln Val Leu Leu Ile Ala Val Ala
2435                2440                2445

Val Ser Ser Ala Ile Leu Ser Arg Thr Ala Trp Gly Trp Gly Glu
2450                2455                2460

Ala Gly Ala Leu Ile Thr Ala Ala Thr Ser Thr Leu Trp Glu Gly
2465                2470                2475

Ser Pro Asn Lys Tyr Trp Asn Ser Ser Thr Ala Thr Ser Leu Cys
2480                2485                2490

Asn Ile Phe Arg Gly Ser Tyr Leu Ala Gly Ala Ser Leu Ile Tyr
2495                2500                2505

Thr Val Thr Arg Asn Ala Gly Leu Val Lys Arg Arg Gly Gly Gly
2510                2515                2520

Thr Gly Glu Thr Leu Gly Glu Lys Trp Lys Ala Arg Leu Asn Gln
2525                2530                2535

Met Ser Ala Leu Glu Phe Tyr Ser Tyr Lys Lys Ser Gly Ile Thr
2540                2545                2550
```

-continued

| | | | | | | | | | | | |
|---|---|---|---|---|---|---|---|---|---|---|---|
| Glu | Val | Cys | Arg | Glu | Glu | Ala | Arg | Arg | Ala | Leu | Lys | Asp | Gly | Val |
| | 2555 | | | | 2560 | | | | 2565 | | |

```
Glu Val Cys Arg Glu Glu Ala Arg Arg Ala Leu Lys Asp Gly Val
    2555                2560               2565

Ala Thr Gly Gly His Ala Val Ser Arg Gly Ser Ala Lys Leu Arg
    2570                2575               2580

Trp Leu Val Glu Arg Gly Tyr Leu Gln Pro Tyr Gly Lys Val Ile
    2585                2590               2595

Asp Leu Gly Cys Gly Arg Gly Gly Trp Ser Tyr Tyr Ala Ala Thr
    2600                2605               2610

Ile Arg Lys Val Gln Glu Val Lys Gly Tyr Thr Lys Gly Gly Pro
    2615                2620               2625

Gly His Glu Glu Pro Met Leu Val Gln Ser Tyr Gly Trp Asn Ile
    2630                2635               2640

Val Arg Leu Lys Ser Gly Val Asp Val Phe His Met Ala Ala Glu
    2645                2650               2655

Pro Cys Asp Thr Leu Leu Cys Asp Ile Gly Glu Ser Ser Ser Ser
    2660                2665               2670

Pro Glu Val Glu Glu Ala Arg Thr Leu Arg Val Leu Ser Met Val
    2675                2680               2685

Gly Asp Trp Leu Glu Lys Arg Pro Gly Ala Phe Cys Ile Lys Val
    2690                2695               2700

Leu Cys Pro Tyr Thr Ser Thr Met Met Glu Thr Leu Glu Arg Leu
    2705                2710               2715

Gln Arg Arg Tyr Gly Gly Gly Leu Val Arg Val Pro Leu Ser Arg
    2720                2725               2730

Asn Ser Thr His Glu Met Tyr Trp Val Ser Gly Ala Lys Ser Asn
    2735                2740               2745

Thr Ile Lys Ser Val Ser Thr Thr Ser Gln Leu Leu Leu Gly Arg
    2750                2755               2760

Met Asp Gly Pro Arg Arg Pro Val Lys Tyr Glu Glu Asp Val Asn
    2765                2770               2775

Leu Gly Ser Gly Thr Arg Ala Val Val Ser Cys Ala Glu Ala Pro
    2780                2785               2790

Asn Met Lys Ile Ile Gly Asn Arg Ile Glu Arg Ile Arg Ser Glu
    2795                2800               2805

His Ala Glu Thr Trp Phe Phe Asp Glu Asn His Pro Tyr Arg Thr
    2810                2815               2820

Trp Ala Tyr His Gly Ser Tyr Glu Ala Pro Thr Gln Gly Ser Ala
    2825                2830               2835

Ser Ser Leu Ile Asn Gly Val Val Arg Leu Leu Ser Lys Pro Trp
    2840                2845               2850

Asp Val Val Thr Gly Val Thr Gly Ile Ala Met Thr Asp Thr Thr
    2855                2860               2865

Pro Tyr Gly Gln Gln Arg Val Phe Lys Glu Lys Val Asp Thr Arg
    2870                2875               2880

Val Pro Asp Pro Gln Glu Gly Thr Arg Gln Val Met Ser Met Val
    2885                2890               2895

Ser Ser Trp Leu Trp Lys Glu Leu Gly Lys His Lys Arg Pro Arg
    2900                2905               2910

Val Cys Thr Lys Glu Glu Phe Ile Asn Lys Val Arg Ser Asn Ala
    2915                2920               2925

Ala Leu Gly Ala Ile Phe Glu Glu Glu Lys Glu Trp Lys Thr Ala
    2930                2935               2940
```

Val Glu Ala Val Asn Asp Pro Arg Phe Trp Ala Leu Val Asp Lys
2945                2950                2955

Glu Arg Glu His His Leu Arg Gly Glu Cys Gln Ser Cys Val Tyr
2960                2965                2970

Asn Met Met Gly Lys Arg Glu Lys Lys Gln Gly Glu Phe Gly Lys
2975                2980                2985

Ala Lys Gly Ser Arg Ala Ile Trp Tyr Met Trp Leu Gly Ala Arg
2990                2995                3000

Phe Leu Glu Phe Glu Ala Leu Gly Phe Leu Asn Glu Asp His Trp
3005                3010                3015

Met Gly Arg Glu Asn Ser Gly Gly Val Glu Gly Leu Gly Leu
3020                3025                3030

Gln Arg Leu Gly Tyr Val Leu Glu Glu Met Ser Arg Ile Pro Gly
3035                3040                3045

Gly Arg Met Tyr Ala Asp Asp Thr Ala Gly Trp Asp Thr Arg Ile
3050                3055                3060

Ser Arg Phe Asp Leu Glu Asn Glu Ala Leu Ile Thr Asn Gln Met
3065                3070                3075

Glu Lys Gly His Arg Ala Leu Ala Leu Ala Ile Ile Lys Tyr Thr
3080                3085                3090

Tyr Gln Asn Lys Val Val Lys Val Leu Arg Pro Ala Glu Lys Gly
3095                3100                3105

Lys Thr Val Met Asp Ile Ile Ser Arg Gln Asp Gln Arg Gly Ser
3110                3115                3120

Gly Gln Val Val Thr Tyr Ala Leu Asn Thr Phe Thr Asn Leu Val
3125                3130                3135

Val Gln Leu Ile Arg Asn Met Glu Ala Glu Glu Val Leu Glu Met
3140                3145                3150

Gln Asp Leu Trp Leu Leu Arg Arg Ser Glu Lys Val Thr Asn Trp
3155                3160                3165

Leu Gln Ser Asn Gly Trp Asp Arg Leu Lys Arg Met Ala Val Ser
3170                3175                3180

Gly Asp Asp Cys Val Val Lys Pro Ile Asp Asp Arg Phe Ala His
3185                3190                3195

Ala Leu Arg Phe Leu Asn Asp Met Gly Lys Val Arg Lys Asp Thr
3200                3205                3210

Gln Glu Trp Lys Pro Ser Thr Gly Trp Asp Asn Trp Glu Glu Val
3215                3220                3225

Pro Phe Cys Ser His His Phe Asn Lys Leu His Leu Lys Asp Gly
3230                3235                3240

Arg Ser Ile Val Val Pro Cys Arg His Gln Asp Glu Leu Ile Gly
3245                3250                3255

Arg Ala Arg Val Ser Pro Gly Ala Gly Trp Ser Ile Arg Glu Thr
3260                3265                3270

Ala Cys Leu Ala Lys Ser Tyr Ala Gln Met Trp Gln Leu Leu Tyr
3275                3280                3285

Phe His Arg Arg Asp Leu Arg Leu Met Ala Asn Ala Ile Cys Ser
3290                3295                3300

Ser Val Pro Val Asp Trp Val Pro Thr Gly Arg Thr Thr Trp Ser
3305                3310                3315

Ile His Gly Lys Gly Glu Trp Met Thr Thr Glu Asp Met Leu Val
3320                3325                3330

| Val | Trp | Asn | Arg | Val | Trp | Ile | Glu | Glu | Asn | Asp | His | Met | Glu | Asp |
|-----|-----|-----|-----|-----|-----|-----|-----|-----|-----|-----|-----|-----|-----|-----|
| 3335| | | | 3340| | | | | 3345| | | | | |

Lys Thr Pro Val Thr Lys Trp Thr Asp Ile Pro Tyr Leu Gly Lys
3350           3355                3360

Arg Glu Asp Leu Trp Cys Gly Ser Leu Ile Gly His Arg Pro Arg
3365           3370                3375

Thr Thr Trp Ala Glu Asn Ile Lys Asn Thr Val Asn Met Met Arg
3380           3385                3390

Arg Ile Ile Gly Asp Glu Glu Lys Tyr Val Asp Tyr Leu Ser Thr
3395           3400                3405

Gln Val Arg Tyr Leu Gly Glu Glu Gly Ser Thr Pro Gly Val Leu
3410           3415                3420

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 3
taatacgact cactatag                                                  18

<210> SEQ ID NO 4
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 4
gggtcggcat ggcatctcca cctcctcgcg gtccgacctg ggctacttcg gtaggctaag    60
ggagaag                                                              67

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
gcctacccgg aactgagtgt c                                              21

<210> SEQ ID NO 6
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 6
taatacgact cactatagag ttgttgatct gtgtgaatca gactg                    45

<210> SEQ ID NO 7
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 7
tcacacagat caacaactct atagtgagtc gtattagcgg ccgc                     44

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
gcaaagggag cctggtgaca tgcgc                                          25

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 9
ccatcgatga cgaacacccc tgtaccgc                                       28

<210> SEQ ID NO 10
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 10
tctgcggccg cgggtctgaa tacaaagaat gg                                  32

<210> SEQ ID NO 11
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 11
gctctagata tcgatttgga ctgtttccag tgacttcc                            38

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 12
cggaattcac catttgtcat ggccctggga ctaac                               35

<210> SEQ ID NO 13
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 13
gctctagata tcgatttctc tggcgtccat ccacctcgg                           39

<210> SEQ ID NO 14
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 14
cggaattcca acatttacct ccaagatggc ctc                                    33

<210> SEQ ID NO 15
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 15
gctctagata tcgatttctt accacagccc gcgtgccag                              39

<210> SEQ ID NO 16
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 16
ggggtaccgt aggtatgggg gaggactggt cagag                                  35

<210> SEQ ID NO 17
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 17
gctctagata tcgatttcat gataagatac attgatg                                37

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18
gggaaatcca tggtttctgg tcggcatggc atctc                                  35

<210> SEQ ID NO 19
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 19
gagatgccat gccgaccaga aaccatggat ttccccacac cggcc                       45

<210> SEQ ID NO 20
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 20
attccattac cttggcacgc tggggcagac acc                                    33

```
<210> SEQ ID NO 21
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 21
ggtgtctgcc ccagcgtgcc aaggtaatgg aat                                    33

<210> SEQ ID NO 22
<211> LENGTH: 3400
<212> TYPE: DNA
<213> ORGANISM: Artificial Sequence
<220> FEATURE:
<223> OTHER INFORMATION: synthetic plasmid

<400> SEQUENCE: 22
aatcgattgt atgggaagcc cgatgcgcca gagttgtttc tgaaacatgg caaaggtagc        60
gttgccaatg atgttacaga tgagatggtc agactaaact ggctgacgga atttatgcct       120
cttccgacca tcaagcattt tatccgtact cctgatgatg catggttact caccactgcg       180
atccccggga aaacagcatt ccaggtatta gaagaatatc ctgattcagg tgaaaatatt       240
gttgatgcgc tggcagtgtt cctgcgccgg ttgcattcga ttcctgtttg taattgtcct       300
tttaacagcg atcgcgtatt tcgtctcgct caggcgcaat cacgaatgaa taacggtttg       360
gttgatgcga gtgattttga tgacgagcgt aatggctggc ctgttgaaca agtctggaaa       420
gaaatgcata gcttttgcc attctcaccg gattcagtcg tcactcatgg tgatttctca       480
cttgataacc ttatttttga cgaggggaaa ttaataggtt gtattgatgt tggacgagtc       540
ggaatcgcag accgatacca ggatcttgcc atcctatgga actgcctcgg tgagttttct       600
ccttcattac agaaacggct ttttcaaaaa tatggtattg ataatcctga tatgaataaa       660
ttgcagtttc atttgatgct cgatgagttt ttctaatcag aattggttaa ttggttgtaa       720
cactggcaga gcattacgct gacttgacgg gacggcggct ttgttgaata atcgaactt       780 ttgctgagtt gaaggatcag atcacgcatc ttcccgacaa cgcagaccgt tccgtggcaa       840
agcaaaagtt caaaatcacc aactggtcca cctacaacaa agctctcatc aaccgtggct       900
ccctcacttt ctggctggat gatggggcga ttcaggcctg gtatgagtca gcaacacctt       960
cttcacgagg cagacctcag cgctcaaaga tgcaggggta aaagctaacc gcatctttac      1020
cgacaaggca tccggcagtt caacagatcg ggaagggctg gatttgctga ggatgaaggt      1080
ggaggaaggt gatgtcattc tggtgaagaa gctcgaccgt cttggccgcg acaccgccga      1140
catgatccaa ctgataaaag agtttgatgc tcagggtgta gcggttcggt ttattgacga      1200
cgggatcagt accgacggtg atatggggca atggtggtc accatcctgt cggctgtggc      1260
acaggctgaa cgccggagga tcctagagcg cacgaatgag ggccgacagg aagcaaagct      1320
gaaaggaatc aaatttggcc gcaggcgtac cgtggacagg aacgtcgtgc tgacgcttca      1380
tcagaagggc actggtgcaa cggaaattgc tcatcagctc agtattgccc gctccacggt      1440
ttataaaatt cttgaagacg aaaggggcctc gtgatacgcc tatttttata ggttaatgtc      1500
atgataataa tggtttctta gacgtcaggt ggcactttc ggggaaatgt gcgcggaacc      1560
cctatttgtt tatttttcta aatacattca aatatgtatc cgctcatgag acaataaccc      1620
tgataaatgc ttcaataata ttgaaaaagg aagagtatga gtattcaaca tttccgtgtc      1680
gcccttattc ccttttttgc ggcatttgc cttcctgttt ttgctcaccc agaaacgctg      1740
```

```
gtgaaagtaa aagatgctga agatcagttg ggtgcacgag tgggttacat cgaactggat    1800
ctcaacagcg gtaagatcct tgagagtttt cgccccgaag aacgttttcc aatgatgagc    1860
acttttaaag ttctgctatg tggcgcggta ttatcccgtg ttgacgccgg gcaagagcaa    1920
ctcggtcgcc gcatacacta ttctcagaat gacttggttg agtactcacc agtcacagaa    1980
aagcatctta cggatggcat gacagtaaga gaattatgca gtgctgccat aaccatgagt    2040
gataacactg cggccaactt acttctgaca acgatcggag gaccgaagga gctaaccgct    2100
tttttgcaca acatggggga tcatgtaact cgccttgatc gttgggaacc ggagctgaat    2160
gaagccatac caaacgacga gcgtgacacc acgatgcctg cagcaatggc aacaacgttg    2220
cgcaaactat taactggcga actacttact ctagcttccc ggcaacaatt aatagactgg    2280
atggaggcgg ataaagttgc aggaccactt ctgcgctcgg cccttccggc tggctggttt    2340
attgctgata atctggagc cggtgagcgt gggtctcgcg gtatcattgc agcactgggg    2400
ccagatggta agccctcccg tatcgtagtt atctacacga cggggagtca ggcaactatg    2460
gatgaacgaa atagacagat cgctgagata ggtgcctcac tgattaagca ttggtaactg    2520
tcagaccaag tttactcata tatactttag attgatttaa aacttcattt ttaatttaaa    2580
aggatctagg tgaagatcct ttttgataat ctcatgacca aaatccctta acgtgagttt    2640
tcgttccact gagcgtcaga ccccttaata agatgatctt cttgagatcg ttttggtctg    2700
cgcgtaatct cttgctctga aaacgaaaaa accgccttgc agggcggttt tcgaaggtt    2760 ctctgagcta ccaactcttt gaaccgaggt aactggcttg gaggagcgca gtcaccaaaa    2820
cttgtccttt cagtttagcc ttaaccggcg catgacttca agactaactc ctctaaatca    2880
attaccagtg gctgctgcca gtggtgcttt tgcatgtctt tccgggttgg actcaagacg    2940
atagttaccg gataaggcgc agcggtcgga ctgaacgggg ggttcgtgca tacagtccag    3000
cttggagcga actgcctacc cggaactgag tgtcaggcgt ggaatgagac aaacgcggcc    3060
ataacagcgg aatgacaccg gtaaaccgaa aggcaggaac aggagagcgc acgagggagc    3120
cgccaggggg aaacgcctgg tatctttata gtcctgtcgg gtttcgccac cactgatttg    3180
agcgtcagat ttcgtgatgc ttgtcagggg ggcggagcct atggaaaaac ggctttgccg    3240
cggccctctc acttccctgt taagtatctt cctggcatct tccaggaaat ctccgccccg    3300
ttcgtaagcc atttccgctc gccgcagtcg aacgaccgag cgtagcgagt cagtgagcga    3360
ggaagcggaa tatatcctgt atcacatatt ctgcggccgc                          3400
```

REVERSE GENETICS SYSTEM OF ZIKA VIRUS

PRIORITY PARAGRAPH

This Application is a national phase application under 35 U.S.C. § 371 of International Application No. PCT/US2017/030810, filed May 3, 2017 which claims priority to U.S. Provisional Application 62/330,958 filed May 3, 2016 and U.S. Provisional Application 62/455,846, each of which is incorporated herein by reference in its entirety.

STATEMENT REGARDING FEDERALLY FUNDED RESEARCH

This invention was made with government support under AI087856 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

The current explosive epidemic of Zika virus (ZIKV) in Americas poses a global public health emergency. ZIKV is a member of *Flavivirus* genus within the Flaviviradae family. Flaviviruses have a positive-strand RNA genome of about 11,000 nucleotides. The flaviviral genome encodes three structural proteins (capsid [C], pre-membrane/membrane [prM/M], and envelope [E]) and seven nonstructural proteins (NS1, NS2A, NS2B, NS3, NS4A, NS4B, and NS5). The structural proteins form viral particles. The non-structural proteins participate in viral replication, virion assembly, and evasion of the host immune response (Lindenbach et al (2013). Flaviviridae. p. 712-746. In D. M. Knipe and P. M. Howley (ed), Fields virology, 6th., vol. 1. Lippincott William & Wilkins, Philadelphia, Pa.). Like ZIKV, many flaviviruses are significant human pathogens, including yellow fever virus (YFV), West Nile virus (WNV), Japanese encephalitis virus (JEV), tick-borne encephalitis virus (TBEV), and dengue virus (DENV). ZIKV is transmitted by *Aedes* spp. mosquitoes, which also transmit YFV and DENV, as well as chikungunya virus. In addition, ZIKV may also be transmitted through sex, blood transfusion, organ transplantation, and potentially through urine or saliva (Musso et al., (2014) *Euro Surveill* 19; Musso et al., (2015) *Emerg Infect Dis* 21, 359-61). Individuals with compromised immunity could be more susceptible to ZIKV infection and disease development (Shan et al., (2016) *ACS Infectious Diseases* 2, 170-72).

Experimental systems, including a reverse genetic system of ZIKV, animal models, and mosquito transmission models, are urgently needed to address these key scientific questions. For animal models, A129 (lacking interferon α/β receptors), AG129 (lacking interferon α/β and γ receptors), and Irf3$^{-/-}$ Irf5$^{-/-}$ Irf$^{-/-}$ triple knockout mice were recently reported to be susceptible to ZIKV infection and to develop neurological diseases (Lazear et al., (2016) A mouse model of Zika virus pathogenesis, *Cell Host & Microbe*; Rossi et al., (2016) Characterization of a Novel Murine Model to Study Zika Virus, *Am J Trop Med Hyg*; Zmurko et al. (2016) The viral polymerase inhibitor 7-deaza-2'-C-methyladenosine is a potent inhibitor of in vitro Zika virus replication and delays disease progression in a robust mouse infection model. bioRxiv); infection of rhesus macaques with an Asian lineage ZIKV was also reported recently (Dudley et al. (2016). Natural history of Asian lineage Zika virus infection in macaques. bioRxiv). For mosquito infection, one study showed that *A. aegypti* and *A. albopictus* mosquitoes are unexpectedly poor vectors for ZIKV, with disseminated infection rates generally <50% following high titer ($10^7$ tissue culture infectious dose 50%) oral doses. This suggests the possibility that other mosquito vectors or human-to-human transmission may be contributing to the explosive spread of the virus (Chouin-Carneiro et al., (2016). *PLoS Negl Trop Dis* 10, e0004543).

The potential association of microcephaly and other congenital abnormalities with Zika virus (ZIKV) infection during pregnancy underlines the critical need for a rapid and accurate diagnosis. Due to the short duration of ZIKV viremia in infected patients, a serologic assay that detects antibody responses to viral infection plays an essential role in diagnosing patient specimens. The current serologic diagnosis of ZIKV infection relies heavily on the labor-intensive Plaque Reduction Neutralization Test (PRNT) that requires more than one-week turnaround time and represents a major bottleneck for patient diagnosis.

There is a need for additional reverse genetic systems for Zika virus, as well as additional methods of detecting and diagnosing viral infections such as Zika virus infection.

SUMMARY

Embodiments of the current invention provide additional compositions and methods to overcome the limitations of current methods. The inventors have developed a high-throughput assay for ZIKV and dengue virus (DENV) diagnosis that can attain at least the sensitivity and selectivity of the current PRNT assay. The assays described herein are homogeneous and utilize luciferase viruses to quantify the neutralizing titers in a 96-well format. The inventors have demonstrated that the reporter diagnostic assay of the present invention has a higher dynamic range and maintains the relative specificity of the traditional PRNT assay. Besides the improvement of assay throughput, the reporter virus technology has also shortened the turnaround time to less than two days. Collectively, the results suggest that, along with the viral RT-PCR assay, the reporter virus-based serologic assay could be readily used as a first-line test for clinical diagnosis of ZIKV infection as well as for vaccine clinical trials.

Certain embodiments of the invention are directed to a high-throughput Zika diagnostic assay to measure neutralizing titers of patient specimens using a reporter ZIKV. The assay described herein can have an increased diagnostic dynamic range and a shortened turnaround time from greater than 7 days to less than 2 days in a 96-well format. The assay described herein can also be used in conjunction with viral RT-PCR assays, the reporter serologic assay may serve as the first-line test for diagnosing ZIKV infection. In certain aspects the ZIKV infection is a primary ZIKV infection. As used herein, the term "primary" viral infection refers to a first or original infection, for example, following a first exposure to a virus. In certain aspects a primary ZIKV viral infection presents ZIKV as the only *flavivirus* infection of the subject.

Certain embodiments are directed to an assay for detecting *flavivirus* infection comprising one or more of the following steps: (a) contacting a sample from a subject suspected of having a *flavivirus* infection with a reporter Zika virus (rZIKV), the rZIKV configured to produce a detectable signal when expressed in viable cell, forming a reporter mixture and incubating the reporter mixture at a temperature of 35 to 40° C.; (b) contacting a host cell monolayer with the reporter mixture under cell growth conditions at about 37° C. forming an inoculated cell monolayer; (c) measuring the reporter signal produced by the inoculated cell monolayer and normalizing the measured signal to a control; and (d) calculating a ZIKV antibody titer of the sample using the reporter signal measurements. In certain instances antibodies present in the sample can bind an neutralize a reporter virus, thus a higher antibody titer results in a lower reporter signal due to reporter virus neutralization. In certain aspects a serial dilution of the sample is contacted with the rZIKV. In a further aspect a plurality of samples are assayed individually. The sample can be a biological sample, such as a blood sample. In certain aspects the sample is from a pregnant subject. The subject can be a mammalian subject, such as a human.

The rZIKV can be a luciferase reporter ZIKV. The luciferase reporter ZIKV expresses a reporter molecule when infecting a cell. In certain aspects the luciferase is *Renilla* luciferase.

The cell monolayer can be a Vero cell monolayer, or other appropriate cell that can be infected by the target virus and express the reporter. In certain aspects the cell monolayers are assayed in a multi-well plate, such as a 96 well microtiter plate. In particular aspects the inoculated cells are incubated for about 12, 24, 36, or 48 hours before measuring the reporter signal.

The assays described herein can be used to detect multiple viruses, such as dengue virus. The assay can further comprising: (e) contacting a sample from a subject suspected of having a *flavivirus* infection with a reporter dengue virus (rDENV), the rDENV configured to produce a detectable signal when infecting a viable cell, forming a reporter mixture and incubating the reporter mixture at a temperature of 35 to 40° C.; (f) contacting a host cell monolayer with the reporter mixture under cell growth conditions at about 37° C. forming an inoculated cell monolayer; (g) measuring the reporter signal produced by the inoculated cell monolayer and normalizing the measured signal to a control; and (h) calculating a DENV antibody titer of the sample using the reporter signal measurements.

In other aspects the assay procedure can further comprising performing virus specific DNA amplification using a second sample from the subject suspected of having a *flavivirus* infection. In certain aspects the DNA amplification is a viral RT-PCR assay.

Embodiments of the invention are directed to stable full-length cDNA clones of a clinical, Asian lineage ZIKV strain. The cDNA clone-derived ZIKV described herein was virulent and caused neurological disease in A129 and AG129 mice. Furthermore, the recombinant virus was highly infectious for *A. aegypti* mosquitoes. These experimental systems are essential to study viral pathogenesis and vector transmission as well as to develop a ZIKV vaccine.

Certain embodiments are directed to a reverse genetic system of Zika virus. This system has three major applications. (1) Vaccine development for both inactivated vaccine and attenuated vaccine. (2) Therapeutics development through reporter virus and high throughput screening. (3) Novel diagnostics development using reporter virus and engineered reporter virus.

In certain aspects the ZIKV nucleic acids can have at least 90, 95, 98, 99, 99.99, 99.991 or 100% sequence identity to SEQ ID NO:1 or any 10, 20, 30, 40, 50, 100, 200, 300, 400, 500, 600, 700, 800, 1000, 2000, 3000, 4000, 5000, 6000, 7000, 8000, 9000, 10000, 11000 consecutive nucleotide segment thereof, including all values and ranges there between. In certain aspects, a nucleic acid comprises a nucleotide sequence that is at least 90, 95, 98, 99, or 100% identical to all or a part of the non-structural protein coding region of ZIKV (nucleotides 2490 to 10376 of SEQ ID NO:1, or any 10, 20, 30, 40, 50, 100, 200, 300, 400, 500, 600, 700, 800, 1000, 2000, 3000, 4000, 5000, 6000, or 7000 consecutive nucleotide segment thereof, including all values and ranges there between). In a further aspect, a nucleic acid comprises a nucleotide sequence that is at least 90, 95, 98, 99, or 100% identical to all or a part of the structural protein coding region of ZIKV (nucleotides 474 to 2489 of SEQ ID NO:1, or any 10, 20, 30, 40, 50, 100, 200, 300, 400, 500, 600, 700, 800, 1000, 2000, 3000, 4000, 5000, 6000, 7000, 8000, 9000, or 10000 consecutive nucleotide segment thereof, including all values and ranges there between).

The ZIKV nucleic acids can be isolated or recombinant nucleic acids (e.g., DNA) or included in a recombinant *flavivirus* replicon, a virus, a *flavivirus*, a viral particle, a *flavivirus* particle, an expression cassette, a host cell, a *flavivirus* vector, and the like. In still a further aspect, an *flavivirus* nucleic acid sequence can comprise a heterologous nucleic acid segment. In certain aspects, the heterologous nucleic acid segment can encode a therapeutic protein, an antigen, a toxin, or a marker (e.g., a reporter protein). In certain aspects the reporter protein is a fluorescent protein, such as a green fluorescent protein.

Certain aspects are directed to an isolated, recombinant, and/or purified ZIKV polypeptide or peptide having at least 90, 95, 98, 99, or 100% amino acid sequence identity to all or part of the amino acid sequence of SEQ ID NO:3 (ZIKV polyprotein). The term "polyprotein" refers to a polypeptide that is post-translationally cleaved to yield more than one polypeptide. "Polypeptide" refers to any peptide or protein comprising a chain or polymer of amino acids joined to each other by peptide bonds. "Polypeptide" refers to both short chains of 100 amino acids or less, commonly referred to as peptides, and to longer chains, generally referred to as proteins. In certain aspects, the isolated and/or purified ZIKV protein has at least 85, 90, 95, 98, 99, or 100% amino acid sequence identity to all or part of the amino acid sequence of an ZIKV non-structural protein. In certain aspects the Zika genome will be mutated to encode one or more amino acids that are associated with microcephaly.

Other embodiments are directed to flaviviruses comprising all or part of the ZIKV nucleic acid sequence of SEQ ID NO: 1. In certain aspects the *flavivirus* is a recombinant *flavivirus*. Certain embodiments are directed to a *flavivirus* having a genome comprising (a) an *flavivirus* nucleic acid segment that is at least 95, 98, 99, or 100% identical to SEQ ID NO:1 and (b) a heterologous nucleic acid segment. In certain aspects, the *flavivirus* is chimeric and comprises segments of a ZIKV *flavivirus* and corresponding segments from a another ZIKV strain or a non-ZIKV *flavivirus*.

As used herein, "control" or "suitable control" is an alternative subject or sample used in an experiment for comparison purposes and included to minimize or distinguish the effect of variables other than an independent variable. A "control" can be positive or negative. A "control" as used herein refers to a control that will allow determination of the presence of a virus or viral infection in a subject. "Control" includes a characteristic or other parameter in a treated sample before administration of a component described herein or before a detection regimen. "Control" can represent a normal level of the parameter being measured in a subject or sample.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

The term "recombinant" refers to an artificial combination of two otherwise separated segments of nucleic acid, e.g., by chemical synthesis or by the manipulation of isolated segments of nucleic acids by genetic engineering techniques.

The term "*flavivirus*" has its conventional meaning, and includes the various species of flaviviruses, including West Nile virus, dengue virus, tick-borne encephalitis virus, yellow fever virus, Zika virus and several other viruses which may cause encephalitis.

The term "*flavivirus* replicon" is used to refer to a nucleic acid molecule expressing *flavivirus* nonstructural protein genes such that it can direct its own replication (amplification).

The term "*flavivirus* replicon particle" refers to a virion or virion-like structural complex incorporating a *flavivirus* replicon.

The term "reporter virus" refers to a virus that is capable of directing the expression of a sequence(s) or gene(s) of interest. The reporter construct can include a 5' sequence capable of initiating transcription of a nucleic acid encoding a reporter molecule or protein such as luciferase, fluorescent protein, Neo, SV2 Neo, hygromycin, phleomycin, histidinol, and DHFR. The reporter virus can be used an indicator of infection of a cell by a certain virus.

The term "expression vector" refers to a nucleic acid that is capable of directing the expression of a sequence(s) or gene(s) of interest. The vector construct can include a 5' sequence capable of initiating transcription of a nucleic acid, e.g., all or part of a *flavivirus*. The vector may also include nucleic acid molecule(s) to allow for production of virus, a 5' promoter that is capable of initiating the synthesis of viral RNA in vitro from cDNA, as well as one or more restriction sites, and a polyadenylation sequence. In addition, the constructs may contain selectable markers such as Neo, SV2 Neo, hygromycin, phleomycin, histidinol, and DHFR. Furthermore, the constructs can include plasmid sequences for replication in host cells and other functionalities known in the art. In certain aspects the vector construct is a DNA construct.

"Expression cassette" refers to a nucleic acid segment capable of directing the expression of one or more proteins or nucleic acids.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

Viral titers from culture supernatants at indicated time points were determined by plaque assay. (D) Cytopathic effect on Vero cells on day 6 post transfection.

Figure 3:
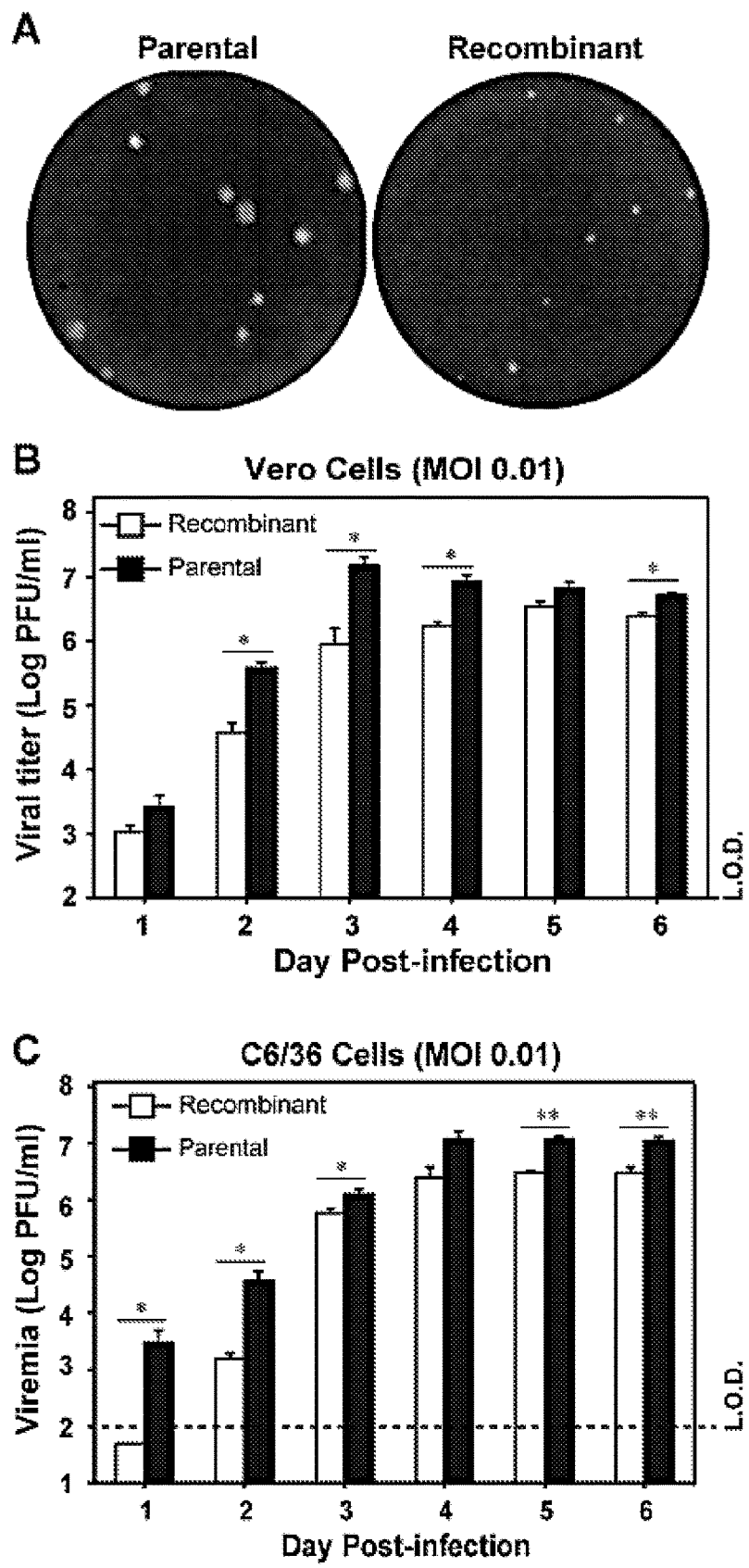

FIG. 3. Characterization of parental and recombinant ZIKVs in cell culture. (A) Plaque morphology of parental and recombinant ZIKVs. (B and C) Comparison of growth kinetics in Vero and C6/36 cells, respectively. Vero and C3/36 cells were infected with parental and recombinant virus at an MOI of 0.01. Viral titers were measured at indicated time points using plaque assays on Vero cells. Means and standard deviations from three independent replicates are shown. Statistics were performed using unpaired student's t-test. *significant (p value<0.05); **highly significant (p value<0.01). L.O.D., limitation of detection (100 PFU/ml).

Figure 4:
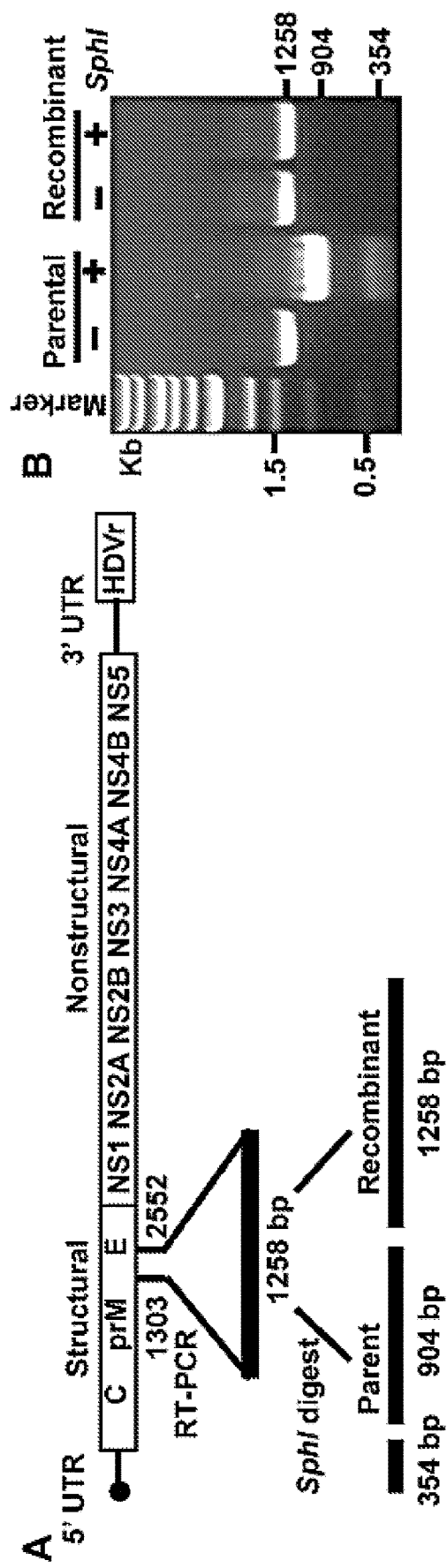

FIG. 4. A genetic marker was engineered in the recombinant ZIKV. An SphI cleavage site, located in the viral E gene of parental virus, was knocked out in the cDNA clone to serve as a genetic marker to distinguish between recombinant virus and parental virus. A 1258-bp fragment (from nucleotides 1,303 to 2,552) spanning the SphI site was amplified using RT-PCR from RNA extracted from either recombinant virus or parental virus. The RT-PCR fragments were subjected to SphI digestion. The 1258-bp fragment derived from recombinant virus should not be cleavable by SphI; whereas the RT-PCR fragment amplified from parental viral RNA should be cleavable by SphI. (A) Schematic drawing of SphI restriction enzyme analysis. The expected sizes of the digestion products are indicated. (B) Agarose gel analysis of SphI digestion products. Expected digestion pattern as depicted in panel (A) was observed.

Figure 5:
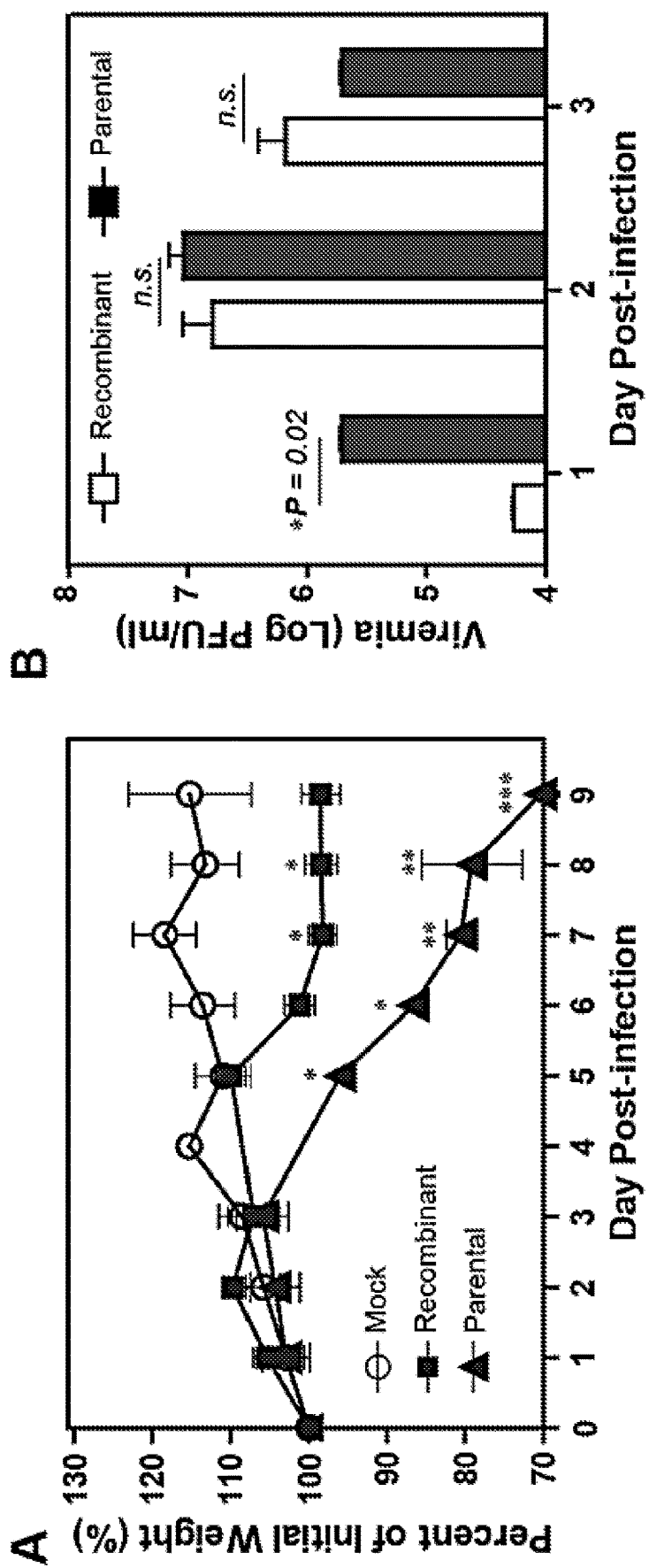

FIG. 5. Comparison of virulence in A129 mice between recombinant and parental viruses. Four-week-old A129 mice were infected with $1\times10^5$ PFU per individual via the intraperitoneal route. Mock or infected mice (n=5 per group) were monitored for weight loss (A). The viremia at the first three days p.i. was quantified using plaque assay (B). Means and standard deviations are shown. Statistics were performed using unpaired student's t-test. *significant (p value<0.05); highly significant (p value<0.01); *extremely significant (p value<0.001).

Figure 6:
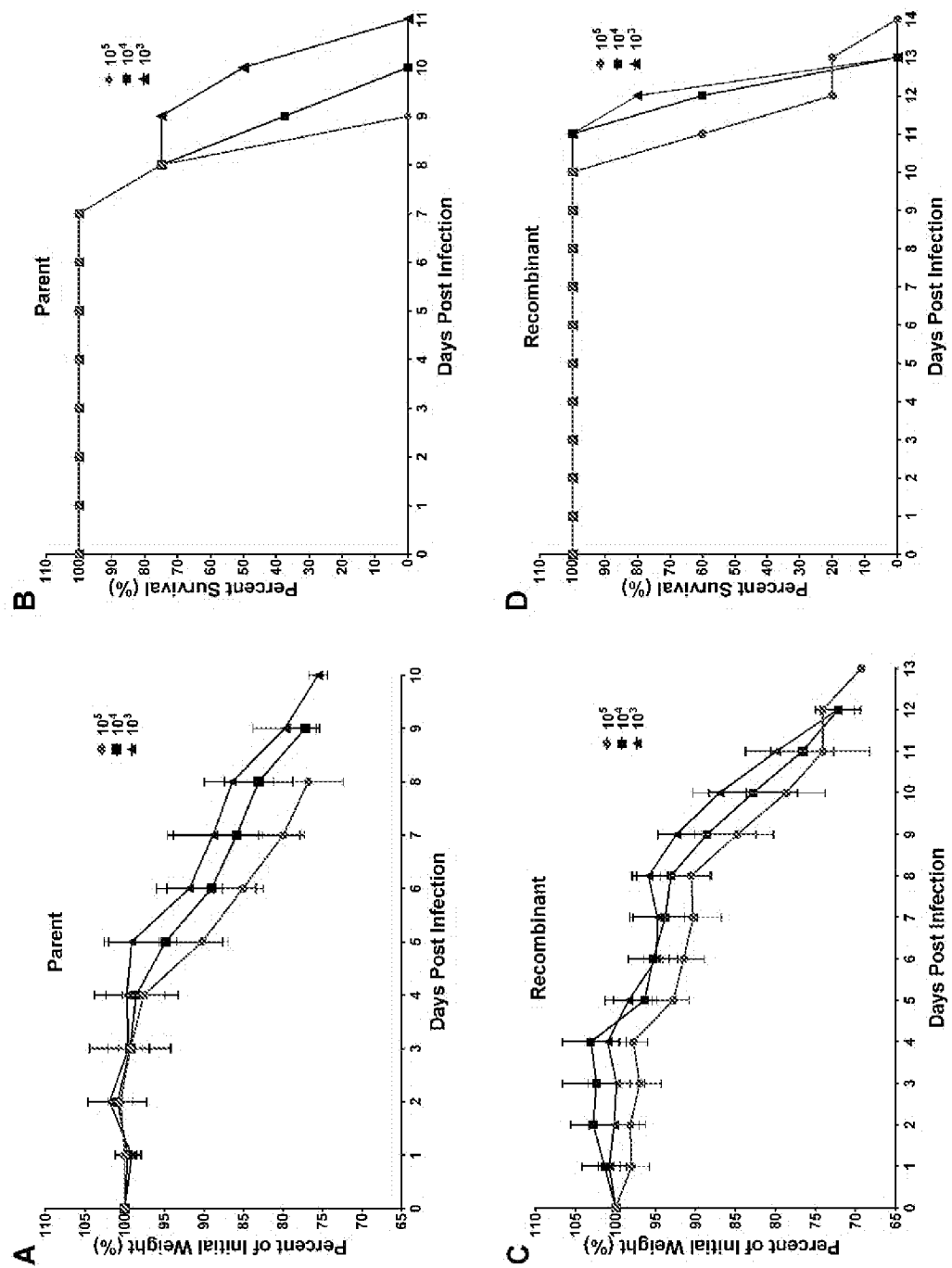

FIG. 6. Virulence of parental and recombinant ZIKVs in AG129 mice. Six week-old AG129 mice were inoculated by intraperitoneal injection with $1\times10^5$ PFU (n=4 for parental virus; n=5 for recombinant virus), $1\times10^4$ PFU (n=8 for parental virus; n=5 for recombinant virus), or $1\times10^3$ PFU (n=4 for parental virus; n=5 for recombinant virus) of ZIKV. The infected mice were monitored for weight loss. Mice were euthanized once weight loss exceeded >20%. For each infection dose, weight loss and survival curves are presented. Parental and recombinant viruses and their infection doses are indicated. Values are mean percent weight compared to initial weight.

Figure 7:
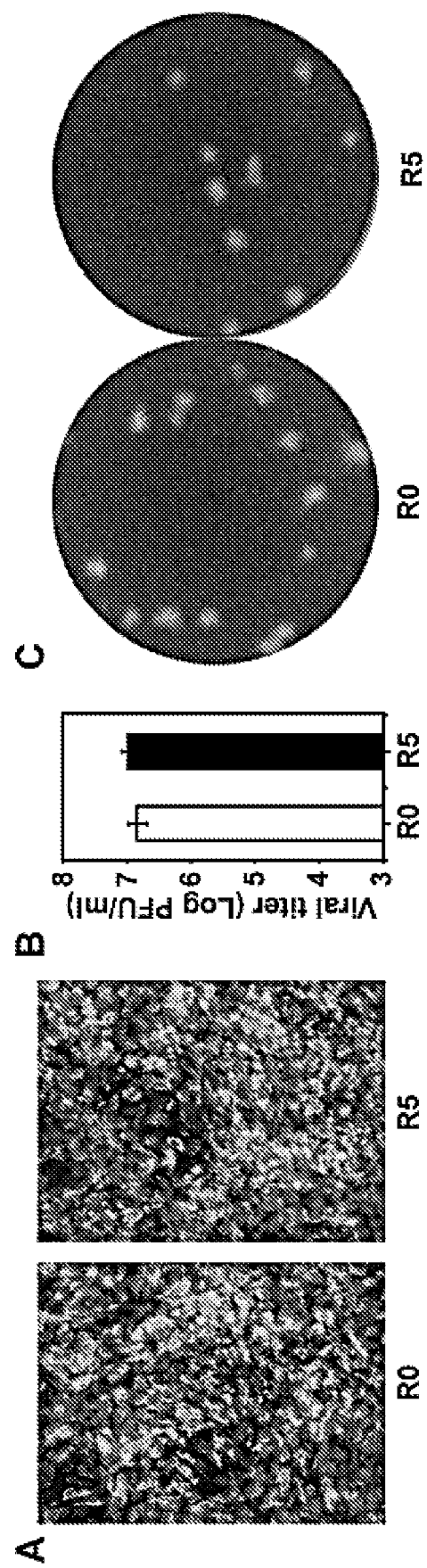

FIG. 7. The ZIKV infectious cDNA clone (pFLZIKV) is stable. pFLZIKV was propagated for five rounds of plasmid transformation, bacterial growth, and plasmid purification. Plasmid purified from round 5 was used to transcribe RNA for infectivity test. (A) IFA of viral E protein expression in cells transfected with pFLZIKV RNA from round 0 (R0) and round 5 (R5). Vero cells were electroporated with 10 μg of genome-length RNAs of ZIKV. On day 6 p.t., IFA was performed to examine the E protein expression using a mouse mAb (4G2). Green and blue represent E protein and nuclei staining, respectively. (B) Yields of R0 and R5 ZIKVs on day 6 post-transfection. Culture fluids on day 6 p.t. were measured for infectious viruses using plaque assay on Vero cells. (C) Plaque morphology of R0 and R5 recombinant ZIKVs.

FIG. 8. Amino acid sequence encoded by SEQ ID NO:1 with amino acid differences of polyprotein as compared to polyprotein encoded by Zika viruses associated with microcephaly highlighted by bold underline.

Figure 9:
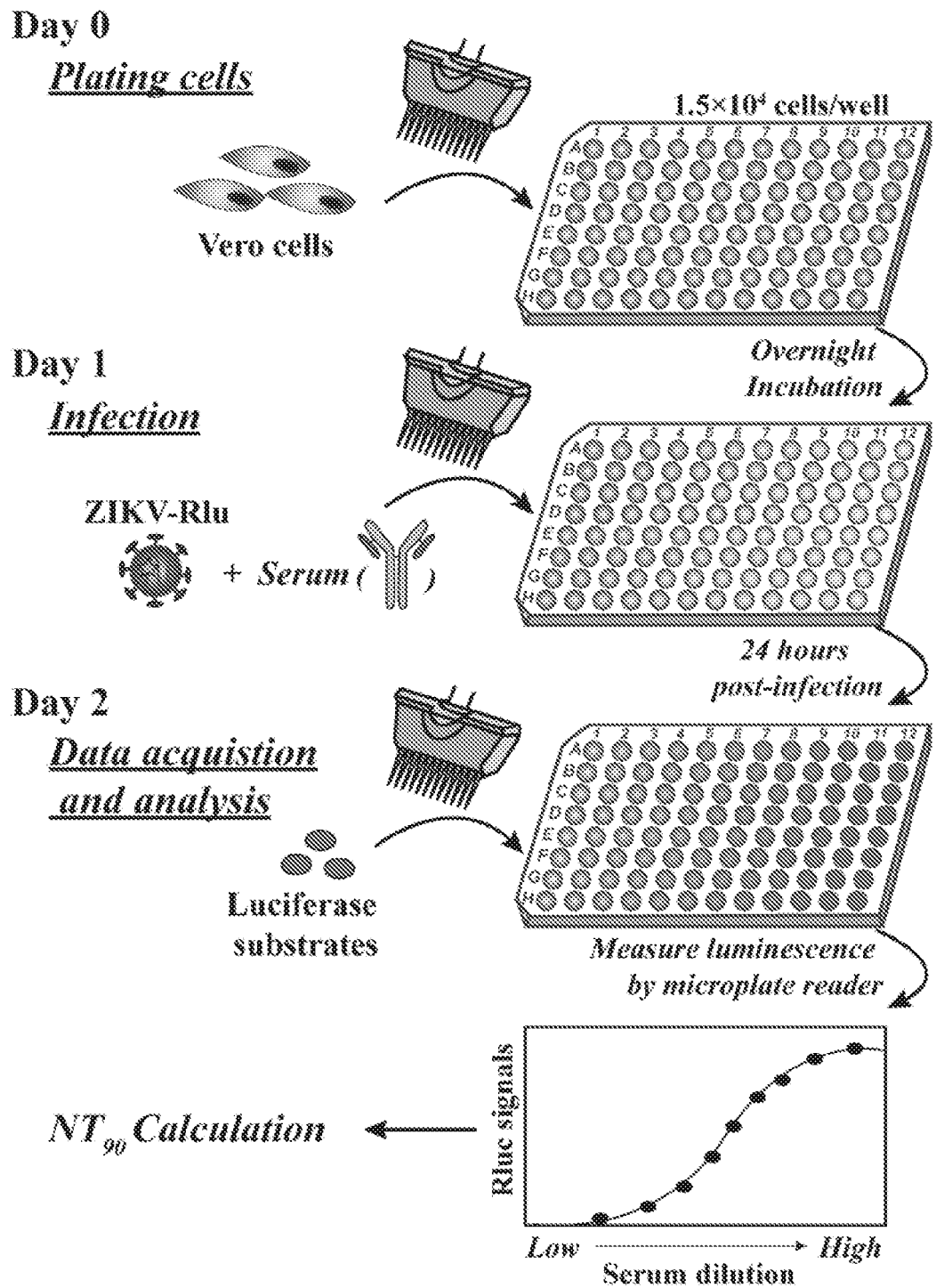

FIG. 9. Experimental scheme of reporter virus-based infection assay to measure neutralization titers of specimens. See text for details.

Figure 10:
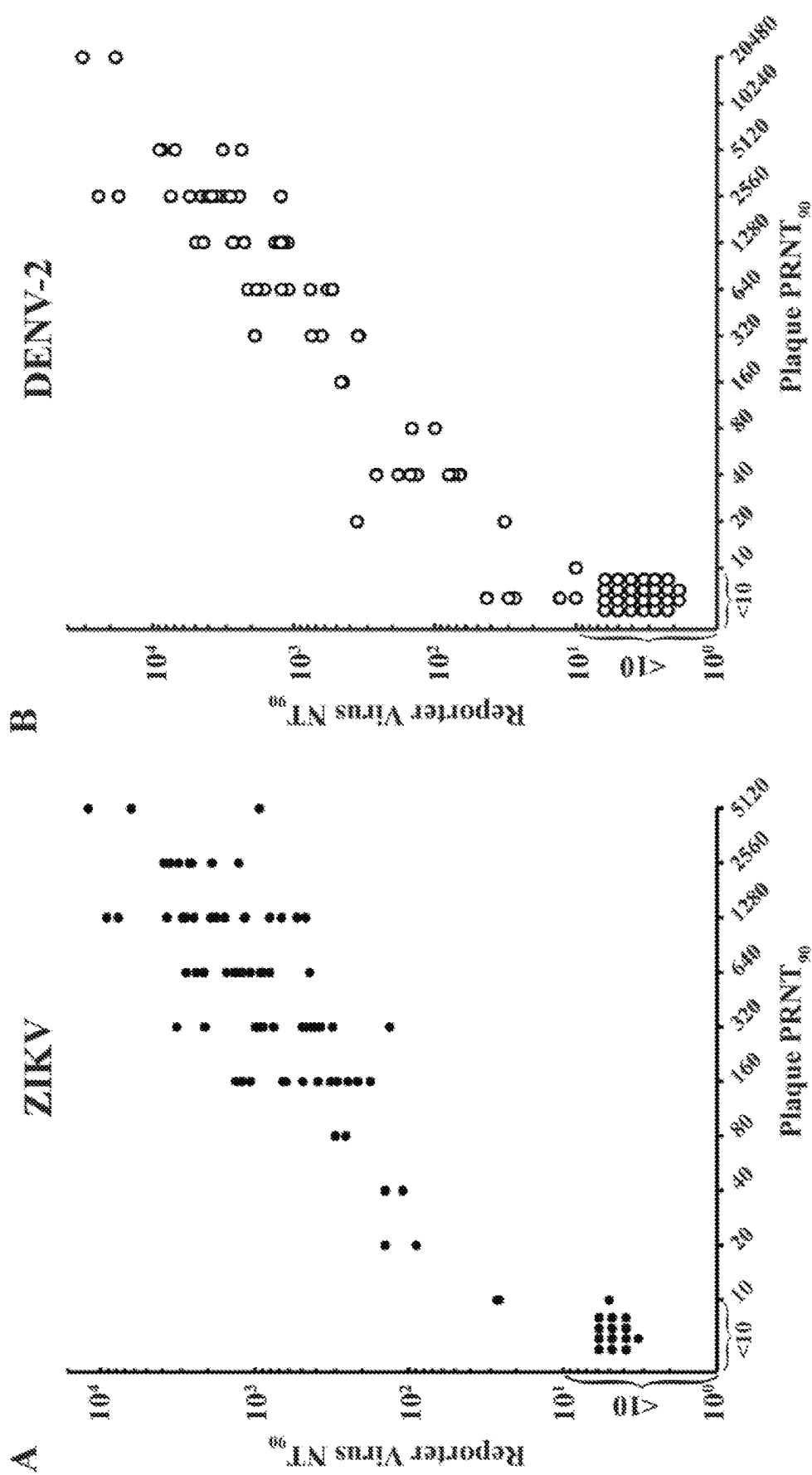

FIG. 10. Scatter plots of plaque assay-derived $PRNT_{90}$ and reporter assay-derived $NT_{90}$ values for ZIKV and DENV.

Figure 1:
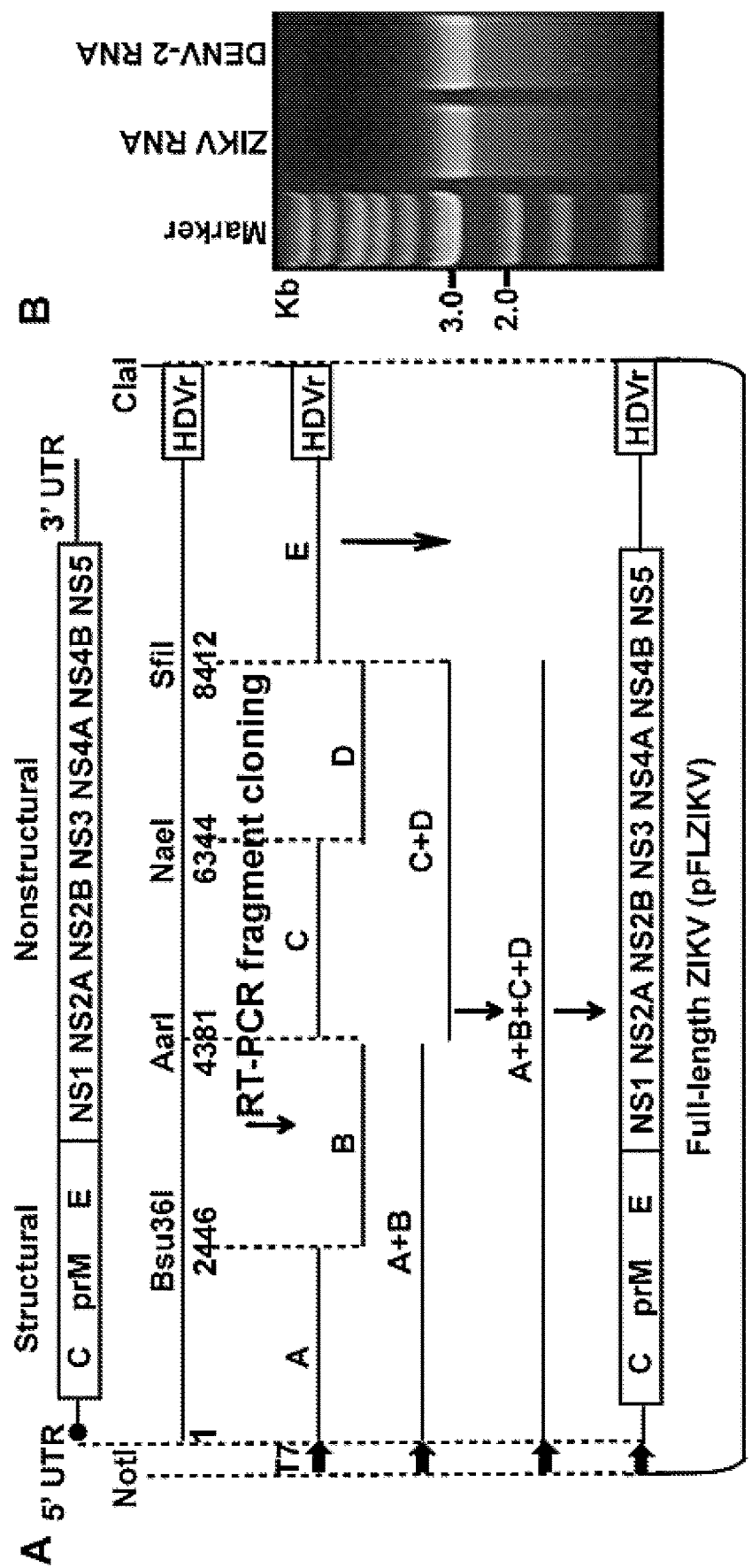
FIG. 1. Construction of the full-length cDNA clone of ZIKV. (A) The strategy for constructing the full-length cDNA clone of ZIKV. Genome organization, unique restriction sites, and their nucleotide positions are shown. Five cDNA fragments from A to E (represented by thick lines) were synthesized from genomic RNA using RT-PCR to cover the complete ZIKV genome. Individual fragments were assembled to form the full-length cDNA clone of ZIKV (pFLZIKV). The complete ZIKV cDNA is positioned under the control of T7 promoter elements for in vitro transcription. An HDVr ribozyme sequence was engineered at the 3' end of viral genome to generate an authentic 3' end of viral RNA sequence. The numbers are the nucleotide positions based on the sequence of ZIKV strain FSS13025 (GenBank number JN860885). (B) Analysis of RNA transcript from pFLZIKV on a native agarose gel. A 0.8% agarose gel electrophoresis was used to analyze ZIKV RNA transcript along with a genome-length DENV-2 RNA.
Figure 11:
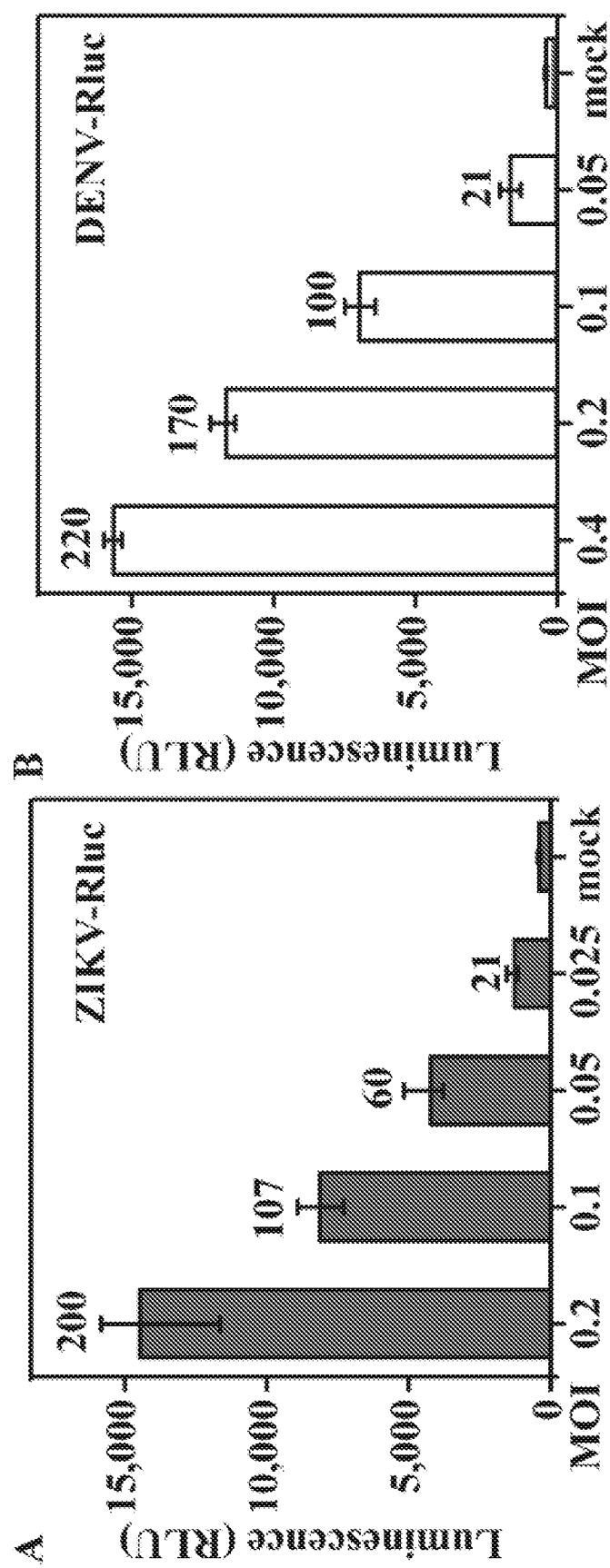

FIG. 11. Optimization of the inoculums of Renilla luciferase (Rluc) ZIKV (A) and DENV-2 (B) for the neutralization assay. The experimental scheme is depicted in FIG. 1 and the protocol is detailed in Materials and Methods. Different MOIs of virus inoculum and their luciferase activities at 24 h post-infection are presented. Ratios of the luciferase signals derived from the infections versus the signals from the mock-infected cells are indicated above the bars representing luciferase signals. The average results of three independent experiments are presented.

DESCRIPTION

Since its first isolation in Uganda in 1947 (Dick et al., (1952). *Transactions of the Royal Society of Tropical Medicine and Hygiene* 46, 509-20), ZIKV has predominantly been associated with sylvatic transmission cycles between primates and arboreal mosquitoes in forests, and has for six decades rarely caused human diseases, with only 13 naturally acquired cases reported (Petersen et al., (2016) Zika Virus, *N Engl J Med*). Up to 80% of infected people are asymptomatic. Signs and symptoms of ZIKV infection include fever, lethargy, conjunctivitis, rash, and arthralgia. However, in the past decade, ZIKV has emerged into urban transmission cycles between humans and mosquitoes in the South Pacific and the Americas, and has caused severe diseases, including Guillain-Barré Syndrome and congenital microcephaly (Fauci and Morens, (2016) Zika Virus in the Americas—Yet Another Arbovirus Threat, *N Engl J Med*).

Phylogenetic analysis indicates ZIKV exists as African and Asian lineages. The Asian lineage is responsible for the recent/current epidemics: it caused an epidemic on Yap Island, Micronesia in 2007; it then spread from an unknown source, probably in Southeast Asia, to French Polynesia and other regions of the South Pacific and caused large epidemics in 2013-14; subsequently, ZIKV arrived in the Americas in 2015 and led to millions of human infections (Weaver et al., (2016) *Antiviral Res* 130, 69-80; Weaver et al., (2016) Zika Virus: History, Emergence, Biology, and Prospects for Control, *Antiviral Res*). It is currently not known what has triggered the surge of recent epidemics and severe diseases.

Zika virus (ZIKV) exists as two main lineages: African and Asian. After its discovery in 1947, ZIKV remained obscure with few human cases identified and mild disease symptoms. However, since 2007, the Asian lineage has caused frequent epidemics associated with severe symptoms such as microcephaly and Guillain-Barré syndrome. Unraveling the mechanisms of increased transmissibility and disease severity requires a number of experimental systems, including a reverse genetic system of ZIKV, animal models, and viral vector competence. An infectious cDNA clone of ZIKV using a clinical isolate of Asian lineage (with >99% amino acid identity to the epidemic American strains) is described herein. The RNA transcribed from the cDNA clone was highly infectious upon transfection into Vero cells, generating recombinant ZIKV with titers of 2-8×10$^6$ PFU/ml. A genetic marker was engineered into the recombinant virus to differentiate it from the parental and other ZIKV strains. The recombinant virus was virulent in A129 and AG129 mice, and infected mice developed neurological signs that are relevant to human diseases. Furthermore, the recombinant ZIKV was highly infectious for *Aedes aegypti* (the presumed urban American vector) with a dissemination rate of 58% after blood meals containing approximately 10$^6$ PFU/ml of recombinant virus, suggesting that this mosquito is an efficient vector. Collectively, the reverse genetic system of ZIKV, together with the mouse and mosquito infection models, represent a major advance towards deciphering potential viral determinants of human virulence and urban mosquito transmission. The genetic system will enable rapid development a vaccine using a target-based, rational design.

The current recommendation for diagnosis of ZIKV infection includes three main assays (Musso and Gubler, 2016 *Clin Microbiol Rev* 29, 487-524; Staples et al., 2016 Interim Guidelines for the Evaluation and Testing of Infants with Possible Congenital Zika Virus Infection—United States, 2016. *MMWR Morb Mortal Wkly Rep* 65, 63-67). (i) Detection of viral RNA by RT-PCR. The RT-PCR assay is relatively straightforward and reliable with good sensitivity and specificity (Lanciotti et al., 2008 *Emerg Infect Dis* 14, 1232-39). (ii) Detection of ZIKV-reactive IgM antibodies by an ELISA. One major weakness of the current IgM ELISA test is cross-reactivity with other flaviviruses (such as DENV). This is because the assay uses only viral structural proteins (e.g., E protein) which are the major antigenic proteins known to illicit cross-reactive antibodies. To reduce the assay cross reactivity, one could include viral non-structural proteins in the ELISA. This idea is based on the rationale that, during *flavivirus* infection, antibody response to viral nonstructural proteins may be more virus-type specific than that to structural proteins. Indeed, several studies reported that *flavivirus* NS1, NS3, and NS5 could be used to improve the specificity of serologic diagnosis (Garcia et al., 1997 *American Journal of Tropical Medicine & Hygiene* 56:466-70; Shu et al., 2000 *Journal of Medical Virology* 62:224-32; Stettler et al., 2016 *Science* 353:823-26; Wong et al. 2003 *J Clin Microbiol* 41:4217-23). In support of this rationale, a multiplex Luminex assay employing ZIKV E, NS1, and NS5 was recently shown to significantly improve the assay specificity (Wong et al., 2017 *E Bio Medicine*). However, it should be pointed out that, although cross reactivity against ZIKV NS1 and NS5 is lower than that against E protein, residual cross reactivity remains to be eliminated for further improvement. This could be achieved through antigen engineering (applicable to both structural and non-structural proteins) to remove the cross-reactive epitopes. The antigen engineering could be rationally guided by protein structures and their epitope profiles. Employment of such virus-specific proteins without cross-reactive epitopes will further improve the assay specificity. (iii) Confirmation of the IgM ELISA-positive specimens using a PRNT assay. Although PRNT remains the "gold standard" for arbovirus serology, the low-throughput nature of the assay limits the number of samples that could be diagnosed in a timely manner. This limitation is particularly pressing in ZIKV diagnosis for pregnant patients.

Embodiments of the invention described herein are directed to a rapid assay to replace the traditional plaque-based PRNT assay. The inventors took advantage of their previously constructed luciferase reporter ZIKV and DENV, and developed a homogeneous neutralization assay in a 96-well format. Validation of the reporter assay using 91 human sera generated diagnostic results equivalent to the traditional PRNT. Importantly, the reporter assay has significantly improved test turnaround time, assay dynamic range, and diagnostic throughput. These improvements have practical implications in clinics by overcoming the bottleneck of test capacity and by achieving test results within 48 hours. Since the current diagnostic algorithm is to confirm the IgM ELISA-positive specimens using PRNT, the reporter assay may be used directly to test neutralization titer of patient samples without prior IgM ELISA. In this way, the reporter assay could serve in conjunction with RT-PCR as the first-line test for ZIKV serologic diagnosis from which physicians would be able to attain the diagnostic results within two days. Furthermore, the reporter assay could be used to specifically measure IgM or IgG neutralization titers when other antibody types have been pre-depleted from the patient sera.

The reporter virus-based neutralization assay can be expanded to other flaviviruses (Zhang et al., 2016 *Virus Res* 211:17-24) as well as to other arboviruses (such as chikungunya virus) that often co-circulate in many tropical and sub-tropical regions. Besides the use in clinical diagnosis, reporter viruses could also be useful for other aspects of research, such as tracking infection in mosquitos and in small animal models (Schoggins et al., 2012 *Proc Natl Acad Sci USA* 109:14610-15), as well as for siRNA/CRISPR library screening or antiviral drug discovery (Puig-Basagoiti et al., 2005 *Antimicrob Agent Chemother* 49:4980-88). For serologic diagnosis, the reporter viruses are superior to trans packaged virus-like particles using reporter replicons (Hanna et al., 2005 *J Virol* 79:13262-74; Harvey et al., 2004 *J Virol* 78:531-38; Khromykh et al., 1998 *J Virol* 72:5967-5977) because once stable reporter viruses have been established, they could be produced in large quantities.

The inventors have developed a reporter ZIKV assay that can replace the current "gold standard" PRNT assay to measure neutralization titers of patient specimens. Since the assay is high throughput and has a turnaround time of less than 48 h, it can be used as the first-line diagnostic test without prior IgM ELISA test. The reporter ZIKV assay can be readily used for clinical diagnosis, serologic surveillance, and monitoring antibody response in vaccine trial. This serologic assay, together with the well-established viral RT-PCR assay, can deliver a rapid diagnosis of ZIKV infection.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

An Infectious cDNA Clone of Zika Virus to Study Viral Virulence and Mosquito Transmission Construction of the Full-Length cDNA Clone of ZIKV.

The inventors chose a clinical ZIKV isolate of Asian lineage to construct the cDNA clone. This ZIKV strain (FSS13025) was isolated from a three-year old patient from Cambodia in 2010 (Heang et al., (2012) *Emerg Infect Dis* 18, 349-351). Viral RNA from Vero cell passage two of the isolate was sequenced (GenBank number JN860885.1) and used as the template to construct the infectious cDNA clone. Five RT-PCR fragments (A to E) spanning the complete viral genome were individually cloned and assembled into the full-length cDNA of ZIKV (named as pFLZIKV; FIG. 1A). Based on previous experience with infectious clones of other flaviviruses (Li et al. (2014) *J Gen Virol* 95, 806-15; Shi et al., (2002) *J Virol* 76, 5847-56; Zou et al., (2011) *Antiviral Res* 91, 11-19), the inventors chose a low-copy number plasmid pACYC177 (15 copies per *E. coli* cell) to clone fragments A and B as well as to assemble the full-genome cDNA. This plasmid was used because fragments A and B, spanning the viral prM-E-NS1 genes, were toxic to *E. coli* during the cloning procedure; high copy-number vectors containing these fragments were unstable, leading to aberrant deletions/mutations of the inserts (Shi et al., (2002) *J Virol* 76, 5847-56). In contrast, fragments C, D, and E were not toxic to *E. coli*, and could be cloned individually into a high copy-number plasmid pCR2.1-TOPO. A T7 promoter and a hepatitis delta virus ribozyme (HDVr) sequence were engineered at the 5' and 3' ends of the complete viral cDNA for in vitro transcription and for generation of the authentic 3' end of the RNA transcript, respectively. Sequence comparison of the fully assembled pFLZIKV cDNA with the parental virus revealed two synonymous mutations in the E gene (Table 1), one of which was derived from an engineered genetic marker (see below). RNA synthesized from the pFLZIKV plasmid (10,808 nucleotides [nt] long without HDVr) and RNA transcribed from a DENV-2 infectious clone (10,723 nt long; (Zou et al., (2011) *Antiviral Res* 91, 11-19)) migrated similarly on a native agarose gel (FIG. 1B).

TABLE 1

Sequence differences between the infectious cDNA clone and parental ZIKV[a]

| Nucleotide position | Parental strain | cDNA clone | Amino acid change | Location |
|---|---|---|---|---|
| 1655 | T | C | Silent (SphI knockout) | E |
| 1865 | T | C | None | E |

[a]ZIKV strain FSS13025 (GenBank number JN860885.1) was used in the current study. After sequencing this strain FSS13025, we found an error in the current GenBank sequence. The sequence at nucleotide position 798 should be T, not C.

RNA Transcript from ZIKV cDNA Clone is Highly Infectious.

Figure 2:
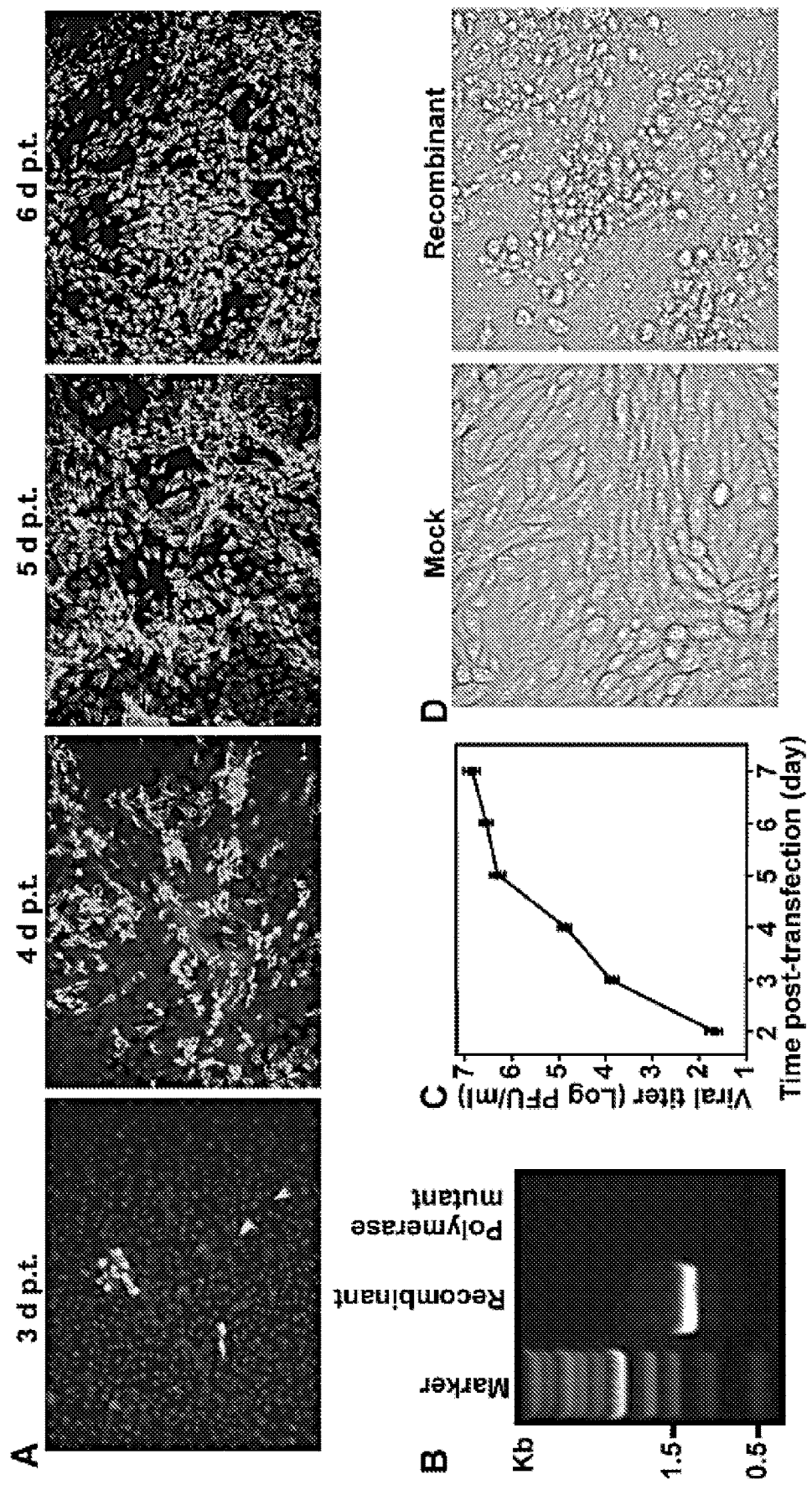
FIG. 2. The RNA transcript from pFLZIKV is infectious. (A) IFA of viral protein expression in cells transfected with full-length ZIKV RNA. Vero cells were electroporated with 10 µg of genome-length ZIKV RNA. From day 3 to 6 post transfection (p.t.), IFA was performed to examine viral E protein expression using a mouse mAb (4G2). Green and blue represent E protein and nuclei (stained with DAPI), respectively. (B) RT-PCR analysis of progeny viral RNA. Viral RNA was extracted from culture supernatant on day 6 p.t. and used as a template for RT-PCR using ZIKV-specific primer pair 1303-F and 2552-ClaI-R (Table 4). As a negative control, a genome-length RNA containing an NS5 polymerase active site mutation (GDD mutated to AAA) was included. (C) Yield of infectious ZIKV after transfection.

The pFLZIKV RNA transcript was transfected into Vero cells to examine the infectivity of the cDNA clone. The transfected cells were monitored for viral protein expression, RNA synthesis, and virus production. As shown in FIG. 2A, an increasing number of cells expressed viral E protein from day 1 to 6 post-transfection (p.t.). RT-PCR analysis detected ZIKV RNA in culture media of the transfected cells; as a negative control, no RT-PCR product was detected from the cells transfected with an RNA containing the polymerase active site GDD residues mutated to AAA (FIG. 2B). Increasing amounts of infectious virus were produced from the wild-type RNA-transfected cells, with peak titers of $1\times10^{6-7}$ plaque-forming units (PFU)/ml on days 5-7 (FIG. 2C). On days 6-7 p.t., the transfected cells exhibited cytopathic effects (CPE; FIG. 2D). Full-genome sequencing of the recombinant virus revealed no change other than the two synonymous mutations that originated from pFLZIKV. Collectively, these results demonstrate that the ZIKV cDNA clone is highly infectious.

Comparison of Cell Culture Growth Between Parental and Recombinant Viruses.

The recombinant and parental viruses were compared in cell culture. As shown in FIG. 3A, the recombinant virus produced homogeneous plaque morphology, whereas the parental virus generated heterogeneous plaque sizes. The difference in plaque morphology was not surprising because the recombinant viruses were derived from a homogenous population of RNA transcripts, whereas the parental virus presumably was composed of a quasi-species. In agreement with this notion, the recombinant virus displayed attenuated replication kinetics in both mammalian Vero and mosquito C6/36 cells (FIG. 3B and FIG. 3C), indicating that the replication level of recombinant virus was attenuated in cell culture.

Recombinant ZIKV Retained an Engineered Genetic Marker.

To exclude the possibility that the recovered recombinant virus represented contamination with the parental virus, the inventors engineered a genetic marker into the recombinant virus, in which an SphI cleavage site in the E gene from the parental virus was eliminated (FIG. 4A). A 1,257-bp fragment spanning nucleotides 1,301-1,252 of viral genome was amplified using RT-PCR from RNAs extracted from the parental and recombinant viruses. The RT-PCR product from the parental virus was readily cleaved by SphI, whereas the RT-PCR product from the recombinant virus was resistant to SphI digestion (FIG. 4B). These results demonstrate that the recombinant virus was produced from the cDNA-derived RNA transcript. The genetic marker allows differentiation and quantification between the recombinant virus and potentially other ZIKV isolates (which have the SphI site); it could be used to study viral fitness when the recombinant virus serves as an internal standard to gauge viral fitness of other ZIKV strains in a competition assay (Fitzpatrick, et al., (2010) *Virology* 404, 89-95).

The Infectious cDNA Clone of ZIKV is Stable.

Since infectious cDNA clones of flaviviruses are known to be unstable and deleterious for bacterial host (Khromykh and Westaway, (1994) *Journal of Virology* 68, 4580-88; Lai et al., (1991) *PNAS USA* 88, 5139-43; Mandl et al., (1997) *Journal of General Virology* 78, 1049-57; Rice et al., (1989) *New Biologist* 1, 285-96; Sumiyoshi et al., (1992) *Journal of Virology* 66, 5425-31), the stability of pFLZIKV was examined through five rounds of plasmid transformation, bacterial growth, and plasmid purification. Plasmid purified from round 5 was used to transcribe RNA for an infectivity testing. Transfection of the $5^{th}$ round RNA into Vero cells generated viral E protein-expressing cells (FIG. 7A) and infectious virus (FIG. 7B) at levels equivalent to those derived from the original pFLZIKV RNA without passaging (FIGS. 7A and 7B). Similar plaque morphology was observed for the original and $5^{th}$ round RNA-derived recombinant viruses (FIG. 7C). These results demonstrate the stability of the ZIKV infectious clone.

Virulence in A129 and AG129 Mice.

The inventors compared the virulence of the parental and recombinant ZIKVs in two mouse models: A129 (lacking interferon α/β receptor) and AG129 (lacking interferon α/β and γ receptors). The AG129 mice have recently been reported to be more susceptible to ZIKV-induced disease than the A129 mice (Rossi et al., (2016) Characterization of a Novel Murine Model to Study Zika Virus, Am J Trop Med Hyg). In the A129 mice, intraperitoneal (i.p.) infection with parental virus ($10^5$ PFU) led to weight loss and disease characterized by hunched posture and ruffled fur; all infected mice were euthanized due to >20% weight loss on day 9 post-infection (p.i.; FIG. 5A). In contrast, infection with the same inoculum of recombinant ZIKV resulted in less weight loss, but none of the infected mice died (FIG. 5A). In agreement with these observations, the recombinant virus generated significantly lower viremia than the parental virus on day 1 p.i. in the A129 mice; whereas the differences on days 2 and 3 viremia were not statistically significant between the two viruses (FIG. 5B). The results suggest that the slower replication kinetics of the recombinant virus may be responsible for its attenuated virulence.

In AG129 mice, i.p. injection of both parental and recombinant ZIKVs ($1\times10^{3-5}$ PFU) led to neurological disease, weight loss, and death (due to >20% weight loss; FIG. 6). The neurological disease was characterized by hyperactivity, uncoordinated movements, inability to right the body, body spinning, and hind limb paralysis. The kinetics of weight loss was dependent on the viral dose: mice infected with the recombinant virus exhibited slower weight loss and longer survival than those infected with the parental virus (FIG. 6). These results demonstrate that the recombinant virus is less virulent than the parental virus in vivo; however, infection AG129 mice with the recombinant virus still leads to neurological disease, consistent with evidence that ZIKV causes congenital neurodevelopmental disorders in human fetuses.

Mosquito Infection and Dissemination.

To compare viral fitness between parental and recombinant viruses in mosquitoes, the inventors determined the oral susceptibility of *A. aegypti* using artificial human blood meals containing ZIKV. As summarized in Table 2, the recombinant virus showed higher infection and disseminated infection rates than the parental virus, which may have reflected the slightly higher blood meal titer of the recombinant virus. The overall dissemination rates (number of disseminated mosquitoes/number of infected mosquitoes× 100%) were equivalent between the parental and recombinant viruses, suggesting that the recombinant virus has a wild-type phenotype in *A. aegypti* mosquitoes. These results demonstrate that the recombinant virus is highly infectious for *A. aegypti*, and the disseminated infection rates suggest that this species is an efficient vector for ZIKV.

TABLE 2

Infection and dissemination of Asian lineage ZIKV strain FSS13025 (Cambodia, 2010) in *A. aegypti*

| Strain | Blood meal titer ($Log_{10}$ FFU/ml) | Infection rate (%)[a] | Disseminated infection rate (%)[b] | Dissemination rate (%)[c] |
|---|---|---|---|---|
| FSS13025 parental | 6.2 | 18/42 (43) | 11/42 (26) | 11/18 (61) |
| FSS13025 recombinant | 6.5 | 33/42 (78) | 19/42 (45) | 19/33 (58) |

[a]Infection rate = Number of infected mosquitoes/number of engorged mosquitos × 100%
[b]Disseminated infection rate = Number of disseminated mosquitos/number of engorged mosquitos × 100%
[c]Dissemination rate (%) = Number of disseminated mosquitos/number of infected mosquitos × 100%

The reverse genetic system described herein, together with the mosquito infection and A129/AG129 mouse models, provide a tractable platform to explore the mechanisms responsible for the explosive epidemics and increased disease severity of ZIKV infection since 2007. A number of non-exclusive mechanisms are possible. (i) ZIKV has undergone adaptive evolution that enhanced mosquito transmission, leading to rapid virus spread and an increased number of human infections. This hypothesis could be tested by comparisons of mosquito infectivity of the older ZIKV strains with recent isolates, followed by using the reverse genetic system to test the effects of recent mutations on mosquito transmission. This mechanism was responsible for the emergence of chikungunya virus, in which a series of mutations in the viral envelope genes enhanced viral transmission by *A. albopictus* through increased infection of epithelial cells in the midgut (Tsetsarkin et al. (2014) *Nature communications* 5, 4084; Tsetsarkin and Weaver, (2011) *PLoS Pathog* 7, e1002412). (ii) The Asian lineage of ZIKV has adapted to generate higher viremia in humans, leading to enhanced cross-placental infection and microcephaly. This hypothesis could be tested by engineering adaptive mutations from the recent isolates into the infectious cDNA clone, generating mutant viruses, and quantifying the mutational effect on viral virulence in the A129/AG129 mouse and on microcephaly development (the animal model for microcephaly remains to be established). (iii) Stochastic introduction of ZIKV into a population (in the Pacific and Americas) lacking herd immunity, leading to greater susceptibility to ZIKV infection and efficient mosquito transmission. Sero-prevalence and its correlation with ZIKV transmission and outbreak frequency need to be established to address this hypothesis. (iv) Previous infection with DENV may exacerbate ZIKV disease severity because the two viruses share approximately 43% amino acids identity and extensive antibody cross-reactivity (Alkan et al. (2015). *J Virol* 89, 11773-85; Lanciotti et al. (2008) *Emerg Infect Dis* 14, 1232-39). This hypothesis could be tested in the AG129 mouse because this mouse is susceptible to infection with both DENV and ZIKV. (v) Human genetic predisposition may account for the severe disease outcomes. Any viral infection is modulated by pro-viral and anti-viral host factors. The interaction between viral and host factors determines the efficiency of infection, pathogenicity, transmission, and epidemic potential. Therefore, variations of critical host factor(s) among infected individuals may contribute to different disease severity.

Compared with the parental virus, the replication efficiency of the recombinant virus was reduced in Vero and C6/36 cells (FIG. 3). This attenuated replication of recombinant virus in Vero cells was translated to the attenuated virulence in the A129 and AG129 mice (FIG. 5 and FIG. 6). The differences (in replication and virulence) between the parental and recombinant viruses could be due to the limited genetic heterogeneity of the recombinant virus population and the more genetically diverse quasi-species nature of the parental virus. Interestingly, although the replication of the recombinant virus was reduced in C6/36 cells, it yielded a disseminated infection rate in *A. aegypti* mosquitoes similar to that of the parental virus, indicating that the cell culture system does not necessarily recapitulate in vivo outcomes. Such a discrepancy is not surprising because of the more complex host-virus interactions in vivo.

The infectious cDNA clone of ZIKV will facilitate vaccine development through rational design. Target-based attenuation of ZIKV could be achieved through mutating viral replication components (viral RNA and replication complex) or through ablating viral components needed for evasion of host immune response (Li et al. (2013) *J Virol* 87, 5812-19; Whitehead et al., (2007) *Nat Rev Microbiol* 5, 518-28; Zust et al. (2013) *PLoS Pathog* 9, e1003521). The ZIKV strain used in the current study is appropriate for such attenuated vaccine because of its high sequence similarity to the American epidemic strains. As summarized in Table 3, only 19 amino acid differences were observed between the infectious clone-derived virus described herein and strains recently isolated from microcephaly fetuses (Calvet et al. (2016). Detection and sequencing of Zika virus from amniotic fluid of fetuses with microcephaly in Brazil: a case study, *The Lancet Infectious diseases*; Faria et al. (2016). Zika virus in the Americas: Early epidemiological and genetic findings. *Science*; Mlakar et al. (2016) N Engl J Med 374, 951-58), representing >99% amino acid identity. In addition, the recombinant virus was attenuated in both A129 and AG129 mice, yet replicated robustly in Vero cells (an approved cell line for vaccine production) to titers above 1×10$^6$ PFU/ml. Besides its application for vaccine development, the infectious clone can also be used as a reporter ZIKV (e.g., GFP or luciferase), which facilitates the tracking of viral replication in vivo and screening for antiviral inhibitors in a high-throughput manner (Shan et al., (2016) *ACS Infectious Diseases* 2, 170-72).

TABLE 3

Amino acid differences between the infectious cDNA clone and microcephaly ZIKV isolates

| Polyprotein position[a] | Associated protein and position | Microcephaly strains[b] | | Infectious clone |
|---|---|---|---|---|
| | | KU497555 | KU527068 | JN860885 |
| 106 | Capsid: 106 (or anchor C: 2) | Ala | Ala | Thr[c] |
| 123 | prM: 1 | Ala | Ala | Val[c] |
| 130 | prM: 8 | Ser | Ser | Asn[c] |
| 139 | prM: 17 | Asn | Asn | Ser[c] |
| 550 | E: 260 | Thr | Ser | Ser |
| 763 | E: 473 | Met | Met | Val[c] |
| 940 | NS1: 146 | Lys | Glu | Lys |
| 982 | NS1: 188 | Val | Val | Ala[c] |
| 1027 | NS1: 233 | Thr | Ala | Thr |
| 1143 | NS1: 349 | Met | Val | Met |
| 1259 | NS2A: 113 | Phe | Leu | Leu |
| 1274 | NS2A: 128 | Leu | Leu | Pro[c] |
| 1477 | NS2B: 105 | Thr | Thr | Ala[c] |
| 2086 | NS3: 584 | His | His | Tyr[c] |
| 2509 | NS4B: 240 | Thr | Iso | Thr |
| 2634 | NS5: 114 | Val | Val | Met[c] |
| 2831 | NS5: 311 | Val | Glu | Glu |
| 3392 | NS5: 872 | Val | Val | Met[c] |
| 3403 | NS5: 883 | Met | Met | Val[c] |

[a]The amino acid position of polyprotein is numbered based on the infectious cDNA clone strain FSS13025 (GenBank number JN860885)
[b]Three ZIKV strains from microcephaly fetuses are listed for sequence comparison: strain Fss13025 (GenBank number KU497555) and Natal RGN (GenBank number KU527068). The GenBank numbers are indicated.
[c]Residues in bold are from the infectious cDNA clone that are consistently different from the two microcephaly strains.

In summary, the current invention provides a multi-component platform to study ZIKV transmission and disease pathogenesis, and to develop countermeasures.

Material and Methods

Cells, Viruses, and Antibodies.

Vero cells were purchased from the American Type Culture Collection (ATCC, Bethesda, Md.), and maintained in a high glucose Dulbecco modified Eagle medium (DMEM) (Invitrogen, Carlsbad, Calif.) supplemented with 10% fetal bovine serum (FBS) (HyClone Laboratories, Logan, Utah) and 1% penicillin/streptomycin (Invitrogen) at 37° C. with 5% $CO_2$. *A. albopictus* C6/36 (C6/36) cells were grown in RPMI1640 (Invitrogen) containing 10% FBS and 1% penicillin/streptomycin at 28° C. with 5% $CO_2$. The parental ZIKV Cambodian strain FSS13025 (GenBank number JN860885.1) was isolated in 2010 from the blood of a patient from Cambodia. The following antibodies were used in this study: a mouse monoclonal antibody (mAb) 4G2 cross-reactive with *flavivirus* E protein (ATCC) and goat anti-mouse IgG conjugated with Alexa Fluor 488 (Thermo Fisher Scientific).

cDNA Synthesis and Cloning.

Viral RNA was extracted from viral stocks using QIAamp Viral RNA Kits (Qiagen). cDNA fragments covering the complete genome were synthesized from genomic RNA using SuperScript® III (RT)-PCR using primers (Table 4) according to the manufacturer's instructions (Invitrogen). FIG. 1A depicts the scheme to clone and assemble the full-genome of ZIKV. Plasmid pACYC177 (New England Biolabs, Ipswich, Mass.) was used to clone fragments B and A+B. Plasmid pCR2.1-TOPO (Invitrogen) was used to clone individual fragment C, D, and E. The full-length genomic cDNA was assembled using plasmid pACYC177. Bacterial strain Top 10 (Invitrogen) was used as the *E. coli* host for construction and propagation of cDNA clones. A standard cloning procedure was used, as previously reported for making WNV (Shi et al., (2002) *J Virol* 76, 5847-56) and DENV (Zou et al., (2011) *Antiviral Res* 91, 11-19) infectious clones. The virus-specific sequence of each intermediate clone was validated by Sanger DNA sequencing before it was used in subsequent cloning steps. The final plasmid containing full-length cDNA of ZIKV (pFLZIKV) was sequenced to ensure no undesired mutations. All restriction endonucleases were purchased from New England Biolabs (Beverly, Mass.).

RNA Transcription and Transfection.

Plasmid pFLZIKV, containing the full length cDNA of ZIKV, was amplified in *E. coli* Top10 and purified using MaxiPrep PLUS (Qiagen). For in vitro transcription, 10 µg of pFLZIKV was linearized with restriction enzyme ClaI. The linearized plasmid was extracted with phenol-chloroform and chloroform, precipitated with ethanol, and re-suspended in 15 µl of RNase-free water (Ambion, Austin, Tex.). The mMESSAGE mMACHINE kit (Ambion) was used to in vitro transcribe RNA in a 20-µl reaction with an additional 1 µl of 30 mM GTP solution. The reaction mixture was incubated at 37° C. for 2 h, followed by the addition of DNase I to remove the DNA template. The RNA was precipitated with lithium chloride, washed with 70% ethanol, re-suspended in RNase-free water, quantitated by spectrophotometry, and stored at −80° C. in aliquots. For transfection, approximately 10 µg of RNA was electroporated to 8×10$^6$ Vero cells in 0.8 ml of Ingenio® Electroporation Solution (Mirus, Madison, Wis.), in 4-mm cuvettes with the GenePulser apparatus (Bio-Rad) at settings of 0.45 kV and 25 µF, pulsing three times, with 3-second intervals. After a 10-min recovery at room temperature, the transfected cells were mixed with media and incubated in a T-175 flask (5% $CO_2$ at 37° C.). At different time points post-electroporation (p.t.), recombinant viruses in cell culture media were harvested, clarified by centrifugation at 500×g, stored in aliquots at −80° C., and subjected to analysis.

Indirect Immunofluorescence Assays (IFA).

IFA was performed to detect viral protein expression in ZIKV RNA-transfected Vero cells. Vero cells transfected with viral RNA were grown in an 8-well Lab-Tek chamber slide (Thermo Fisher Scientific, Waltham, Mass.). At indicated time points, the cells were fixed in 100% methanol at −20° C. for 15 min. After 1 h incubation in a blocking buffer containing 1% FBS and 0.05% Tween-20 in PBS, the cells were treated with a mouse monoclonal antibody 4G2 for 1 h and washed three times with PBS (5 min for each wash). The cells were then incubated with Alexa Fluor® 488 goat anti-mouse IgG for 1 h in blocking buffer, after which the cells were washed three times with PBS. The cells were mounted in a mounting medium with DAPI (4', 6-diamidino-2-phenylindole; Vector Laboratories, Inc.). Fluorescence images were observed under a fluorescence microscope equipped with a video documentation system (Olympus).

Restriction Enzyme Digestion Analysis to Differentiate Between Parental and Recombinant Viruses.

A restriction endonuclease site for SphI existing in the parental ZIKV was eliminated in the cDNA clone and the resulting recombinant virus. The disappearance of the SphI site was used to distinguish between the parental (with SphI site) and recombinant (without SphI site) viruses. Recombinant virus (harvested from culture media on day 6 p.t.) and parental virus were subjected to RNA extraction using QIAamp Viral RNA Kits (Qiagen). The extracted viral RNAs were used to amplify the 1258-bp fragments spanning the SphI site using primers E-1303V and NS1-2552-ClaI-R (Table 4). The RT-PCR products were digested with SphI and analyzed on a 0.8% agarose gel.

TABLE 4

Oligonucleotides used to construct the full-length cDNA of ZIKV

| Primers[a] | Primer sequence (5' to 3') |
|---|---|
| pACYC-14437-F | gcctacccggaactgagtgtc (SEQ ID NO: 5) |
| T7-5UTR-F | taatacgactcactatagAGTTGTTGATCTGTGTGAATC AGACTG (SEQ ID NO: 6) |
| T7-5UTR-R | TCACACAGATCAACAACTctatagtgagtcgtattagcg gccgc (SEQ ID NO: 7) |
| 1303-F | GCAAAGGGAGCCTGGTGACATGCGC (SEQ ID NO: 8) |
| 2552-ClaI-R | ccatcgatGACGAACACCCCTGTACCGC (SEQ ID NO: 9) |
| 2402-NotI-F | tctgcggccgcGGGTCTGAATACAAAGAATGG (SEQ ID NO: 10) |
| XbaI-4438-R | gctctagatatcgatttGGACTGTTTCCAGTGACTTCC (SEQ ID NO: 11) |
| EcoRI-4130-F | cggaattcACCATTTGTCATGGCCCTGGGACTAAC (SEQ ID NO: 12) |
| XbaI-6408-R | gctctagatatcgatttCTCTGGCGTCCATCCACCTCGG (SEQ ID NO: 13) |
| EcoRI-6098-F | cggaattcCAACATTTACCTCCAAGATGGCCTC (SEQ ID NO: 14) |
| XbaI-8470-R | gctctagatatcgatttCTTACCACAGCCCGCGTGCCAG (SEQ ID NO: 15) |
| KpnI-8266F | ggggtaccGTAGGTATGGGGAGGACTGGTCAGAG (SEQ ID NO: 16) |
| XbaI-11002-R | gctctagatatcgatttcatgataagatacattgatg (SEQ ID NO: 17) |
| 3'UTR-HDVr-F | GGGAAATCCATGGTTTCTggtcggcatggcatctc (SEQ ID NO: 18) |
| 3'UTR-HDVr-R | gagatgccatgccgaccAGAAACCATGGATTTCCCCAC ACCGGCC (SEQ ID NO: 19) |
| SphI-1638-F | ATTCCATTACCTTGGCAcGCTGGGGCAGACACC (SEQ ID NO: 20) |
| SphI-1670-R | GGTGTCTGCCCCAGCgTGCCAAGGTAATGGAAT (SEQ ID NO: 21) |

[a]The primers were named after the nucleotide position of viral sequence and polarity. F, viral genome sense; R, complementary sense. Nucleotide numbering is based on ZIKV strain FSS13025 (GenBank number JN860885).
[b]Viral and nonviral sequences are in uppercase and lowercase, respectively. Silent mutation to elliminate SphI restriction site in the E gene is also depicted in lowercase.

Plaque Assay.

Viral samples were ten-fold serially diluted six times in DMEM. For each dilution, 100 μl sample was added to a 12-well plate containing Vero cells at about 90% confluency. The infected cells were incubated for 1 h and swirled every 15 min to ensure complete coverage of the monolayer for even infection. After the incubation, 1 ml of methyl cellulose overlay containing 5% FBS 1% P/S was added to each well and the plate was incubated at 37° C. for four days. Following the incubation, methyl cellulose overlay was removed; the plate was washed twice with PBS, fixed with 3.7% formaldehyde, and incubated at room temperature for 20 min. After remove the fixative, the plate was stained with crystal 1% violet for 1 min. Visible plaques were counted and viral titers (PFU/ml) were calculated.

Replication Curves.

Subconfluent Vero and C6/36 cells in 12-well plates were inoculated with either parental or recombinant ZIKV at an MOI of 0.01 in triplicate wells. Virus stocks were diluted in DMEM containing 5% FBS and 1% penicillin/streptomycin. One hundred microliters of virus was added to each well of the 12-well plates. After 1 h attachment (5% $CO_2$ at 37° C. for Vero cells and at 28° C. for C6/36 cells), the inocula were removed. The cell monolayers were washed three times with PBS, Afterwards, 1 ml DMEM medium containing 2% FBS and 1% penicillin/streptomycin was added to each well. The plates were incubated for up to 6 days. The medium was collected daily and subjected to plaque assay as described above.

Virulence in Mice.

Both A129 and AG129 mice were used to examine the virulence of parental and recombinant ZIKVs. The details of parental ZIKV infection in A129 mice have been recently reported (Rossi et al., (2016) Characterization of a Novel Murine Model to Study Zika Virus, Am J Trop Med Hyg). Briefly, four week-old A129 mice were infected with $1 \times 10^5$ PFU via the intraperitoneal route. Five mice per group were used for parental and recombinant viruses. PBS was used to dilute the virus stocks to the desired concentration. The inoculum was back-titrated to verify the viral dose. Mock-infected mice were given PBS by the same route. Mice were weighed and monitored daily for signs of illness (hunched posture, ruffled fur, lethargy, etc.). Mice were bled via the retro-orbital sinus (RO) after being anesthetized every other day. Blood was clarified post collection by centrifugation at 3,380×g for 5 min and immediately stored at −80° C. for storage. Viral titers were determined by plaque assay on Vero cells. Mice were considered moribund if they did not respond to stimuli, were unable to remain upright, or lost 20% or more of their initial weight (consistent with the approved protocol).

The AG129 mice were bred and maintained in animal facilities at the University of Texas Medical Branch (UTMB). Young adult animals (6 weeks old) were inoculated by intraperitoneal injection with parental or recombinant ZIKV using a range of inocula. Following inoculation, mice were weighed daily and visually monitored to determine the course of infection. Mice exhibiting weight loss of >20% of initial body weight or neurologic disease were euthanized. Euthanized animals were counted as being dead on the following day for analysis. All animal work was completed in compliance with the UTMB policy as approved by the Institutional Animal Care and Use Committee (IACUC).

Experimental Infection of Mosquitoes with ZIKV.

*A. aegypti* colony mosquitoes derived from the Galveston, Tex. were fed for 30 min on blood meals consisting of 1% (weight/vol) sucrose, 20% (vol/vol) FBS, 5 mM ATP, 33% (vol/vol) PBS-washed human blood cells (UTMB Blood Bank), and 33% (vol/vol) DMEM medium and combined with 1 ml virus offered in Hemotek 2-ml heated reservoirs (Discovery Workshops) covered with a mouse skin. Virus titer in the blood meals ranged from 6.2 to 6.5 $log_{10}$ FFU/ml. Infectious blood meals were loaded on cartons containing *A. aegypti*. Engorged mosquitoes were incubated at 28° C., 80% relative humidity on a 12:12 h light:dark cycle with ad lib access to 10% sucrose solution for 14 days and then frozen at −20° C. overnight. To assess infection and dissemination, bodies and legs were individually homogenized (Retsch MM300 homogenizer, Retsch Inc., Newton, Pa.) in DMEM with 20% fetal bovine serum (FBS) and 250 μg/ml amphotericin B. Samples were centrifuged for 10 min at 5,000 rpm, and 50 μl of each sample supernatant were inoculated into 96-well plates containing Vero cells at 37° C. and 5% $CO_2$ for 3 days, when they were fixed with a mixture of ice-cold acetone and methanol (1:1) solution and immunostained as described below. Infection was determined by recovery of virus from the homogenized body and dissemination from the alimentary track into the hemocoel was determined by recovery of virus from the legs. The infection rate was recorded as the fraction of virus-positive bodies divided by the total number of bodies from engorged mosquitos and the disseminated infection rate is the number of virus-positive legs divided by the total number of engorged mosquitoes.

Focus Forming Assays and Immunostaining.

Ten-fold serial dilutions of virus in DMEM supplemented with 2% FBS and 250 μg/ml amphotericin B (Invitrogen, Carlsbad, Calif.) were added onto confluent Vero cell monolayers attached to 96-well Costar (Corning, N.Y.) plates and incubated for 1 h with periodic gentle rocking to facilitate virus adsorption at 37° C. Wells were then overlaid with 150 μl of DMEM supplemented with 2% FBS and 250 μg/ml amphotericin B and incubated undisturbed for 3 days at 37° C. Media overlay was aspirated and cell monolayers were rinsed once with PBS, pH 7.4 (Invitrogen, Carlsbad, Calif.), fixed with a mixture of ice-cold acetone and methanol (1:1) solution and allowed to incubate for 30 min at room temperature. Fixation solution was aspirated and plates were allowed to air dry. Plates were washed thrice with PBS supplemented with 3% FBS, followed by 1 h incubation with ZIKV-specific HMAF (hyper-immune ascitic fluid). Plates were washed thrice followed by an hour-long incubation with a secondary antibody conjugated to horseradish peroxidase (KPL, Gaithersburg, Md.). Detection proceeded with the addition of aminoethylcarbazole substrate (ENZO Life sciences, Farmingdale, Mass.) prepared according to the vendor's instructions.

TABLE 5

Overview for SEQ ID NO: 1

| | Nucleotide Location (length bp) | AA Length (MW) | Unique Enzyme sites Name (location) | primer |
|---|---|---|---|---|
| | | | NotI (14398) | 14222F |
| 5' UTR | 1-107 (107) | | NheI (53) | Aford |
| Capsid | 108-473 (366) | 122 (13.98 Kd) | | 410V |
| pr | 474-752 (279) | 93 18.5 | | 688C |
| M | 753-977 (225) | 75 Kd | | 839V |
| Envelope | 978-2489 (1512) | 504 (55 Kd) | AvrII (1533) | 1303V<br>1785V<br>2255V<br>2402V |
| NS1 | 2490-3545 (1056) | 352 (38.7 Kd) | PmlI (3348) | 2552C<br>2707V<br>3207V<br>3257V<br>3285V<br>3498C |
| NS2A | 3546-4223 (678) | 226 (24.5 Kd) | SphI (3861) | 3659V<br>3805F<br>4130V<br>4158V |
| NS2B | 4224-4613 (390) | 130 (14.3 Kd) | | 4323F<br>4438R |

TABLE 5-continued

Overview for SEQ ID NO: 1

| | Nucleotide Location (length bp) | AA Length (MW) | Unique Enzyme sites Name (location) | primer |
|---|---|---|---|---|
| NS3 | 4614-6464 (1851) | 617 (67.8 Kd) | NaeI (6344) | 4662V 5150V 5618V 6098F 6138V 6303F 6408R |
| NS4A | 6465-6845 (381) | 127 (13.97 Kd) | | 6674V |
| 2K | 6846-6914 (69) | 23 (2.53 Kd) | | |
| NS4B | 6915-7667 (753) | 251 (27.6 Kd) | | 7233V 7597V |
| NS5 | 7668-10376 (2709) | 903 (99.3 Kd) | AflII (8044) SfiI (8412) EcoRI (9174) | 7756V 8316V 8382F 8806V 9363V 9854V 10000C 10310V |
| 3' UTR | 10270-10807 (453) | | | 10522C 10808C |
| HDvr | 10808-10874 (67) gggtcggcatggcatctccacctcctcgcggtcc gacctgggctacttcggtaggctaagggagaag (SEQ ID NO: 4) | | | |
| pACYC177 | 10875-14274 (3400 bp) | | ClaI(10878) | 11168V |
| T7 promoter | 14275-14292 (18) taatacgactcactatag (SEQ ID NO: 3) | | | |

Example 2

Zika Virus Plaque Reduction Neutralization Test (PRNT)

Assay Design.

The inventors chose to infect Vero cells with *Renilla* luciferase ZIKV and DENV-2 in a 96-well format for assay development. Since the goal is to measure the neutralization titters of sera that block virus to infect cells, the inventors limited the infection time to 24 h to avoid multiple rounds of infections. Cell permeable substrate ViviRen was selected to measure luciferase activity because it can penetrate into cells to generate luciferase signals without cell lysis. The inventors first determined the optimal virus inoculum per well (seeded with a nearly confluent monolayer of Vero cells) to achieve a liner range of luciferase signal at 24 h post-infection (p.i.; FIG. 11). The inventors chose the infection dose of multiplicity of infection (MOI) of 0.1 for the neutralization assay; at this infection dose, the assay consistently generated luciferase signals of 100- to 110-fold higher than that from mock-infected cells (FIG. 11). FIG. 9 summarizes the optimal assay protocol. Specifically, Vero cells ($1.5 \times 10^4$ in 50 µl medium without phenol red per well) were seeded in a white opaque 96-well plate. After an overnight culturing, the cells were infected with reporter ZIKV or reporter DENV that had been pre-incubated with serially diluted patient sera at 37° C. for 60 min. At 24 hours post infection, luciferase substrate was added to the infected cells. The plates were quantified for luciferase activities. The dose-responsive curves of luciferase activity were used to calculate the 90% neutralization titer ($NT_{90}$) of each serum using the Prism Software. The reporter assay is homogeneous (i.e., add cells/virus/substrate and measure luciferase activity without any steps of medium aspiration or washing) and can be completed in less than 48 hours.

Selection of Patient Sera.

A total of 91 human sera were selected to validate the reporter virus-based neutralization assay. These sera were categorized into four groups based on their known ZIKV and DENV $PRNT_{90}$ values which had been previously determined by the traditional plaque assay. The $PRNT_{90}$ values of <, =, and >10 are defined as negative, marginally positive, and positive in neutralizing activities, respectively. As shown in Table 6, group I specimens (n=10; specimens number 1 to 10) were negative in neutralizing ZIKV and DENV. Group II specimens (n=6; specimens number 11 to 16) were negative or marginally positive in neutralizing ZIKV, but positive in neutralizing DENV. Group III specimens (n=23; specimens number 17 to 39) were positive in neutralizing ZIKV, but negative or marginally positive in neutralizing DENV. Group IV specimens (n=43 patients; specimen number 40-91) were positive in neutralizing both ZIKV and DENV. It is worth pointing out that, due to possible cross-neutralization of antibodies among ZIKV and DENV, patients from group IV could have one of the three possible infections: (i) infections with both ZIKV and DENV, (ii) infection with ZIKV only but with antibodies cross-reactive to DENV, or (iii) infection with DENV only but with antibodies cross-reactive to ZIKV.

TABLE 6

Comparison of neutralization titers from plaque assay ($PRNT_{90}$) and reporter virus assay ($NT_{90}$)*

| Specimen number | Plaque assay | | Luciferase assay | |
| --- | --- | --- | --- | --- |
| | ZIKV | DENV | ZIKV | DENV |
| 1 | <10 | <10 | <10 | <10 |
| 2 | <10 | <10 | <10 | <10 |
| 3 | <10 | <10 | <10 | <10 |
| 4 | <10 | <10 | <10 | <10 |
| 5 | <10 | <10 | <10 | <10 |
| 6 | <10 | <10 | <10 | <10 |
| 7 | <10 | <10 | <10 | <10 |
| 8 | <10 | <10 | <10 | <10 |
| 9 | <10 | <10 | <10 | <10 |
| 10 | <10 | <10 | <10 | <10 |
| 11 | <10 | 40 | <10 | 66 |
| 12 | <10 | 40 | <10 | 74 |
| 13 | <10 | 40 | <10 | 79 |
| 14 | 10 | 40 | <10 | 181 |
| 15 | 10 | 80 | 26 | 99 |
| 16 | 10 | 160 | 27 | 448 |
| 17 | 40 | <10 | 109 | <10 |
| 18 | 40 | <10 | 142 | <10 |
| 19 | 80 | <10 | 257 | <10 |
| 20 | 160 | <10 | 249 | <10 |
| 21 | 160 | <10 | 489 | 10 |
| 22 | 160 | <10 | 661 | <10 |
| 23 | 160 | <10 | 1321 | <10 |
| 24 | 320 | <10 | 133 | <10 |
| 25 | 320 | <10 | 313 | 43 |
| 26 | 320 | <10 | 407 | 13 |
| 27 | 320 | <10 | 494 | 27 |
| 28 | 320 | <10 | 759 | 13 |
| 29 | 320 | <10 | 991 | <10 |
| 30 | 320 | 10 | 465 | 10 |
| 31 | 640 | <10 | 440 | <10 |
| 32 | 640 | <10 | 890 | <10 |
| 33 | 640 | <10 | 1076 | <10 |
| 34 | 640 | <10 | 1316 | <10 |
| 35 | 640 | <10 | 1355 | <10 |
| 36 | 1280 | <10 | 469 | <10 |
| 37 | 1280 | <10 | 532 | 30 |
| 38 | 1280 | <10 | 803 | <10 |
| 39 | 1280 | <10 | 1160 | <10 |
| 40 | 20 | 640 | 142 | 1811 |
| 41 | 20 | 1280 | 89 | 1355 |
| 42 | 80 | 640 | 300 | 576 |
| 43 | 160 | 40 | 178 | 144 |
| 44 | 160 | 40 | 217 | 133 |
| 45 | 160 | 320 | 214 | 1886 |
| 46 | 160 | 320 | 631 | 636 |
| 47 | 160 | 640 | 292 | 762 |
| 48 | 160 | 640 | 389 | 531 |
| 49 | 160 | 640 | 1215 | 2116 |
| 50 | 160 | 2560 | 322 | 1239 |
| 51 | 160 | 2560 | 1071 | 3125 |
| 52 | 320 | 20 | 949 | 32 |
| 53 | 320 | 40 | 375 | 149 |
| 54 | 320 | 40 | 424 | 259 |
| 55 | 320 | 160 | 757 | 462 |
| 56 | 320 | 640 | 885 | 1085 |
| 57 | 320 | 2560 | 2107 | 2437 |
| 58 | 320 | 5120 | 3217 | 8561 |
| 59 | 640 | 640 | 2395 | 1223 |
| 60 | 640 | 640 | 2785 | 1614 |
| 61 | 640 | 1280 | 804 | 1158 |
| 62 | 640 | 1280 | 906 | 4897 |
| 63 | 640 | 1280 | 925 | 1098 |
| 64 | 640 | 1280 | 2134 | 4351 |
| 65 | 640 | 1280 | 2150 | 2658 |
| 66 | 640 | 2560 | 889 | 17346 |
| 67 | 640 | 2560 | 1207 | 2803 |
| 68 | 640 | 2560 | 1356 | 4492 |
| 69 | 640 | 5120 | 1524 | 6910 |
| 70 | 1280 | 20 | 673 | 355 |
| 71 | 1280 | 80 | 1563 | 145 |
| 72 | 1280 | 640 | 2483 | 1834 |
| 73 | 1280 | 1280 | 1760 | 1183 |
| 74 | 1280 | 1280 | 2804 | 2705 |
| 75 | 1280 | 1280 | 3709 | 2250 |
| 76 | 1280 | 2560 | 1173 | 5418 |
| 77 | 1280 | 2560 | 1925 | 7430 |
| 78 | 1280 | 2560 | 2897 | 3530 |
| 79 | 1280 | 2560 | 9156 | 24147 |
| 80 | 1280 | 5120 | 2937 | 3174 |
| 81 | 1280 | 20480 | 7729 | 31361 |
| 82 | 2560 | 320 | 1279 | 345 |
| 83 | 2560 | 320 | 1892 | 746 |
| 84 | 2560 | 320 | 2654 | 350 |
| 85 | 2560 | 1280 | 3885 | 1258 |
| 86 | 2560 | 2560 | 3545 | 4016 |
| 87 | 2560 | 2560 | 3114 | 3811 |
| 88 | 2560 | 20480 | 2555 | 18316 |
| 89 | 5120 | 5120 | 934 | 2353 |
| 90 | 5120 | 1280 | 6352 | 1237 |
| 91 | 5120 | 5120 | 12068 | 8925 |

Comparison of Traditional PRNT and Reporter Virus Assays.

All 91 patient samples were subjected to the reporter ZIKV and DENV assay. Table 6 summarizes the $NT_{90}$ values derived from the reporter assay as well as the $PRNT_{90}$ results derived from the traditional plaque assay. Since the $NT_{90}$ values of the reporter assay were calculated using Prism Software, most of these numbers fell between two serum dilutions sandwiching the 90% inhibition of luciferase signals. Comparison of the neutralization results from the two assays revealed three features. (i) For any given specimen, the relative neutralization titers against ZIKV and DENV are in full agreement between the reporter and plaque assays. FIG. 10 shows the scatter plot of 90% neutralization titters derived from the two assay formats for ZIKV and DENV, suggesting a general concordance between the reporter and plaque assays. (ii) Specimens from groups II and III exhibited virus type-specific neutralizing activities against DENV and ZIKV, respectively, when tested with both plaque and reporter virus assays (Table 6). Such specificity was particularly noteworthy for specimens 36-39 that potently neutralized ZIKV ($PRNT_{90}$ or $NT_{90}$ values of 469-1280) but could not or barely neutralize DENV (all $NT_{90}$ values of <10, except specimen 37 with an $NT_{90}$ of 30). (iii) The neutralization titers derived from the reporter ZIKV and DENV assay were on average 2.5- and 2.4-fold higher than those derived from the corresponding ZIKV and DENV plaque assay, respectively. This observation is in agreement with a recent study reporting that the neutralization titers measured by a single-round infection assay using WNV GFP replicon particles were higher than the traditional plaque assay (Dowd et al., 2016 *Science*

354:237-40). The larger dynamic range of the reporter virus assay suggests a higher sensitivity than the plaque assay in differentiating the neutralization titers of patient specimens. Collectively, the results demonstrate that the reporter virus assay has a more dynamic diagnostic range and maintains the relative specificity of the traditional plaque assay.

Materials and Methods

Cells and Viruses.

Vero and BHK-21 cells were purchased from the American Type Culture Collection (ATCC, Bethesda, Md.), and maintained in a high-glucose Dulbecco's modified Eagle's medium (DMEM) supplemented with 10% fetal bovine serum (FBS; HyClone Laboratories, South Logan, Utah) and 1% penicillin/streptomycin at 37° C. with 5% $CO_2$. For the traditional PRNT assay, the inventors used ZIKV Puerto Rico strain PRVABC59 and DENV-2 New Guinea (NGC) strain. *Renilla* luciferase ZIKV (strain FSS13025) and DENV-2 (strain NGC) were prepared from the previously constructed infectious cDNA clones (Shan et al., 2016 *ACS Infectious Diseases* 2:170-72; Zou et al., 2011 *Antiviral Res* 91:11-19). Briefly, the cDNA plasmids were used to in vitro transcribe genomic RNAs. The luciferase ZIKV and DENV RNA transcripts were transfected into Vero and BHK-21 cells, respectively. The transfected cells were cultured in DMEM without phenol red (to eliminate its interference with luciferase signal measurement). On day 10 and 6 post-transfection (when cytopathic effects started to appear in the ZIKV and DENV-2 RNA-transfected cells, respectively), culture fluids were collected and quantified for viral titers using an immuno-staining focus assay and plaque assay, respectively, as previously reported (Shan et al., 2016 *Cell Host Microbe* 19:891-900).

Serum Specimens.

A total of 91 sera from de-identified clinical specimens were used in the study. The specimens came from two sources: 10 samples from University of Texas Medical Branch (UTMB) that were submitted for routine screening for agents other than Zika virus, and 81 samples from New York State Department of Health that were submitted for ZIKV IgM-capture ELISA and Arbovirus MIA testing [a WNV E protein-based microsphere immunoassay as reported previously (Wong et al., 2003 *J Clin Microbiol* 41:4217-23)]. The UTMB samples were carefully selected from the patients with least possibility of exposure to ZIKV and DENV infection. As described recently (Wong et al., 2017 *E Bio Medicine*), the sera from New York State Department of Health were almost all collected from New York State residents who returned from travels to ZIKV epidemic areas (including the Caribbean and Central and South America) from the end of 2015 to October of 2016. Most sera were collected within two months after travel with possible exposure to ZIKV. In some instances, patients requested diagnostic tests at later time points. Since many individuals were asymptomatic, the dates of disease onset were not known. The demographic profile of this population is approximately 19% Hispanic and 6% Non-Hispanic Asian and Pacific Islander. Based on this demographic profile, it is not surprising that many of these individuals may have *flavivirus* immunity, primarily to DENV and other flaviviruses as well as YF vaccines. The information about patient history with respect to vaccination and previous *flavivirus* infections is not available.

Reporter Virus-Based Neutralization Assay.

Reporter ZIKV and DENV-2 containing a *Renilla* luciferase gene was used to measure the neutralization titers of patient sera against ZIKV or DENV-2 in a 96-well plate format. Briefly, Vero cells ($1.5 \times 10^4$ cells per well) were seeded into a 96-well white opaque plate (Corning Costar, St. Louis, Mo.) one day prior to infection. Patient sera were initially diluted as 10-fold in a phenol red-free DMEM medium (ThermoFisher Scientific, Sugar Land, Tex.) containing 2% FBS and 1% penicillin/streptomycin, followed by 2-fold serial dilution ($2^1$ to $2^9$). Thirty microliters of each serum dilution were mixed thoroughly with 30 µl reporter ZIKV or DENV-2 and incubated at 37° C. for 1 hour to form antibody-virus complexes. Afterwards, 50 µl serum-virus mixtures were inoculated onto the Vero cell monolayer (containing 50 µl phenol red-free DMEM medium with 2% FBS and 1% penicillin/streptomycin). The plate was incubated at 37° C. for 24 hour. The intracellular luciferase signals were measured using ViviRen substrates (Promega, Madison, Wis.) on Cytation 5 Cell Imaging Multi-Mode Reader (Biotek, Winooski, Vt.) according to the manufacturer's instructions. Medium containing the same amounts of reporter ZIKV or DENV-2 but without specimen serum was used as non-treatment controls. Luciferase signals from the non-treatment controls were set at 100%. Luciferase signals from each diluted serum-treated samples were normalized to those from the non-treatment controls. A four-parameter sigmoidal (logistic) model in the software GraphPad Prism 7 was used to calculate the neutralization titers that suppressed 90% of the luciferase signals of the non-treatment control ($NT_{90}$).

Plaque Reduction Neutralization Test (PRNT).

A standard double-layer plaque assay (Shi et al., 2002 *J Virol* 76:5847-56) was performed to determine the PRNTs of each patient serum. The inventors used ZIKV Puerto Rico strain PRVABC59 and DENV-2 New Guinea strain in the PRNT assay. Specifically, serial dilutions of serum samples (1/10 for the first dilution followed by serial ½ dilutions) were mixed with an equal amount of virus suspension containing 200 plaque-forming units (PFU) in 0.1 ml. After incubating the mixtures at 37° C. for 1 hour, each virus-diluted serum sample (0.1 ml) was inoculated onto one well of a 6-well tissue culture plate containing a confluent monolayer of Vero cells. After incubating the plate at 37° C. for 1 hour, an agar overlay was added to the infected cell monolayer, and the plate was further incubated at 37° C. When virus plaques became visible, a second overlay containing neutral red was added, and plaques were counted. The antibody titer was determined as the serum dilution that inhibited 90% of the tested virus inoculum ($PRNT_{90}$).

The invention claimed is:

1. An assay for detecting flavivirus infection comprising:
   contacting a sample from a subject suspected of having a flavivirus infection with a reporter Zika virus (rZIKV), the rZIKV configured to produce a detectable signal when expressed in viable cell, forming a reporter mixture and incubating the reporter mixture at a temperature of 35 to 40° C.;
   contacting a host cell monolayer with the reporter mixture under cell growth conditions at about 37° C. forming an inoculated cell monolayer;
   measuring the reporter signal produced by the inoculated cell monolayer and normalizing the measured signal to a control; and
   calculating a ZIKV antibody titer of the sample using the reporter signal measurements.

2. The assay of claim 1, wherein a serial dilution of the sample contacted with the rZIKV.

3. The assay of claim 1, wherein a plurality of samples are assayed individually.

4. The assay of claim 1, wherein the sample is a blood sample.

5. The assay of claim 1, wherein the sample is from a pregnant subject.

6. The assay of claim 1, wherein the subject is a mammalian subject.

7. The assay of claim 6, wherein the subject is human.

8. The assay of claim 1, wherein the rZIKV is a luciferase reporter ZIKV.

9. The assay of claim 1, wherein the luciferase is *Renilla* luciferase.

10. The assay of claim 1, wherein the cell monolayer is a Vero cell monolayer.

11. The assay of claim 1, wherein the cell monolayers are assayed in a multi-well plate.

12. The assay of claim 1, wherein the inoculated cells are incubated for about 12, 24, 36, or 48 hours before measuring the reporter signal.

13. The assay of claim 1, further comprising:
contacting a sample from a subject suspected of having a flavivirus infection with a reporter dengue virus (rDENV), the rDENV configured to produce a detectable signal when infecting a viable cell, forming a reporter mixture and incubating the reporter mixture at a temperature of 35 to 40° C.;
contacting a host cell monolayer with the reporter mixture under cell growth conditions at about 37° C. forming an inoculated cell monolayer;
measuring the reporter signal produced by the inoculated cell monolayer and normalizing the measured signal to a control; and
calculating a DENV antibody titer of the sample using the reporter signal measurements.

14. The assay of claim 1, further comprising performing virus specific DNA amplification using a second sample from the subject suspected of having a flavivirus infection.

15. The assay of claim 14, wherein the DNA amplification is a viral RT-PCR assay.

16. A recombinant DNA expression cassette comprising a flavivirus nucleic acid segment that is at least 95% identical to the nucleic acid sequence of SEQ ID NO:1.

17. A recombinant flavivirus genome comprising a nucleic acid sequence SEQ ID NO: 1 and a heterologous nucleic acid segment.

18. The recombinant flavivirus of claim 17, wherein the heterologous nucleic acid segment encodes a reporter protein.

19. The recombinant flavivirus of claim 18, wherein the reporter protein is a fluorescent protein.

\* \* \* \* \*